US012514723B2

(12) United States Patent
Mitha et al.

(10) Patent No.: US 12,514,723 B2
(45) Date of Patent: Jan. 6, 2026

(54) SYSTEM AND METHODS FOR COMPRESSING ENDOVASCULAR DEVICES

(71) Applicant: FLUID BIOMED INC., Calgary (CA)

(72) Inventors: Alim P. Mitha, Calgary (CA); John H. Wong, Calgary (CA)

(73) Assignee: FLUID BIOMED INC., Calgary (CA)

( * ) Notice: Subject to any disclaimer, the term of this patent is extended or adjusted under 35 U.S.C. 154(b) by 295 days.

(21) Appl. No.: 17/991,753

(22) Filed: Nov. 21, 2022

(65) Prior Publication Data

US 2023/0190503 A1 Jun. 22, 2023

Related U.S. Application Data

(63) Continuation-in-part of application No. 16/810,481, filed on Mar. 5, 2020, now Pat. No. 11,504,254.

(51) Int. Cl.
*A61F 2/966* (2013.01)

(52) U.S. Cl.
CPC .................................... *A61F 2/966* (2013.01)

(58) Field of Classification Search
CPC ........ A61F 2/966; A61F 2/962; A61F 2/9525; A61F 2/95; A61F 2/97; A61F 2002/9665; A61F 2002/9534
See application file for complete search history.

(56) References Cited

U.S. PATENT DOCUMENTS

| | | | |
|---|---|---|---|
| 6,202,272 B1 | 3/2001 | Jackson | |
| 8,151,445 B1 | 4/2012 | Warriner et al. | |
| 8,608,795 B2 | 12/2013 | Melsheimer et al. | |
| 8,753,384 B2 | 6/2014 | Leanna | |
| 9,717,502 B2 | 8/2017 | Teoh et al. | |
| 9,814,466 B2 | 11/2017 | Kadam | |
| 10,182,931 B2 | 1/2019 | Pung et al. | |
| 10,201,444 B2 | 2/2019 | Rusk et al. | |
| 10,292,851 B2 | 5/2019 | Gorochow | |
| 10,405,868 B2 | 9/2019 | Tompkins et al. | |
| 10,555,824 B2 | 2/2020 | Dorn et al. | |
| 10,952,739 B2 * | 3/2021 | Plaza | A61B 17/12109 |
| 11,504,254 B2 | 11/2022 | Mitha et al. | |
| 2008/0127707 A1 | 6/2008 | Kokish et al. | |
| 2008/0262592 A1 | 10/2008 | Jordan et al. | |
| 2009/0192518 A1 | 7/2009 | Golden et al. | |
| 2009/0299449 A1 | 12/2009 | Styrc | |
| 2013/0268064 A1 | 10/2013 | Duffy | |
| 2014/0012369 A1 | 1/2014 | Murry, III et al. | |
| 2016/0166372 A1 | 6/2016 | Villareal et al. | |

(Continued)

FOREIGN PATENT DOCUMENTS

| | | | |
|---|---|---|---|
| WO | 9951167 A2 | 10/1999 | |
| WO | 2017139421 A1 | 8/2017 | |

OTHER PUBLICATIONS

U.S. Appl. No. 16/810,481 , Advisory Action, Mailed On May 17, 2022, 4 pages.

(Continued)

*Primary Examiner* — Katherine Shi
*Assistant Examiner* — Andrew Restaino
(74) *Attorney, Agent, or Firm* — Kilpatrick Townsend & Stockton LLP

(57) ABSTRACT

This disclosure relates to systems and methods for compressing reversibly compressible endovascular devices for loading into delivery catheters prior to deployment in lumen of a vessel.

13 Claims, 42 Drawing Sheets

(56) References Cited

U.S. PATENT DOCUMENTS

| | | | |
|---|---|---|---|
| 2016/0250051 | A1 | 9/2016 | Lim et al. |
| 2017/0296791 | A1 | 10/2017 | Benjamin et al. |
| 2017/0348099 | A1 | 12/2017 | Mendelson et al. |
| 2018/0280174 | A1 | 10/2018 | Dwork |
| 2019/0151067 | A1 | 5/2019 | Zucker et al. |

OTHER PUBLICATIONS

U.S. Appl. No. 16/810,481 , "Corrected Notice of Allowability", Oct. 13, 2022, 5 pages.
U.S. Appl. No. 16/810,481 , Final Office Action, Mailed On Feb. 9, 2022, 25 pages.
U.S. Appl. No. 16/810,481 , Final Office Action, Mailed On May 11, 2021, 25 pages.
U.S. Appl. No. 16/810,481 , Non-Final Office Action, Mailed On Oct. 26, 2021, 26 pages.
U.S. Appl. No. 16/810,481 , Non-Final Office Action, Mailed On Jan. 22, 2021, 36 pages.
U.S. Appl. No. 16/810,481 , Notice of Allowance, Mailed On Jul. 18, 2021, 16 pages.
PCT/CA2021/050300 , "International Search Report", May 13, 2021, 3 pages.
Pumar et al., "Preliminary Experience With Leo Self-Expanding Stent for the Treatment of Intracranial 35 Aneurysms", AJNR Am J Neuroradiol., vol. 26, No. 10, Nov.-Dec. 2005, pp. 2573-2577.

* cited by examiner

SYSTEM AND METHODS FOR COMPRESSING ENDOVASCULAR DEVICES

CROSS REFERENCE TO RELATED APPLICATION

This application is a Continuation-in-part of U.S. patent application Ser. No. 16/810,481, filed Mar. 5, 2020, which is hereby incorporated by reference in its entirety.

BACKGROUND OF THE INVENTION

1. Field of Invention

This disclosure relates to endovascular devices. In particular, this disclosure relates systems and methods compressing reversibly compressible endovascular devices for loading into delivery catheters prior to deployment in the body.

2. Description of Related Art

An endovascular device (ED) is an implantable medical device, such as a stent, which can be used to treat a variety of vascular conditions. Most typically, an ED is a tubular or cylindrical structure which is surgically inserted into a blood vessel to effect mechanical support for the walls of the vessel, to effect some change in the blood flow such as flow diversion, and/or to deliver therapeutics at the point of deployment within the vessel.

Often, an ED will be resiliently deformable/compressible so that it can be compressed for loading in a delivery catheter, and then be expanded upon deployment into a lumen of a vessel of a patient. Currently, reversibly compressible EDs are compressed or crimped to a significantly smaller diameter than the blood vessel, and provided by manufacturers in a compressed position within a delivery sheath. The compressed ED can then be transferred into a delivery catheter when needed, and advanced through the delivery catheter to the intended location in the patient's blood vessel. The reversibly compressible ED will typically have an elastic bias to have a nominal size compared with the blood vessel when it is in a compressed within the delivery catheter, such that it self-expands to fit the vessel when deployed in situ.

Reversibly compressible EDs are compressed and preloaded into a delivery sheath at the site of factory manufacture. The equipment for this compression may be pneumatic compression dies as disclosed in, for example, U.S. Pat. No. 8,151,445 B1, WO 2017/139421, and US20080127707A1. Such equipment is typically large, powered, metal, immobile, and difficult to sterilize. Accordingly, such equipment may be well-suited for use at an ED manufacturing facility, but is generally unsuitable for use at a point of care such as a surgical setting.

Hand-held crimping tools exist and are disclosed in, for example, U.S. Pat. No. 6,202,272 B1. However, such tools are large, heavy, and impractical to provide with every packaged ED. Accordingly, they are not practical to sterilize in the surgical setting.

SUMMARY OF THE INVENTION

The present inventors recognized a need to develop an ED loading system that can be used at the point of care so that reversibly compressible EDs can be packaged and provided by the manufacturer, and stored, in a non-compressed position. Otherwise, EDs that are maintained in a compressed position may suffer from stress relaxation of the materials used to manufacture the ED, which include but are not limited to, non-shape memory metals and polymers. Current EDs do not include a method of crimping the ED in case the ED needs to be packaged in the fully expanded configuration and then crimped at the point of care for immediate delivery into the patient.

The delivery systems disclosed herein can be used for EDs that are provided in a non-compressed configuration, in order to crimp them into a delivery sheath at the point of care or before packaging. It has the advantage of use for laser-cut (either open cell or closed cell designs) as well as for braided stents. It can be used at the point of care for EDs that are required to be delivered in the fully expanded configuration, due to the avoidance of stress relaxation of the stent ED which includes, but are not limited to, non-shape memory metals as well as polymers.

Various aspects of this disclosure relate to a system for the radial compression of a reversibly compressible endovascular device (ED) prior to deployment. The system comprises the ED, wherein the ED comprises a tubular body, wherein the body is expandable between a compressed position and a non-compressed position, the tubular body having an inner surface, an outer surface, opposed distal and proximal ED ends, and opposed distal and proximal ED openings. The system further comprises a delivery sheath sized to receive and maintain the ED in the compressed position, the delivery sheath having a delivery sheath opening having a diameter sized to receive the ED into the delivery sheath in a compressed form. The system further comprises a collapsible compressor for compressing the ED for reception by the delivery sheath through the delivery sheath opening. The compressor comprises a generally tapered structure defining an interior space, the tapered structure comprising distal and proximal compressor ends, wherein the proximal compressor end is proximal to the delivery sheath opening, wherein the distal compressor end comprises a distal compressor opening sized to receive the ED in the non-compressed position, wherein the tapered structure tapers from the distal compressor opening toward the proximal compressor end such that the cross section of the interior space diminishes toward the proximal compressor end, wherein the cross sectional area of the interior space at the proximal compressor end is equal to or less than the cross sectional area of the delivery sheath opening, and wherein an interior surface of the tapered structure is frictionally engaged with the outer surface of the ED, wherein the compressor is operable to be urged proximally with the ED frictionally engaged therein through the delivery sheath opening to collapse the compressor, wherein collapse of the compressor upon reception within the delivery sheath exerts a radial force upon the ED sufficient to compress the ED into the compressed position for reception in the delivery sheath. The system further comprises a compressor support for providing lateral support for an exterior surface of the compressor as it is urged proximally through the delivery sheath opening, the compressor support comprising a body comprising an interior wall defining an insertion bore for receiving the compressor and ED within the body, the insertion bore having a generally frustoconical shape that tapers between a broad distal opening of the body through which the compressor and ED are received within the insertion bore in the non-compressed position and a narrower proximal opening of the body configured for communication with the delivery sheath opening. The interior wall of the body is configured to provide lateral support to the exterior surface of the compressor as the compressor is urged proximally through the proximal opening of the body and into the delivery sheath through delivery sheath opening.

In various embodiments, a width of the proximal opening of the body is smaller than the diameter of the delivery sheath.

In various embodiments, a taper angle of the generally frustoconical shape is complimentary to a taper angle of the tapered structure of the collapsible compressor.

In various embodiments, the compressor support further comprises a first tubular portion defining an interior space of the first tubular portion in communication with the insertion bore of the body. The first tubular portion comprises distal and proximal first tubular portion ends, wherein the distal first tubular portion end is proximal to the proximal opening of the body, wherein the tubular structure has a width larger than the diameter of the delivery sheath.

In various embodiments, the compressor support further comprises a second tubular portion defining an interior space of the second tubular portion in communication with the insertion bore of the body. The second tubular portion comprises distal and proximal second tubular portion ends, wherein the proximal second tubular portion end is proximal to the distal opening of the body, wherein the tubular structure has a length and width sized to receive the ED in the non-compressed position.

In various embodiments, the proximal second tubular portion end is the same size as the distal opening of the body.

In various embodiments, the system further comprises a push wire detachably attached to the ED and disposed within the delivery sheath. The push wire is also disposed within the ED though the proximal compressor opening and through the proximal opening of the body.

In various embodiments, the system further comprises a hollow compressor tube attached to the compressor and disposed within the delivery sheath. The hollow compressor tube is operable to be advanced proximally through the delivery sheath to urge the compressor and the ED frictionally engaged therein through the delivery sheath opening.

Various aspects of the disclosure relate to a method of loading a reversibly compressible endovascular device (ED) into a delivery sheath having an interior width less than the radial width of the ED in an expanded position. The method comprises urging a compressor with the ED frictionally engaged therein, the compressor comprising a tapered structure tapering from a distal compressor end toward a proximal compressor end of the tapered structure, into the delivery sheath through a delivery sheath opening to radially compress the ED to an unexpanded position. The method further comprises providing, exterior to the delivery sheath, lateral support to an exterior surface of the compressor as it is urged toward and through the delivery sheath opening.

In various embodiments, lateral support is provided by an interior wall of a body of a compressor support. The compressor support comprises a body comprising an interior wall defining an insertion bore for receiving the compressor and ED within the body, the insertion bore having a generally frustoconical shape that tapers between a broad distal opening of the body through which the compressor and ED are received within the insertion bore in the non-compressed position and a narrower proximal opening of the body configured for communication with the delivery sheath opening.

In various embodiments, wherein the width of the proximal opening of the body is smaller than the diameter of the delivery sheath.

In various embodiments, a taper angle of the generally frustoconical shape is complimentary to a taper angle of the tapered structure of the collapsible compressor.

In various embodiments, the compressor support further comprises a first tubular portion defining an interior space of the first tubular portion in communication with the insertion bore of the body, the first tubular portion comprising distal and proximal first tubular portion ends. The distal first tubular portion end is proximal to the proximal opening of the body, wherein the tubular structure has a width larger than the diameter of the delivery sheath.

In various embodiments, the compressor support further comprises a second tubular portion defining an interior space of the second tubular portion in communication with the insertion bore of the body, the second tubular portion comprising distal and proximal second tubular portion ends. The proximal second tubular portion end is proximal to the distal opening of the body, wherein the tubular structure has a length and width sized to receive the ED in the non-compressed position.

In various embodiments the proximal second tubular portion end is the same size as the distal opening of the body.

Various aspects of the disclosure relate to a kit for the radial compression of a reversibly compressible endovascular device (ED) prior to deployment. The kit comprises the ED, wherein the ED comprises a tubular body, wherein the body is expandable between a compressed position and a non-compressed position, the tubular body having an inner surface, an outer surface, opposed distal and proximal ED ends, and opposed distal and proximal ED openings. The kit further comprises a delivery sheath sized to receive and maintain the ED in the compressed position, the delivery sheath having a delivery sheath opening having a diameter sized to receive the ED into the delivery sheath in a compressed form. The kit further comprises a collapsible compressor for compressing the ED for reception by the delivery sheath through the delivery sheath opening, wherein the compressor comprises a generally tapered structure defining an interior space, the tapered structure comprising distal and proximal compressor ends, wherein the proximal compressor end is proximal to the delivery sheath opening, wherein the distal compressor end comprises a distal compressor opening sized to receive the ED in the non-compressed position, wherein the tapered structure tapers from the distal compressor opening toward the proximal compressor end such that the cross section of the interior space diminishes toward the proximal compressor end, wherein the cross sectional area of the interior space at the proximal compressor end is equal to or less than the cross sectional area of the delivery sheath opening, and wherein an interior surface of the tapered structure is frictionally engaged with the outer surface of the ED, wherein the compressor is operable to be urged proximally with the ED frictionally engaged therein through the delivery sheath opening to collapse the compressor, wherein collapse of the compressor upon reception within the delivery sheath exerts a radial force upon the ED sufficient to compress the ED into the compressed position for reception in the delivery sheath. The kit further comprises a compressor support for providing lateral support for an exterior surface of the compressor as it is urged proximally through the delivery sheath opening, the compressor support comprising a body comprising an interior wall defining an insertion bore for receiving the compressor and ED within the body, the insertion bore having a generally frustoconical shape that tapers between a broad distal opening of the body through which the compressor and ED are received within the insertion bore in the non-compressed position and a narrower proximal opening of the body configured for communication with the delivery sheath opening. The interior wall of the body is configured to provide lateral support to the exterior surface of the compressor as the compressor is urged proximally through the proximal opening of the body and into the delivery sheath through delivery sheath opening.

In various embodiments, the compressor support further comprises a first tubular portion defining an interior space of the first tubular portion in communication with the insertion bore of the body, the first tubular portion comprising distal and proximal first tubular portion ends. The distal first tubular portion end is proximal to the proximal opening of the body, wherein the tubular structure has a width larger than the diameter of the delivery sheath.

In various embodiments, the compressor support further comprises a second tubular portion defining an interior space of the second tubular portion in communication with the insertion bore of the body, the second tubular portion comprising distal and proximal second tubular portion ends. The proximal second tubular portion end is proximal to the distal opening of the body, wherein the tubular structure has a length and width sized to receive the ED in the non-compressed position.

In various embodiments, the kit further comprises a push wire detachably attached to the ED and disposed within the delivery sheath. The push wire is also disposed within the ED though the proximal compressor opening and through the proximal opening of the body.

In various embodiments, the kit further comprises an end cap sized to be received in the distal second tubular portion end. The end cap comprises a push wire opening therethrough, wherein the push wire is also disposed through the push wire opening.

Various aspects of the disclosure relate to a system for the radial compression of a reversibly compressible endovascular device (ED) prior to deployment, the system comprising: the ED, wherein the ED comprises a tubular body, wherein the body is expandable between a compressed position and a non-compressed position, the tubular body having an inner surface, an outer surface, opposed distal and proximal ED ends, and opposed distal and proximal ED openings; a delivery sheath sized to receive and maintain the ED in the compressed position, the delivery sheath having a delivery sheath opening having a diameter sized to receive the ED into the delivery sheath in a compressed form; a collapsible compressor for compressing the ED for reception by the delivery sheath through the delivery sheath opening, wherein the compressor comprises a generally tapered structure defining an interior space, the tapered structure comprising distal and proximal compressor ends, wherein the proximal compressor end is proximal to the delivery sheath opening, wherein the distal compressor end comprises a distal compressor opening sized to receive the ED in the non-compressed position, wherein the tapered structure tapers from the distal compressor opening toward the proximal compressor end such that the cross section of the interior space diminishes toward the proximal compressor end, wherein the cross sectional area of the interior space at the proximal compressor end is equal to or less than the cross sectional area of the delivery sheath opening, and wherein an interior surface of the tapered structure is frictionally engaged with the outer surface of the ED; a hollow compressor tube attached to the compressor and disposed within the delivery sheath, wherein the hollow compressor tube is operable to be advanced proximally through the delivery sheath to urge the compressor and the ED frictionally engaged therein through the delivery sheath opening to collapse the compressor, wherein collapse of the compressor upon reception within the delivery sheath exerts a radial force upon the ED sufficient to compress the ED into the compressed position for reception in the delivery sheath; and—a push wire disposed within the hollow compressor tube and operable to be advanced through the delivery sheath independently of the hollow compressor tube, wherein the push wire has a bump member disposed thereon proximal to the proximal ED end, wherein the bump member comprises a circular contact surface having a diameter sized to contact the ED at the proximal ED end about a circumference of the proximal ED end of the ED in the compressed position, the bump member being configured so that a distal face of the bump member contacts the ED at the proximal ED end, wherein the bump member is not required to be engaged with the ED during compression by the collapsible compressor, and wherein the bump member is configured to be advanced distally relative to the tapered structure in order for the contact surface to contact the proximal ED end and apply a distal force at the proximal ED end about the circumference of the proximal ED end only in a distal direction in order for the ED to be disengaged from the compressor.

BRIEF DESCRIPTION OF THE DRAWINGS

In drawings which illustrate embodiments of the invention.

DEFINITIONS

"Bioabsorbable", "biodegradable", and "bioresorbable" are used herein synonymously to refer to a material or structure that degrades or dissolves in living tissues or systems of a body over time.

"Endovascular device" as used herein refers to a prosthesis that can be implanted within a body lumen or body conduit.

"Comprising", "including", and "involving", as used herein mean "including, but not limited to".

"Consisting" as used herein means "including and limited to".

"Proximal", as used herein with respect to the features of the systems of the present disclosure, refers to a feature closer to an operator of the system.

"Distal", as used herein with respect to the features of the systems of the present disclosure, refers to a feature away from the an operator of the system.

"Lumen" as used herein refers to the cavity defined by a tubular structure of a mammalian body including, but not limited to, a blood vessel, a ureter, a urethra, a bile duct.

"Resiliently deformable" as used herein pertains to an object that is capable of autonomously returning to its original shape upon release from a bent, stretched, compressed, or otherwise deformed shape.

DETAILED DESCRIPTION

Rigid or Removable Compressors

This disclosure generally relates to implantable devices, and particularly systems and methods of compressing resiliently deformable endovascular devices in a surgical setting prior to deployment in a vessel of a body of a patient. Any term or expression not expressly defined herein shall have its commonly accepted definition understood by a person skilled in the art. To the extent that the following description is of a specific embodiment or a particular use of the invention, it is intended to be illustrative only, and not limiting of the invention, which should be given the broadest interpretation consistent with the description as a whole and with the claims.

Figure 1:
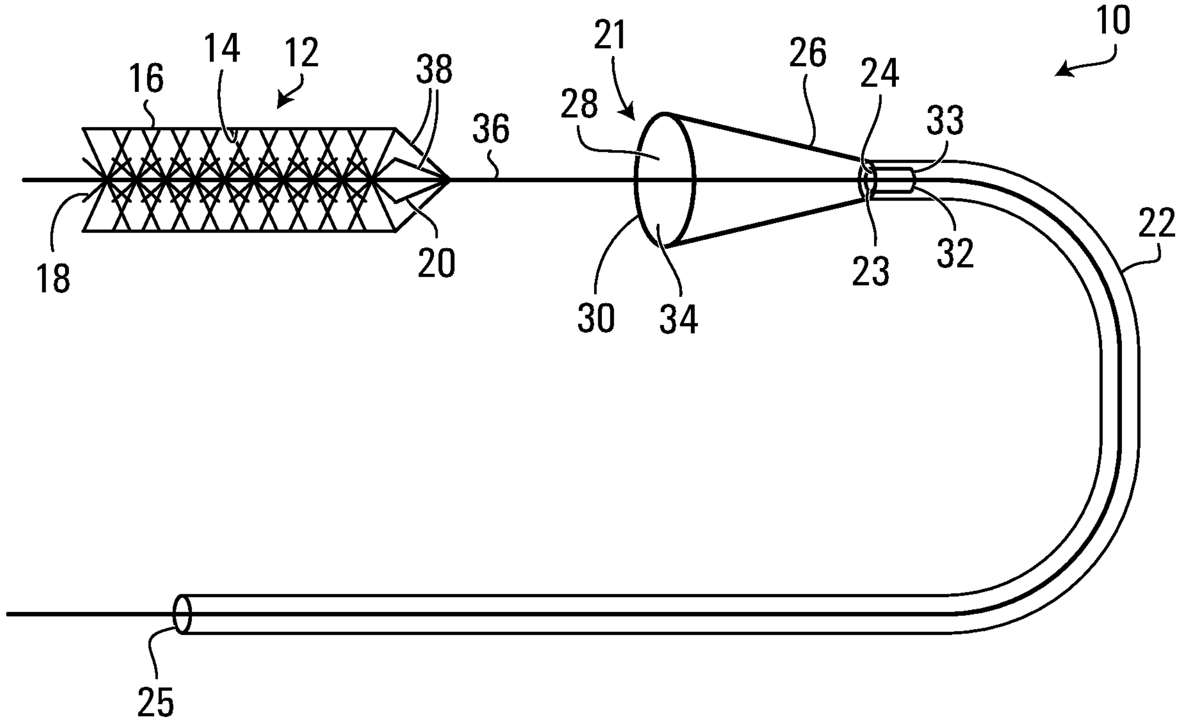
FIG. 1 is a drawing of a system for the radial compression of a reversibly compressible endovascular device prior to deployment according to a first embodiment of the invention.

Referring to FIG. 1, a system for the radial compression of a reversibly compressible endovascular device (ED) prior to deployment according to a first embodiment of the invention is shown generally at 10. The system includes a reversibly compressible ED shown generally at 12 as are generally known in the art. In general, the ED comprises a tubular body that is expandable between a non-compressed position, as depicted in FIG. 1, and a compressed position for loading within a catheter for delivery to a target site in the lumen of a vessel within the body of a subject. The tubular body has an inner surface 14, an outer surface 16, and opposed distal and proximal opposed ED openings 18 and 20.

The system further includes a delivery sheath 22 sized to receive and maintain ED 12 in the compressed position upon reception in the delivery sheath in the compressed position. Delivery sheath 22 has a distal delivery sheath end 23 having a delivery sheath opening 24. Delivery sheath opening 24 has a width sized to receive the ED 12 into delivery sheath 22 in a compressed form. Delivery sheath 22 further has a proximal delivery sheath end 25.

The system further includes a compressor shown generally at 21 for radially compressing the ED 12 for reception by the delivery sheath 22 through the delivery sheath opening 24. The compressor includes a generally tapered structure 26 defining an interior space 28. The tapered structure comprises distal and proximal compressor ends 30 and 32, wherein proximal end 32 is proximal to the delivery sheath opening 24.

Distal compressor end 30 comprises a distal compressor opening 34 sized to receive ED 12 in the non-compressed position. As illustrated in FIG. 1, tapered structure 26 tapers from distal compressor opening 34 toward proximal end 32 such that the radial cross section of interior space 28 diminishes from distal compressor end 30 toward proximal compressor end 32. Proximal compressor end 32 comprises a proximal compressor opening 33 in communication with delivery sheath opening 24. The width of proximal compressor opening 33 is less than the radial diameter of ED 12 when the ED is in the non-compressed position. The radial cross sectional area of interior space 28 proximal to the proximal compressor end 32, e.g. at proximal compressor opening 33, is equal to or less than the radial cross sectional area of delivery sheath opening 24. In this way, as ED 12 moves through tapered structure 26, it will be compressed to have a radial cross section less than the radial cross section of delivery sheath opening 24, such that ED 12 can be received within delivery sheath 22 in the compressed position. As such, ED 12, in a compressed form, can be urged through second compressor opening 33 and received within delivery sheath 22.

The system further comprises a push wire 36 that is detachably attached to ED 12. Push wire 36 is attached to ED 12 by at least one (i.e. one or more) threads 38. Threads 38 can be made of any suitable material for attaching the push wire to the ED, including metal wire. In FIG. 1, threads 38 are shown radiating from push wire 36 and attached to ED 12 at second ED opening 20. However, the skilled person understands that threads 38 may be attached to ED 12 at a different position, for example, to inner surface 14 or outer surface 16. In some embodiments, threads 38 could be attached at distal ED opening 18.

In some embodiments, the at least one thread is a single thread comprising a lasso, wherein the lasso is looped and tightened around the tubular body of the ED proximal to proximal ED opening to form a cincture about the proximal end of the ED.

Threads 38 may be electrolytically detachable from ED 12 once the ED is positioned at the target site within the lumen of the vessel, as is known in the field. Alternatively, threads 38 may be mechanically detachable from ED 12. It is within the purview of the skilled person to select an appropriate means of detaching threads 38 from the ED. In embodiments involving a lasso-style attachment, the loop of the lasso may be broken to release ED. The skilled person will understand that a variety of suitable detachment systems are available in the art as described in, for example, U.S. Pat. Nos. 10,405,868, 9,717,502, 10,182,931, and 9,814,466. Lasso-style mechanisms are known in the art as described, for example, by Pumar et al. (American Journal of Neuroradiology, 26: 2573-2577).

Threads 38 may be made of any suitable materials as are known in the field. For example, threads 38 may be made of metal wire.

As shown in FIG. 1, push wire 36 is disposed within delivery sheath 22 through delivery sheath opening 24. Push wire 36 further extends distally through proximal compressor opening 33, interior space 28, and distal compressor opening 34, to where it is attached to ED 12. Push wire 36 is operable to be advanced proximally through delivery sheath 22 to urge ED 12 through the compressor (i.e. tapered structure 26), whereby ED 12 is deformed into a compressed position as it is urged through the compressor from distal end 30 to proximal end 32, i.e. due to the progressively diminished cross sectional area of interior space 28, and further urged through proximal compressor opening 33 and delivery sheath opening 24 into delivery sheath 22 in a compressed position.

As shown in FIG. 1, push wire 36 may also be disposed within ED 12 through proximal ED opening 20.

A depicted in FIG. 1, tapered structure 26 may take the form of a funnel. In some embodiments, the width of proximal compressor end 32 is less than the width of delivery sheath opening 24 such that proximal compressor end 32 is sized to be received within delivery sheath 22 through delivery sheath opening 24. However, in alternative embodiments, the proximal compressor end may abut the delivery sheath end 23. The skilled person understands that the proximal compressor end and the delivery sheath end can be designed to cooperate in numerous different ways, and that it is only important that proximal compressor opening have a width equal to or less than the delivery sheath opening so that the ED will be in a sufficiently compressed position to be received within the delivery sheath as the ED approaches the proximal compressor end. In some embodiments, for example, the compressor may be integral with the delivery sheath, i.e. the compressor and delivery sheath are a single continuous unitary unit.

As depicted in FIG. 1, the tapered structure itself may have a unitary (i.e. one-piece) body. In some embodiments, such as depicted in FIG. 1, tapered structure 26 is removable once ED 12 has been received in a compressed position within delivery sheath 22

In operation, starting with ED 12 in an expanded position, retracting push wire 36 proximally into delivery sheath 22 toward proximal delivery sheath end 25 urges ED 12 into interior space 28 of tapered structure 26 through distal compressor opening 34, and toward proximal compressor end 32 to radially compress ED 12 to a compressed (i.e. unexpanded) position as the cross sectional area of interior space 28 diminishes from distal compressor end 30 toward proximal compressor end 32. Further retraction of push wire 36 toward proximal delivery sheath end 25 urges ED 12 in the compressed position through proximal compressor opening 33 and into delivery sheath 22.

Deployment

Once ED 12 has been received within delivery sheath 22 in a compressed position, the delivery sheath 22 can be used in conjunction with a delivery catheter for delivery of the ED to the target site.

Figure 2A:
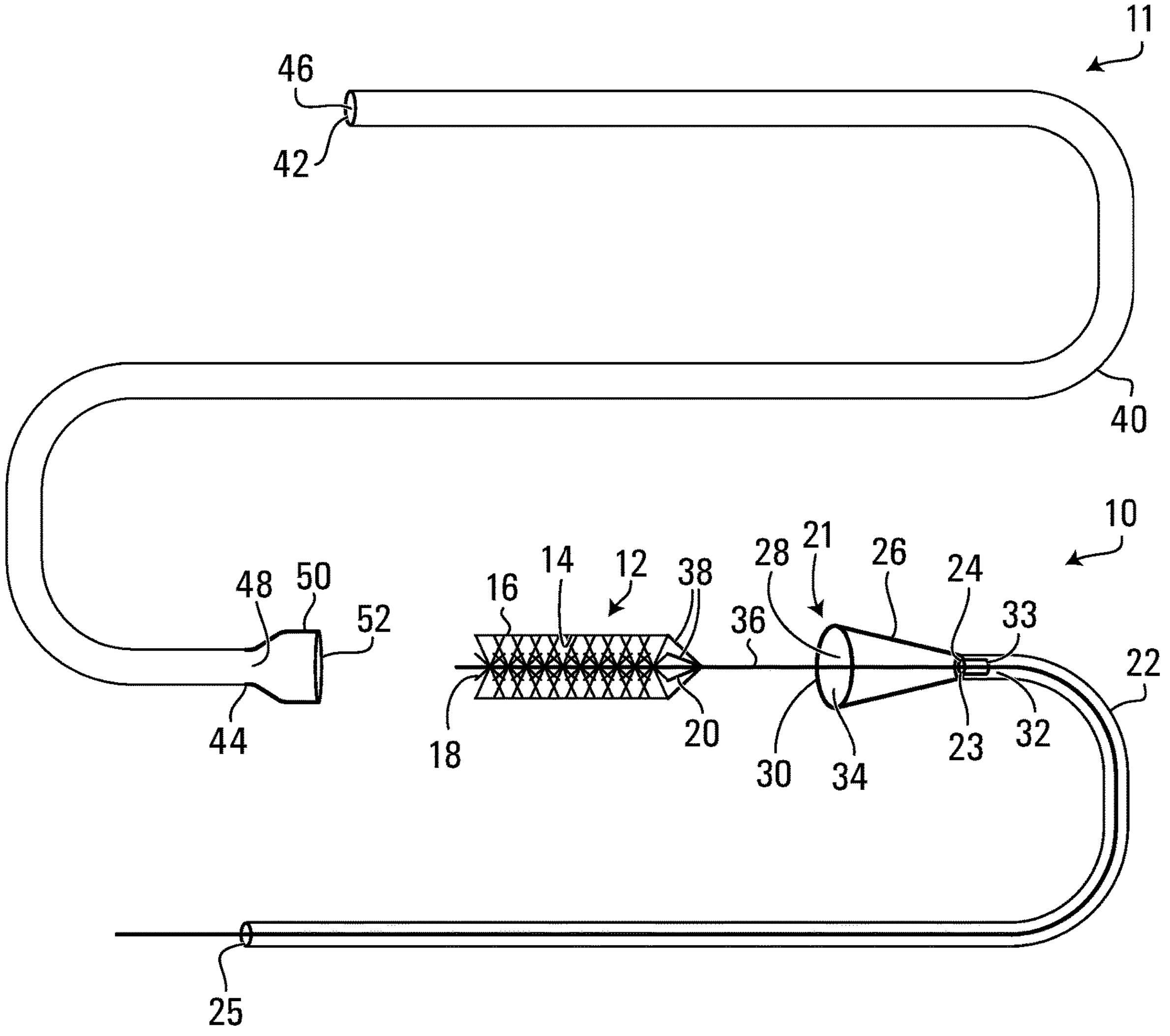
FIG. 2A is a drawing of a system for the deployment of a reversibly compressible endovascular device according to a first embodiment of the invention.
Figure 2B:
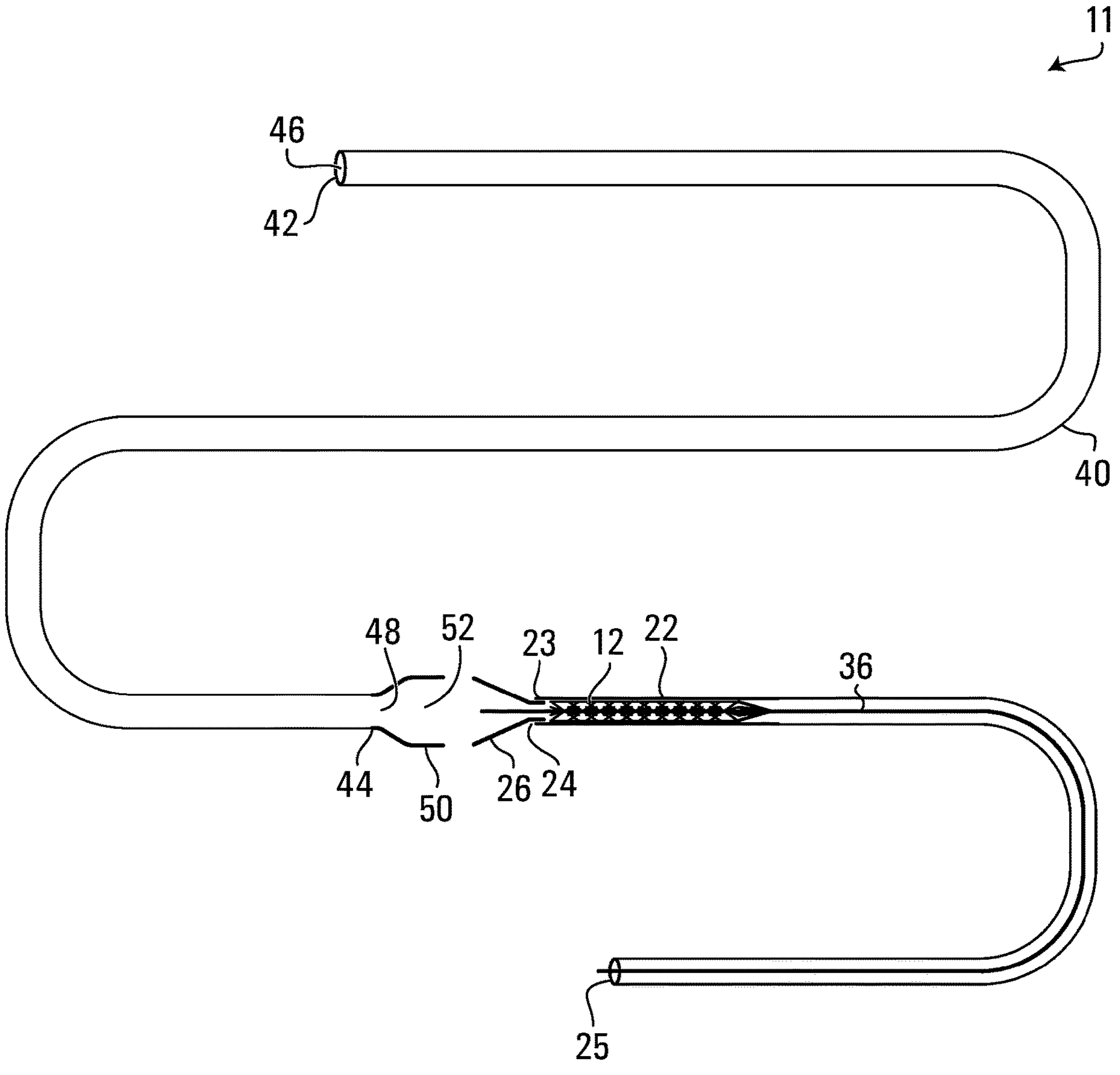
FIG. 2B is a drawing of a system for the deployment of a reversibly compressible endovascular device according to the embodiment illustrated in FIG. 2A, but with the endovascular device compressed within the delivery sheath.

Referring to FIGS. 2A and 2B, a system for deploying a reversibly compressible endovascular device within a lumen of a vessel is shown generally at 11. The system comprises a system for the radial compression of a reversibly compressible endovascular device (ED) prior to deployment as described above with reference to FIG. 1. The system further comprises a delivery catheter 40 having distal and proximal delivery catheter ends 42 and 44 having distal and proximal delivery catheter openings 46 and 48, respectively. Proximal delivery catheter opening 48 is for receiving ED 12 from delivery sheath 22 in a compressed position, whereas distal delivery catheter opening 46 is for deploying ED 12 into the lumen of the vessel. Accordingly, proximal end opening 48 is of a width equal to or greater than the width of delivery sheath opening 24.

The system further comprises a hub 50 connected to proximal delivery catheter end 44 and in communication with proximal delivery catheter opening 48. Hub 50 has hub opening 52 for receiving delivery sheath 22 in hub 50 when ED 12 is positioned within the delivery sheath. Hub 50 is for registering delivery sheath opening 24 in abutment with proximal delivery catheter opening 48.

Push wire 36 is operable to be advanced distally through delivery sheath 22 and delivery catheter 40 to urge ED 12 from the delivery sheath and into the delivery catheter through proximal delivery catheter opening 48, and through the delivery catheter distally toward and out distal catheter opening 46.

Figure 2C:
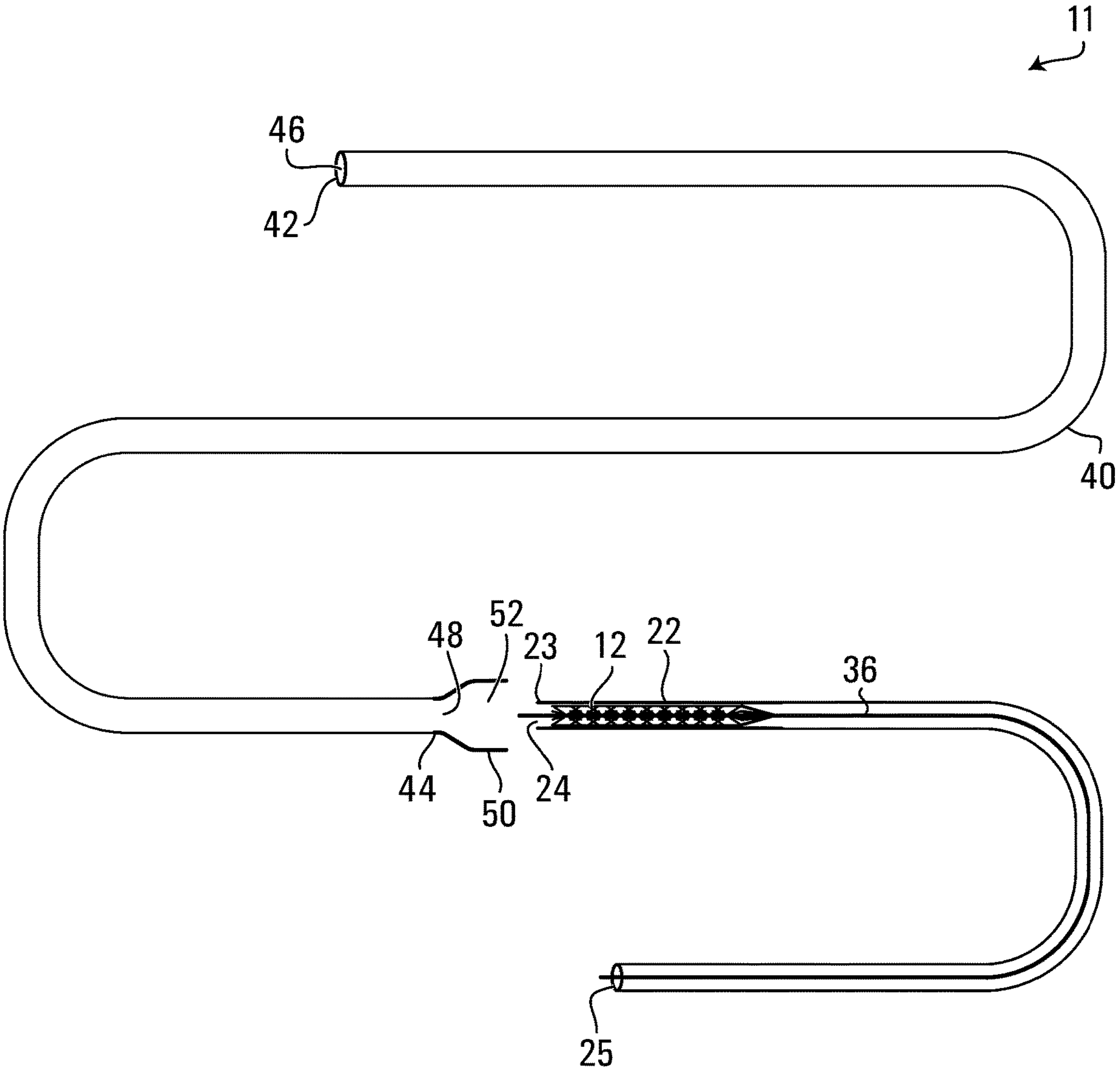
FIG. 2C is a drawing of a system for the deployment of a reversibly compressible endovascular device according to the embodiment illustrated in FIGS. 2A and 2B, but after the compressor has been removed.
Figure 2D:
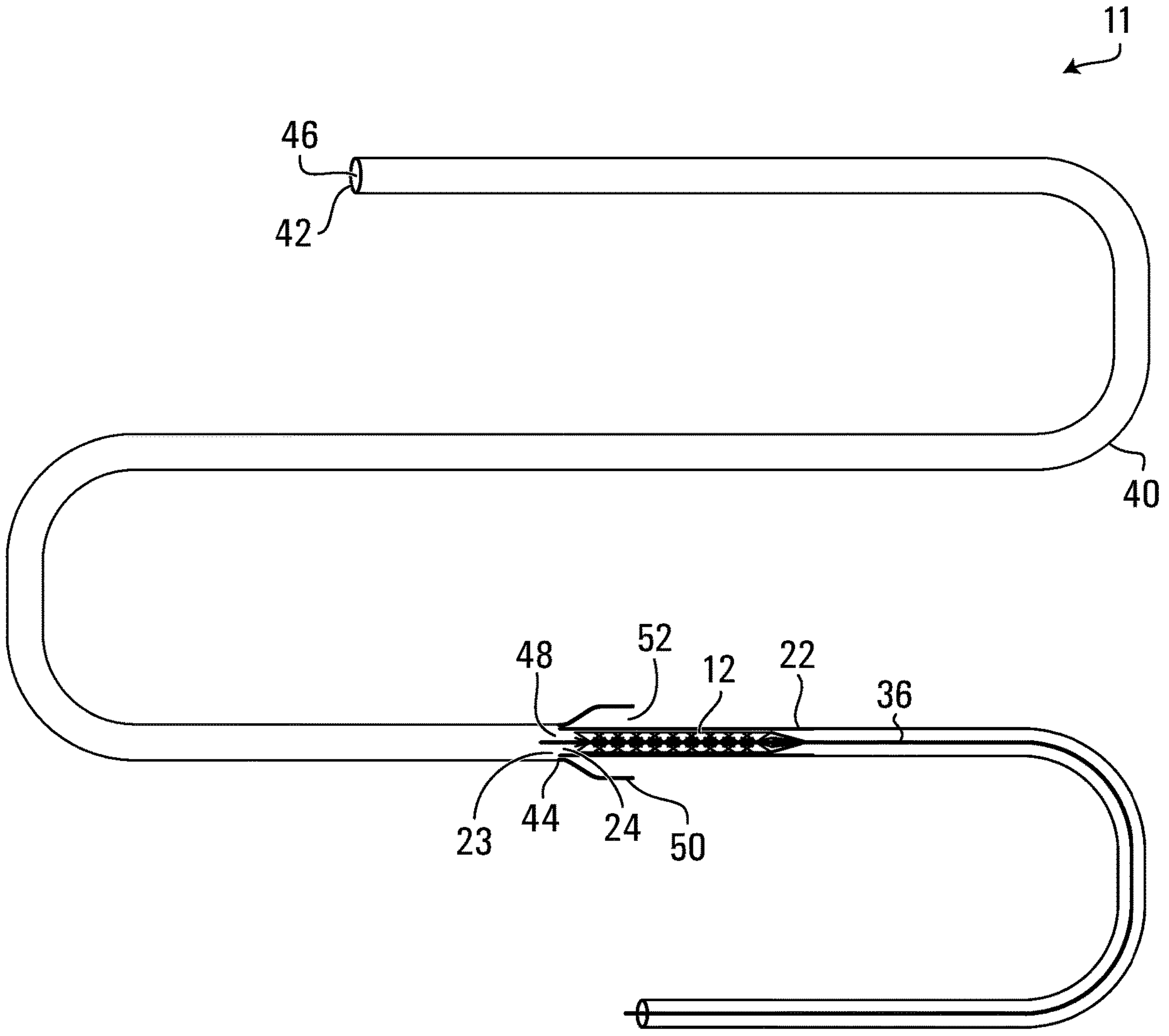
FIG. 2D is a drawing of a system for the deployment of a reversibly compressible endovascular device according to the embodiment illustrated in FIGS. 2A, 2B, and 2C, but with the delivery sheath registered with the delivery catheter prior to transfer of the compressed endovascular device from the delivery sheath to the delivery catheter.
Figure 2E:
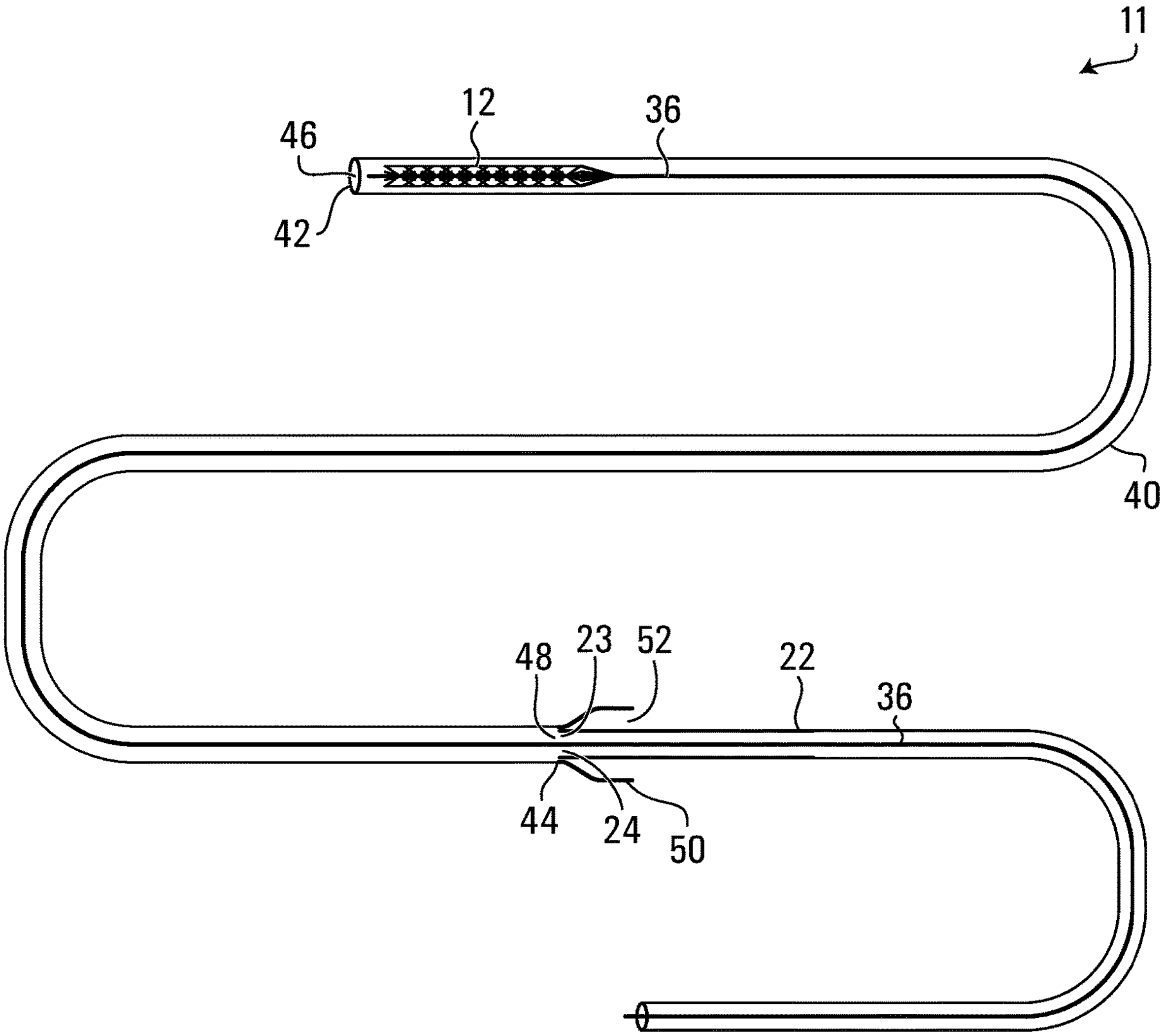
FIG. 2E is a drawing of a system for the deployment of a reversibly compressible endovascular device according to the embodiment illustrated in FIGS. 2A, 2B, 2C, and 2D, showing the compressed endovascular device advanced to the distal end of the delivery catheter prior to deployment at a target site within a lumen of a subject.
Figure 2F:
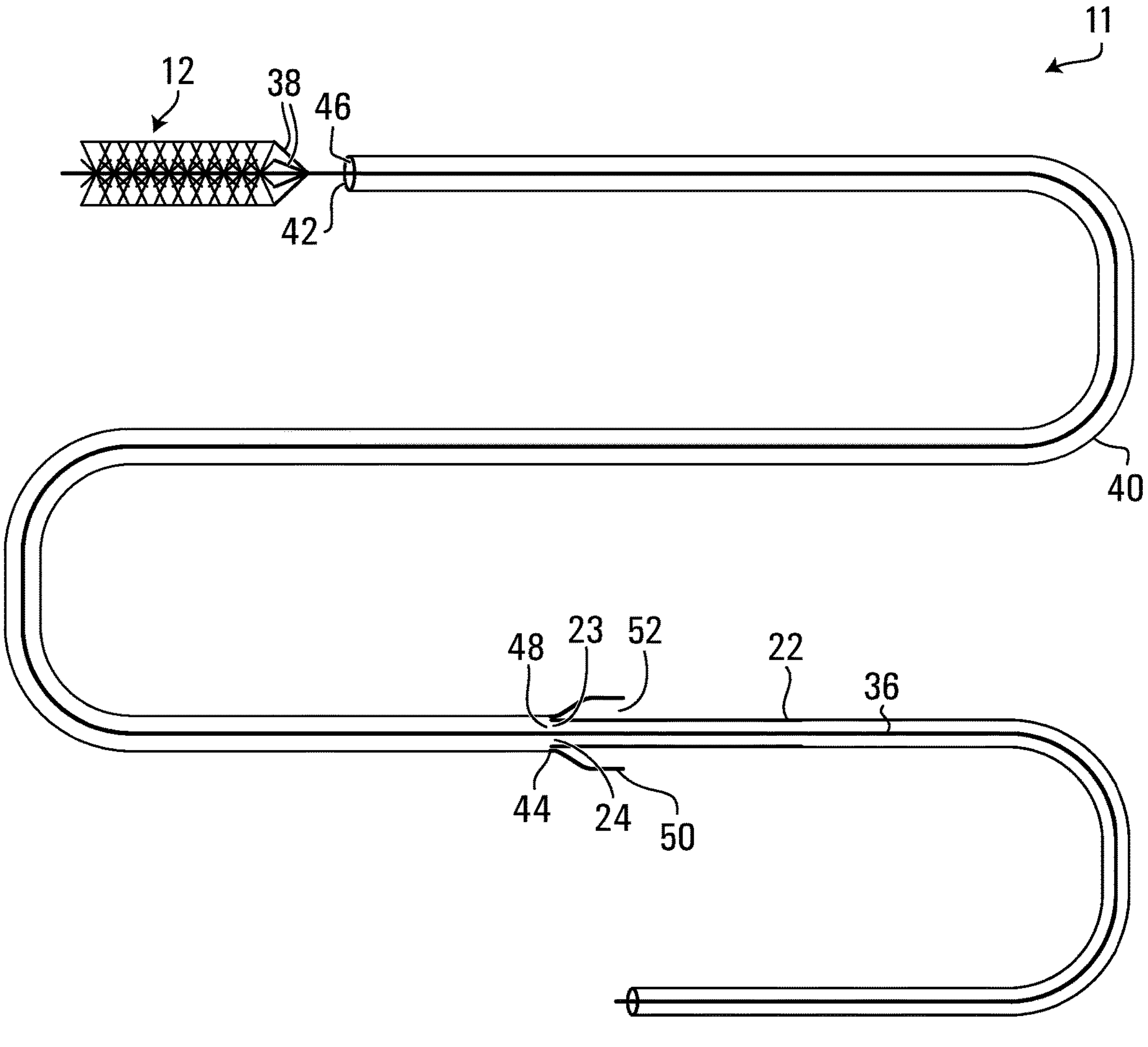
FIG. 2F is a drawing of a system for the deployment of a reversibly compressible endovascular device according to the embodiment illustrated in FIGS. 2A, 2B, 2C, 2D, and 2E showing the endovascular device advanced out of the distal opening of the delivery catheter and expanded at the target site within the lumen of a subject.

In operation, delivery catheter 40 will typically be deployed in a vessel of a subject, such that distal delivery catheter end 42 is positioned at a target site, with hub 50 remaining outside of the body of the subject. Referring to FIG. 2B, ED 12 is compressed and loaded in delivery sheath 22 as described above. Referring to FIG. 2C, tapered structure 26 may then be removed prior to engaging system 10 with delivery catheter 40. Referring to FIG. 2D, distal end 23 of delivery sheath 22, with ED 12 compressed within it, is then inserted in hub 50 through hub opening 52. Delivery sheath opening 24 is then registered with proximal delivery catheter opening 48. Referring to FIG. 2E, push wire 36 is then used to advance ED 12 distally through delivery sheath opening 24 into delivery catheter 40 through proximal delivery catheter opening 48, and then distally through the delivery catheter 40 toward distal delivery catheter opening 46. Referring to FIG. 2F, ED 12 is then advanced through distal delivery catheter opening 46 into the lumen of the vessel where it is expanded to its non-compressed position at the target site. Once ED 12 is in its non-compressed position at the target site, threads 38 can be detached from ED 12. Delivery catheter 40 may then be repositioned for the deployment of a further ED, or removed from the patient.

In embodiments where the ED is a self-expanding ED, expanding ED 12 in the lumen consists of simply allowing the ED to self-expand. Otherwise, it will be within the purview of a skilled person to select and employ an appropriate means of expanding an ED. For example, alternatives for expanding the ED may include inflating a balloon disposed within the tubular body of the ED to expand the ED.

Collapsible Compressors

Figure 3:
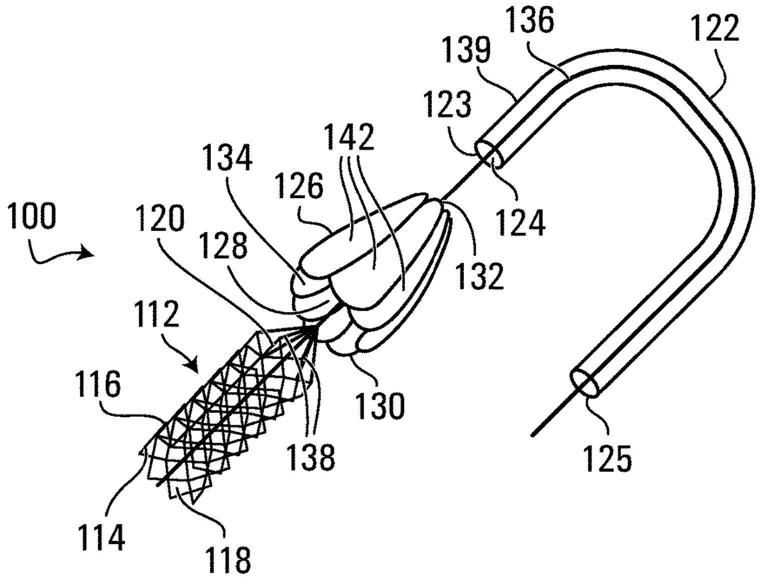
FIG. 3 is a is a drawing of a system for the radial compression of a reversibly compressible endovascular device prior to deployment according to a second embodiment of the invention involving a collapsible compressor.

Referring to FIG. 3, a system for the radial compression of a reversibly compressible endovascular device (ED) prior to deployment according to a second embodiment of the invention is shown generally at 100. The system includes a reversibly compressible ED 112 as are generally known in the art. In general, the ED comprises a tubular body that is expandable between a non-compressed position, as depicted in FIG. 3, and compressed position for loading within a delivery catheter for delivery to a target site in the lumen of a vessel within the body of a subject. The tubular body has an inner surface 114, an outer surface 116, and distal and proximal opposed ED openings 118 and 120.

The system further includes a delivery sheath 122 sized to receive and maintain the ED 112 in the compressed position upon reception in the delivery sheath in a compressed position. Delivery sheath 122 has a distal delivery sheath end 123 having a delivery sheath opening 124. Delivery sheath opening 124 has a width sized to receive the ED 112 into delivery sheath 122 in a compressed form. Delivery sheath 122 further has a proximal delivery sheath end 125.

The system further includes a compressor 126 for radially compressing the ED 112 for reception in the delivery sheath 122 through delivery sheath opening 124. The compressor includes a generally tapered structure defining an interior space 128 in which ED 112 initially may be at least partially positioned in a non-compressed position. Compressor 126 comprises distal and proximal compressor ends 130 and 132, wherein proximal end 132 is adjacent to delivery sheath opening 124.

Distal compressor end 130 comprises a distal compressor opening 134 sized to receive the ED 112 in the non-compressed position. As illustrated in FIG. 3, compressor 126 tapers from distal compressor opening 134 toward proximal compressor end 132 such that the radial cross section of the interior space 128 diminishes from distal compressor end 130 toward proximal compressor end 132. The width of compressor 126 at proximal compressor end 132 is less than the width of delivery sheath opening 124 such that proximal compressor end 132 is sized to be received within delivery sheath 122 through delivery sheath opening 124 as discussed below.

Compressor 126 is collapsible such that, as it collapses, the cross sectional area of interior space 128 at any position along the longitudinal axis of the compressor from distal compressor end 130 to proximal compressor end 132 progressively decreases. As the cross sectional area of interior space 128 decreases, compressor 126 exerts a radial force against ED 112 positioned therein to compress the ED.

Compressor 126 is sized such that, in a collapsed form, it is sized to be received within delivery sheath 122 through delivery sheath opening 124. ED 112, being compressed within interior space 128 as compressor 126 collapses, is thereby compressed for reception within delivery sheath 122.

The system further comprises a push wire 136 that is attached to proximal compressor end 132. Push wire 136 is also detachably attached to ED 112. Push wire 136 is attached to ED 112 by at least one (i.e. one or more) threads 138. In FIG. 3, threads 138 are shown radiating from push wire 136 and attached to ED 112 at proximal ED opening 120. However, the skilled person understands that threads 138 may be attached to ED 112 at a different position, for example, to inner surface 114 or outer surface 116. In some embodiments, threads 138 could be attached at distal ED opening 118.

The skilled person further understands that one or more threads 138 may attach ED 112 to compressor 126 rather than push wire 136. In some embodiments, the at least one thread is a single thread comprising a lasso, wherein the lasso is looped and tightened around the tubular body of the ED proximal to proximal ED opening to form a cincture about the proximal end of the ED.

As discussed above in respect of the first embodiment, threads 138 may be electrolytically or mechanically detachable from ED 112 once the ED is positioned at the target site within the lumen of the vessel, as is known in the field. In embodiments involving a lasso-style attachment, the loop of the lasso may be broken to release ED. Similarly, threads 138 may be made of any suitable materials as are known in the field.

Figure 4A:
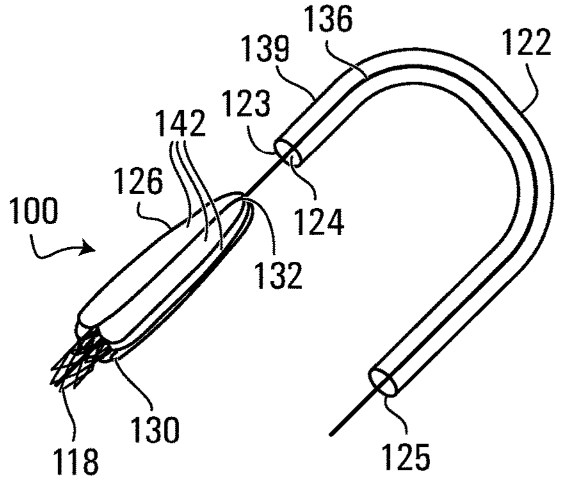
FIG. 4A is a drawing of a system for the radial compression of a reversibly compressible endovascular device prior to deployment according to a third embodiment of the invention involving a collapsible compressor that is frictionally engaged with the endovascular device.
Figure 4B:
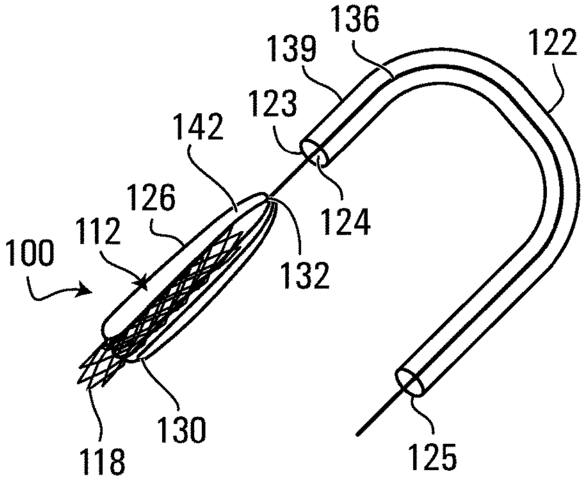
FIG. 4B is a drawing of a system for the radial compression of a reversibly compressible endovascular device prior to deployment according to the embodiment depicted in FIG. 4A, but with a couple of tongues removed to reveal the ED within.

Alternatively, referring to FIGS. 4A and 4B, ED 112 may not be connected to compressor 126 or push wire 136 by threads. Rather, compressor 126 may be sized and configured such that ED 112 is initially frictionally engaged with an interior surface of compressor 126. Accordingly, as compressor 126 is drawn into delivery sheath 122 through delivery sheath opening 124, ED 112 is drawn with it and compressed as compressor 126 collapses.

As shown in FIGS. 3, 4A, and 4B, push wire 136 is disposed within delivery sheath 122, and operable to be retracted proximally through delivery sheath 122 toward proximal delivery sheath end 125 to urge compressor 126 into delivery sheath 122 through delivery sheath opening 124. In various embodiments, an inner wall 139 of delivery sheath 122 is operable to exert a force against the outer surface of compressor 126 as compressor 126 is received within the delivery sheath, that is sufficient to collapse the tapered structure.

As shown in FIG. 3, push wire 136 may also be disposed within ED 112 through proximal ED opening 120.

A depicted in FIGS. 3, 4A, and 4B, compressor 126 may take the general form of a funnel. In some embodiments, as depicted in FIGS. 3, 4A, and 4B, the compressor 126 comprises a plurality of overlapping tongues 142 coupled at proximal compressor end 132, wherein each tongue 142 tapers toward the proximal compressor end. Each tongue 142 is slidable over an adjacent tongue to change the cross sectional area of the interior space along the longitudinal axis from distal compressor end 130 to proximal compressor end 132 as compressor 126 is drawn into delivery sheath 122 through delivery sheath opening 124.

However, the skilled person will understand that collapsible compressors according to the present disclosure could include a variety of radially compressible structures that, when at least partially received within the delivery sheath, form a tapered structure that can accommodate an ED in non compressed form and, as urged into the delivery sheath along with the ED, collapse to compress the ED to a compressed form. Such compressors could be formed of a braided structure, for example, a polypropylene braided structure or a metal braided structure as is known in the art and used in some cases for the fabrication of EDs themselves.

In various embodiments, compressor 126 is reversibly collapsible. For example, the tapered structure may be resiliently deformable such that, after reception in delivery sheath 122, it may be pushed out of delivery sheath 122 through delivery sheath opening 124 using push wire 136, into and through a delivery catheter, and out a distal delivery catheter opening (e.g. into the lumen of a vessel), at which time it will expand to a non-collapsed formation to permit release of ED 112 at the target site. Alternatively, the tapered structure may be actively expanded upon emergence from the delivery sheath, or deliver catheter as the case may be, by any means known in the art, e.g. using a balloon.

In operation, starting with ED 112 in an expanded position, retracting push wire 136 into delivery sheath 122 toward proximal delivery sheath end 125 urges compressor 126 into delivery sheath 122 through delivery sheath opening 124. As compressor 126 is urged into delivery sheath 122, the cross sectional area of interior space 128 at any position along the longitudinal axis of the compressor from distal compressor end 130 to proximal compressor end 132 is progressively reduced, wherein compressor 126 exerts a radial force against ED 112 positioned therein to radially compress the ED for reception within delivery sheath 122 through delivery sheath opening 124.

Deployment

Once ED 112 has been received within delivery sheath 122 in a compressed position, the delivery sheath 122 can be used in conjunction with a delivery catheter for delivery of the ED to the target site.

Figure 5A:
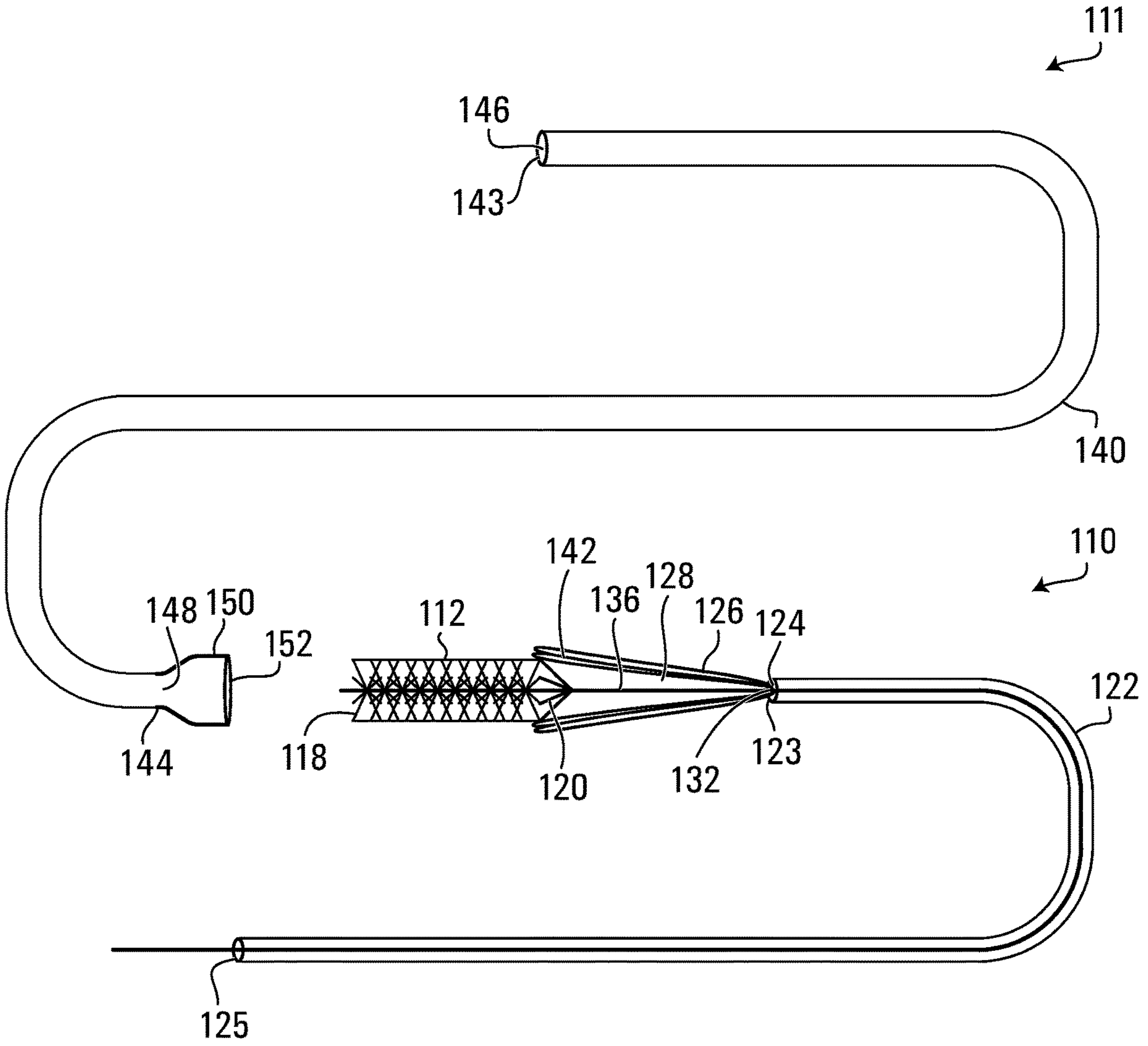
FIG. 5A is a drawing of a system for the deployment of a reversibly compressible endovascular device according to an embodiment of the invention involving a collapsible compressor as depicted in FIG. 3.
Figure 5B:
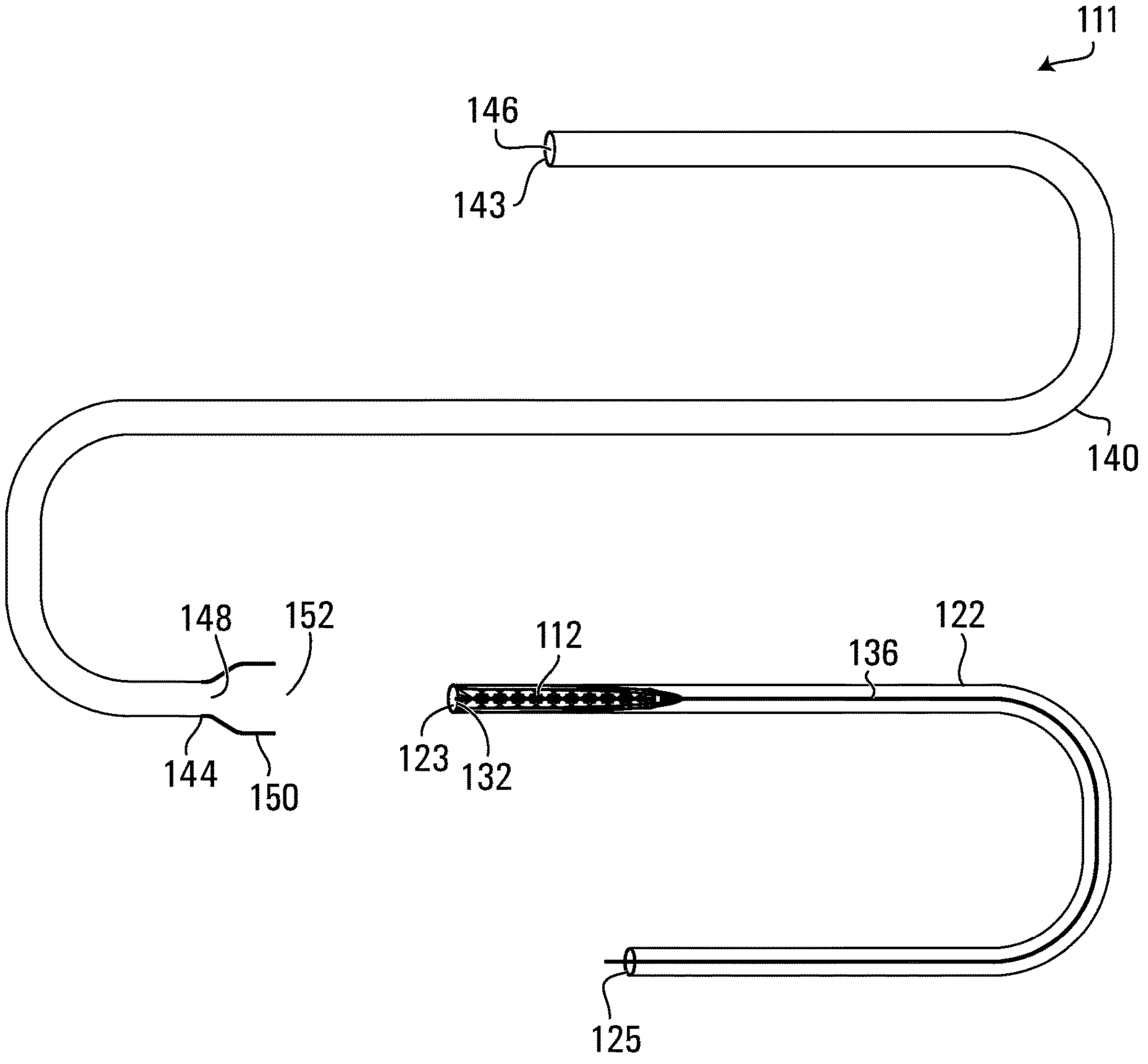
FIG. 5B is a drawing of a system for the deployment of a reversibly compressible endovascular device according to the embodiment illustrated in FIG. 5A, but with the endovascular device compressed within the delivery sheath.

Referring to FIGS. 5A and 5B, a system for deploying a reversibly compressible endovascular device within a lumen of a vessel is shown generally at 111. The system comprises a system for the radial compression of a reversibly compressible endovascular device (ED) prior to deployment as described above with reference to FIGS. 3, 4A, and 4B. The system further comprises a delivery catheter 140 having distal and proximal delivery catheter ends 143 and 144 having distal and proximal delivery catheter openings 146 and 148, respectively. Proximal delivery catheter opening 148 is for receiving ED 112 from delivery sheath 122 in a compressed position, whereas distal delivery catheter opening 146 is for deploying ED 112 into the lumen of the vessel. Accordingly, proximal delivery catheter opening 148 is of a width equal to or greater than the width of delivery sheath opening 124.

Figure 5C:
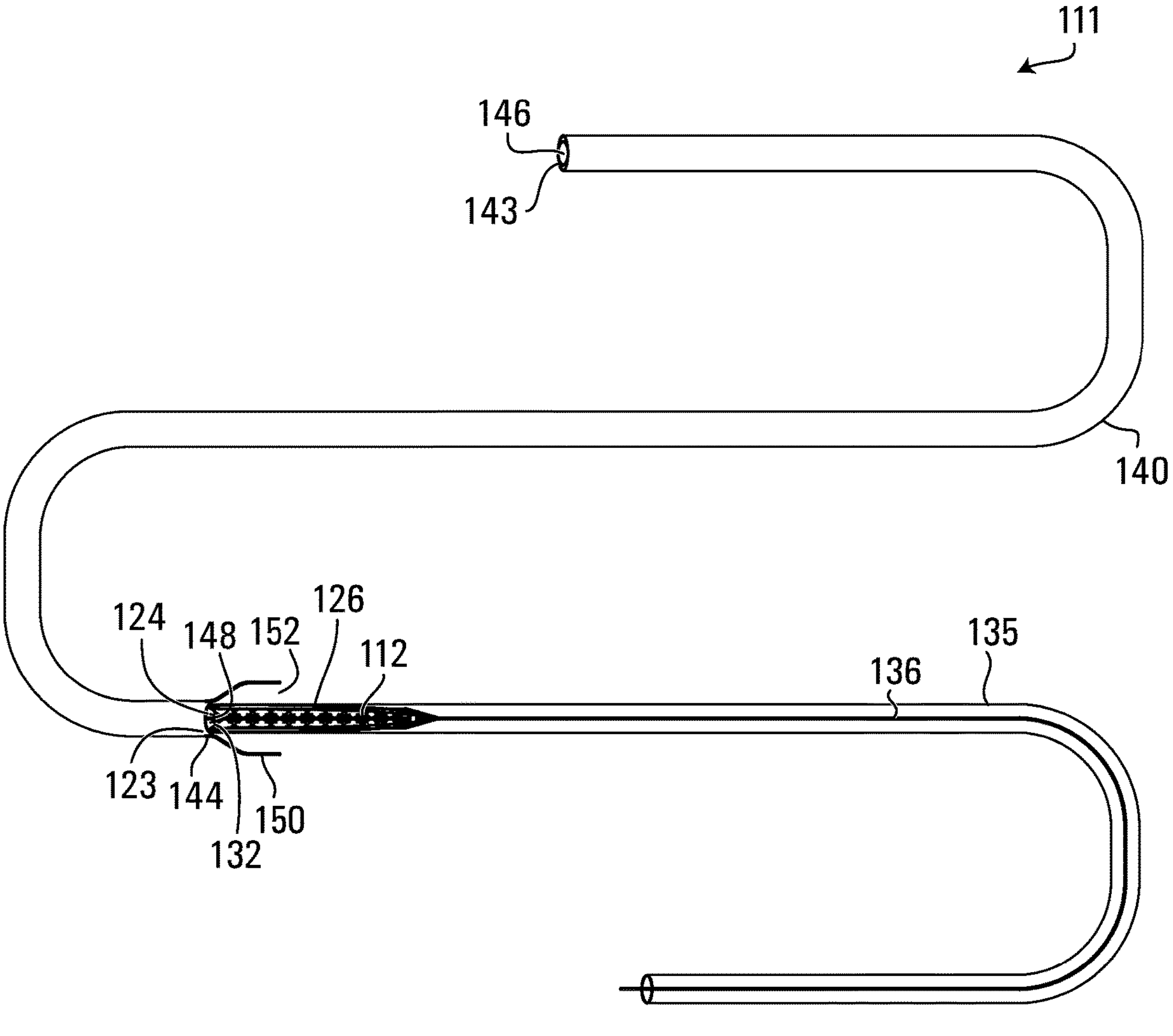
FIG. 5C is a drawing of a system for the deployment of a reversibly compressible endovascular device according to the embodiment illustrated in FIGS. 5A and 5B, but with the delivery sheath registered with the delivery catheter prior to transfer of the compressed endovascular device from the delivery sheath to the delivery catheter.

The system further comprises a hub 150 connected to proximal delivery catheter end 144 and in communication with proximal delivery catheter opening 148. Referring to FIG. 5C, hub 150 has hub opening 152 for receiving delivery sheath 122 in hub 150 when compressor 126 and ED 112 are positioned in the delivery sheath. Hub 150 is for positioning delivery sheath opening 124 in abutment with proximal delivery catheter opening 148.

Figure 5D:
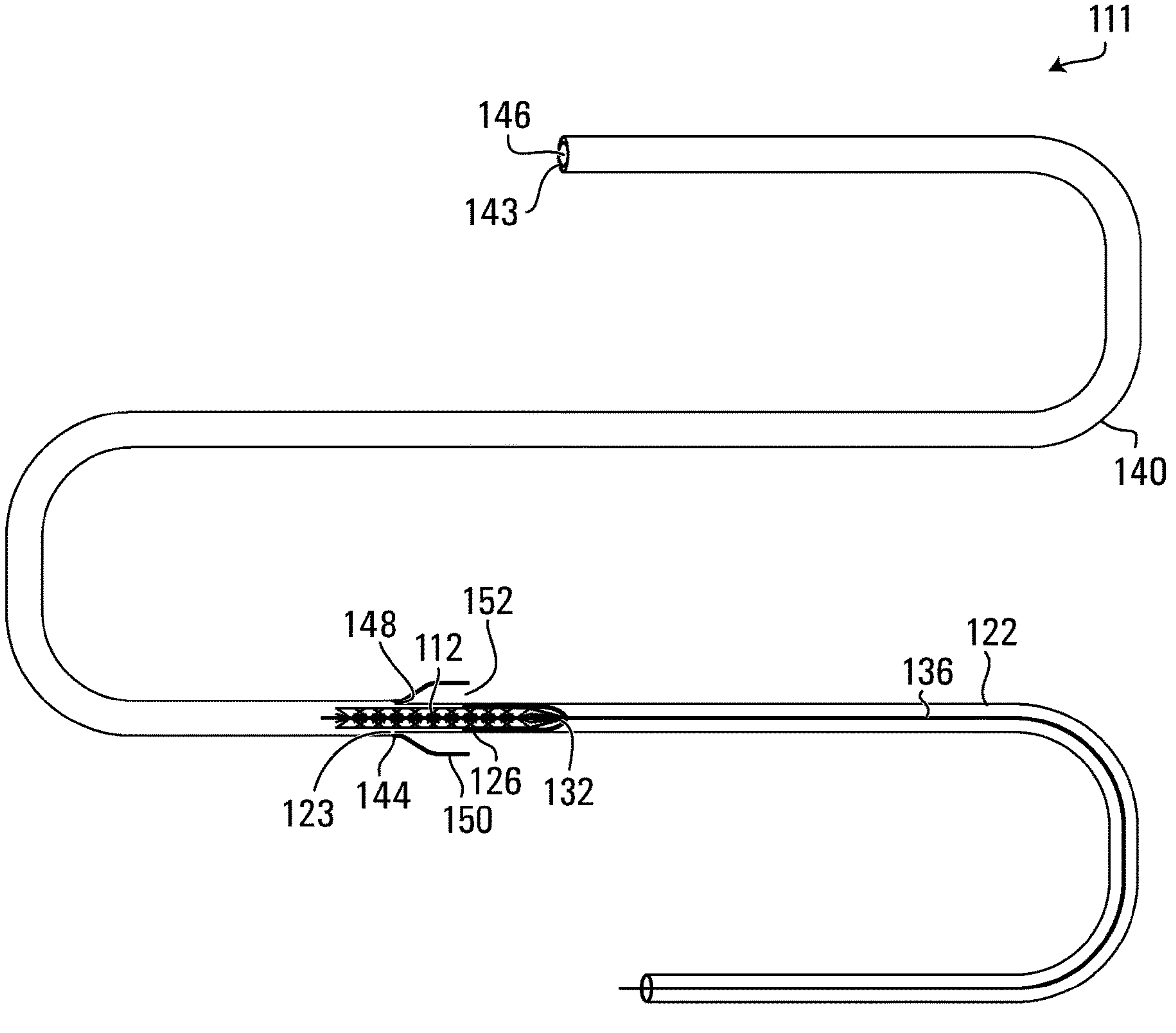
FIG. 5D is a drawing of a system for the deployment of a reversibly compressible endovascular device according to the embodiment illustrated in FIGS. 5A, 5B, and 5C, showing the compressed endovascular device and compressor advanced partially into the delivery catheter through the proximal delivery catheter opening.
Figure 5E:
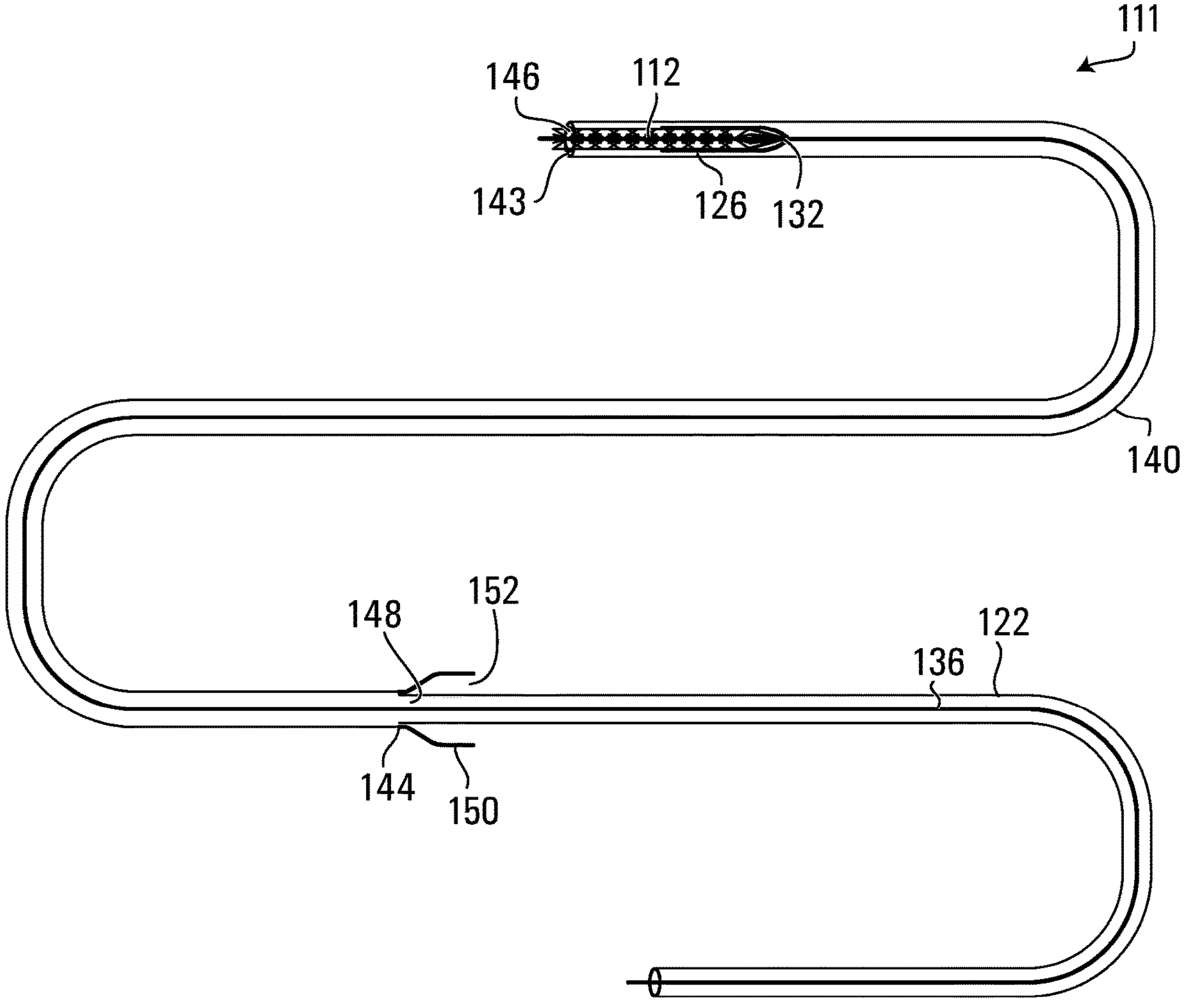
FIG. 5E is a drawing of a system for the deployment of a reversibly compressible endovascular device according to the embodiment illustrated in FIGS. 5A, 5B, 5C, and 5D, showing the compressed endovascular device and compressor advanced to the distal end of the delivery catheter prior to deployment at a target site within a lumen of a subject.
Figure 5F:
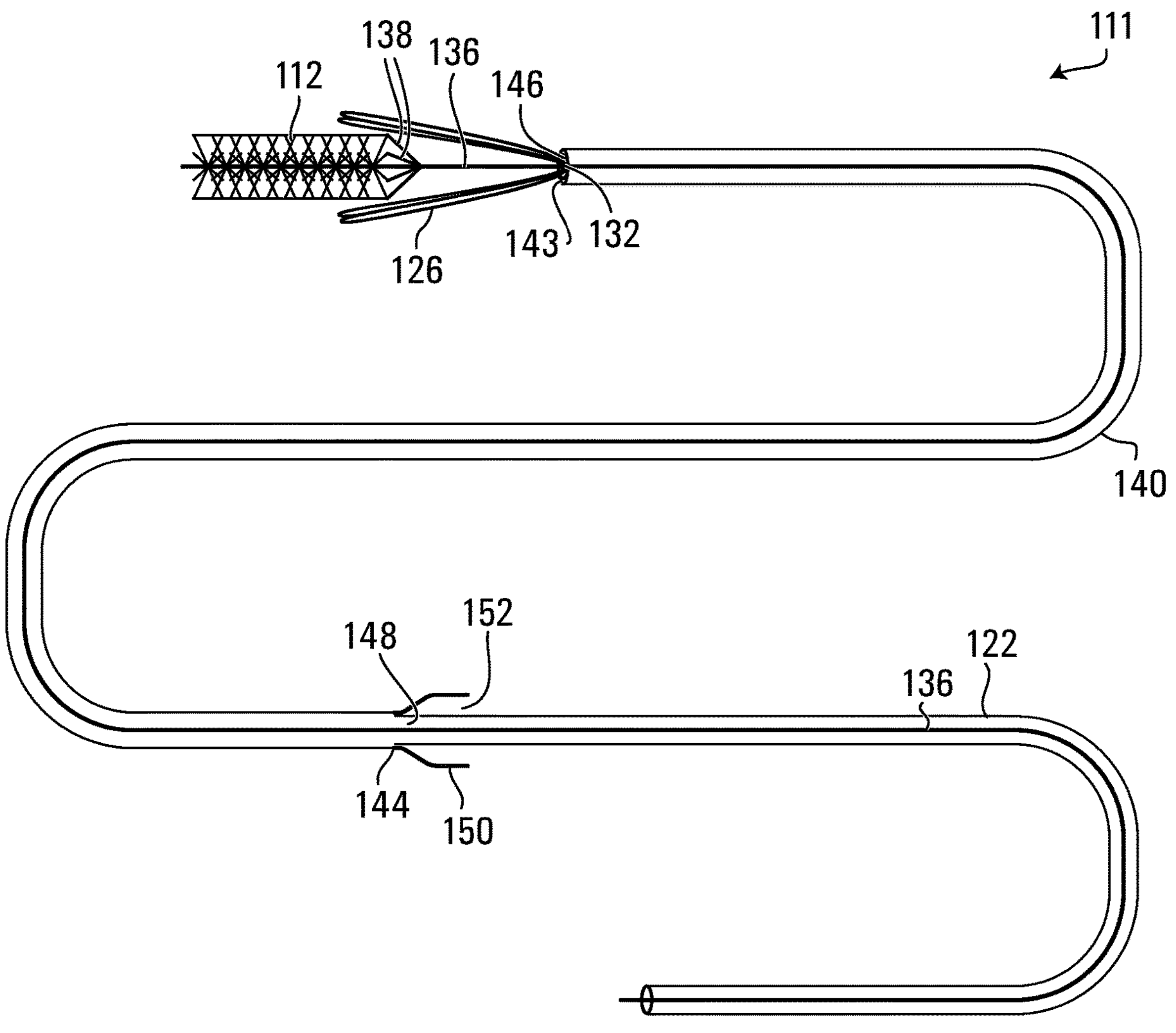
FIG. 5F is a drawing of a system for the deployment of a reversibly compressible endovascular device according to the embodiment illustrated in FIGS. 5A, 5B, 5C, 5D, and 5E showing the endovascular device and compressor advanced out of the distal delivery catheter opening of the delivery catheter and expanded at the target site within the lumen of a subject.
Figure 5G:
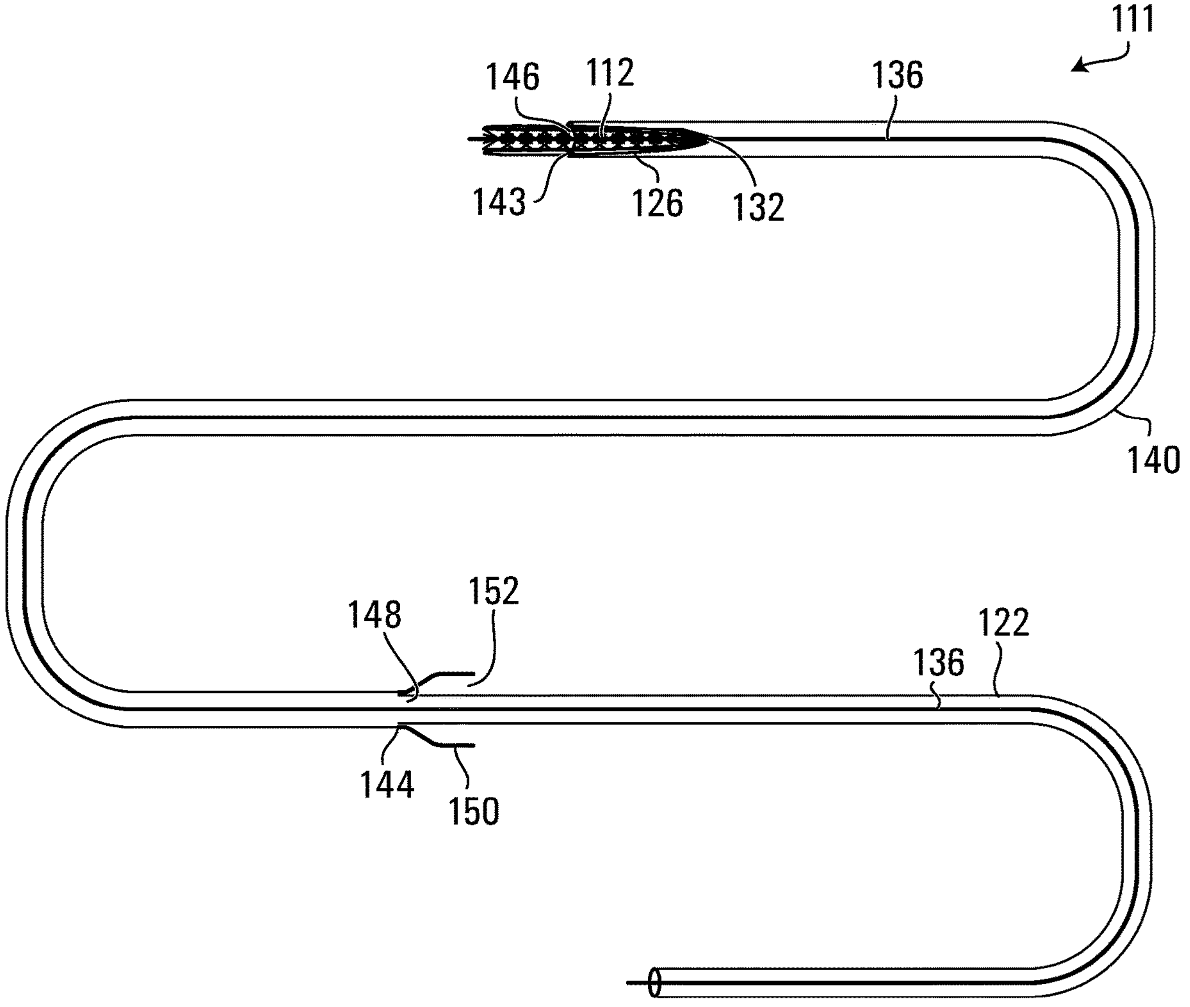
FIG. 5G is a drawing of a system for the deployment of a reversibly compressible endovascular device according to the embodiment illustrated in FIGS. 5A, 5B, 5C, 5D, 5E, and 5F showing the retraction of an initially deployed endovascular device and compressor into the delivery catheter through the distal delivery catheter opening.

Referring to FIGS. 5F and 5G push wire 136 is operable to be advanced distally through delivery sheath 122 and delivery catheter 140 to urge compressor 126 and ED 112 out from the delivery sheath through delivery sheath opening and into delivery catheter through proximal delivery catheter opening 148, and through the delivery catheter distally toward and out distal delivery catheter opening 146 into the lumen. Referring to FIG. 5F, once in the lumen at the target site and unconstrained by delivery catheter 140, compressor 126 may be expanded from its collapsed position. This, in turn, permits ED 112 to be expanded to its non-compressed position at the target site.

In embodiments where the compressor is a self-expanding compressor, expanding compressor 126 in the lumen involves allowing the compressor to self-expand. In embodiments where the ED is a self-expanding ED, expanding ED 112 in the lumen similarly involves allowing the ED to self-expand to a non-compressed position. It will be within the purview of a skilled person to select and employ an appropriate means of expanding a compressor or an ED. For example, alternatives for expanding the ED, and/or the compressor, may include inflating a balloon disposed within the tubular body of the ED to expand the ED.

Once in its non-compressed position at the target site, threads 138 may be detached from ED 112, and the delivery catheter may then be repositioned for the deployment of a further ED, or removed. Alternatively, if the embodiment relies on frictional engagement of the compressor with the ED as depicted in FIGS. 4B, then there is no need to detach any threads.

Alternatively, in embodiments employing threads, it may be desirable to reposition an ED before the threads are detached. In such embodiments, and referring to FIG. 5G push wire 136 is operable to be retracted proximally toward hub 150 to urge deployed ED 112 and expanded compressor 126 back toward the distal delivery catheter opening 146, wherein collapse of compressor 126 upon reception within delivery catheter 140, as with previous reception within delivery sheath 122, exerts a radial force upon ED 112 sufficient to compress the ED for reception in the delivery catheter.

In operation, delivery catheter 140 will typically be deployed in a vessel of a subject, such that distal delivery catheter end 143 is positioned at a target site, with hub 150 remaining outside of the body of the subject. ED 112 is loaded in delivery sheath 122 as described above with reference to FIGS. 3, 4A, and 4B. Referring to FIG. 5C, distal end 123 of delivery sheath 122, with ED 112 compressed within it, is then inserted in hub 150. Delivery sheath opening 124 is then registered with proximal delivery catheter opening 148. Referring to FIGS. 5D and 5E, push wire 136 is then used to advance compressor 126 and ED 112 distally through the delivery sheath opening 124 into delivery catheter 140 through proximal delivery catheter opening 148, and then distally through the delivery catheter toward distal delivery catheter opening 146. Referring to FIG. 5F, compressor 126 and ED 112 are then advanced through distal delivery catheter opening 146 into the lumen of the vessel where the compressor is expanded to its non-collapsed position. With the expansion of the compressor 126, ED 112 may be expanded in the lumen at the target site.

In embodiments where the ED is a self-expanding ED, expanding ED 112 in the lumen involves allowing the ED to self-expand. It will be within the purview of a skilled person to select and employ an appropriate means of expanding an ED. For example, alternatives for expanding the ED may include inflating a balloon disposed within the tubular body of the ED to expand the ED.

Referring to FIG. 5G, if repositioning of ED 112 is desired, push wire 136 is retracted proximally through delivery catheter 140 to urge reversibly collapsible compressor 126 back through distal delivery catheter opening 146 to collapse compressor 126. As with previous loading within delivery sheath 122, as compressor 126 collapses, it exerts a radial force upon ED 112 to compress the ED into a compressed position for reception in delivery catheter 140. Delivery catheter 140 is then repositioned to a second position at target site, or to a second target site. Push wire 136 is again advanced distally to urge compressor 126 and ED 112 out of delivery catheter 140 and into the lumen through distal delivery catheter opening 146. Once compressor 126 is outside of delivery catheter 140, it may again be expanded, thereby allowing ED 112 to be expanded at the second position. Once ED 112 has been satisfactorily positioned within the lumen, threads 138 (as depicted in FIG. 5F) may be detached.

The delivery catheter may then be repositioned for the deployment of a further ED, or removed.

Compressors Moveable Independently of Endovascular Devices

Figure 6A:
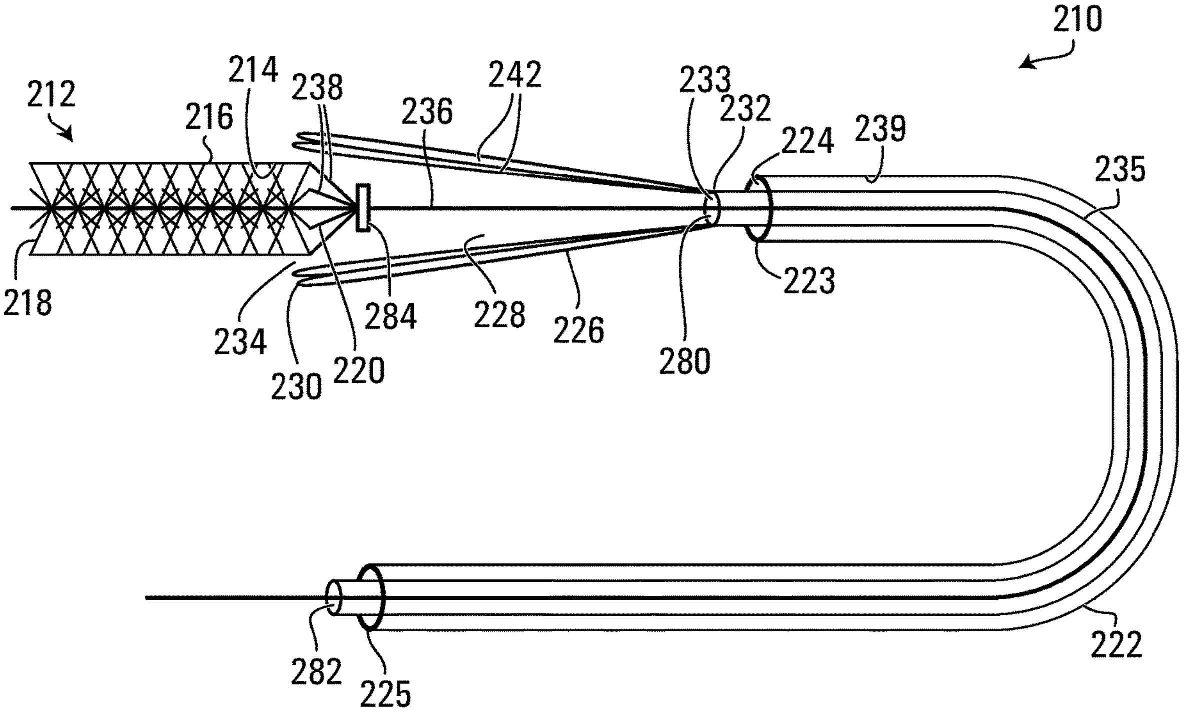
FIG. 6A is a drawing of a system for the radial compression of a reversibly compressible endovascular device prior to deployment according to a fourth embodiment of the invention involving a collapsible compressor that is moveable independent of the endovascular device.

Referring to FIG. 6A, a system for the radial compression of a reversibly compressible endovascular device (ED) prior to deployment according to a fourth embodiment of the invention is shown generally at 210. The system includes a reversibly compressible ED 212 as are generally known in the art. In general, the ED comprises a tubular body that is expandable between a non-compressed position, as depicted in FIG. 6A, and compressed position for loading within a catheter for delivery to a target site in the lumen of a vessel within the body of a subject. The tubular body has an inner surface 214, an outer surface 216, and opposed distal and proximal ED openings 218 and 220.

The system further includes a delivery sheath 222 sized to receive and maintain the ED 212 in the compressed position upon reception in the delivery sheath 222 in the compressed position. Delivery sheath 222 has a distal delivery sheath end 223 having a delivery sheath opening 224. Delivery sheath opening 224 has a width sized to receive the ED 212 into delivery sheath 222 in a compressed form. Delivery sheath 222 further has a proximal delivery sheath end 225.

The system further includes a compressor 226 for radially compressing the ED 212 for reception by the delivery sheath 222 through the delivery sheath opening 224. The compressor includes a generally tapered structure defining an interior space 228 in which ED 212 initially is at least partially positioned in a non-compressed position. The tapered structure comprises distal and proximal compressor ends 230 and 232.

Distal compressor end 230 comprises a distal compressor opening 234 sized to receive ED 212 in the non-compressed position. As illustrated in FIG. 6A, compressor 226 tapers from distal compressor opening 234 toward proximal compressor end 232 such that the radial cross section of the interior space 228 diminishes from distal compressor end 230 toward proximal compressor end 232. The width of proximal compressor end 232 is less than the width of delivery sheath opening 224 such that proximal compressor end 232 is sized to be received within delivery sheath 222 as discussed below.

Compressor 226 is collapsible, such that as it collapses, the cross sectional area of interior space 228 at any position along the longitudinal axis of the compressor from distal compressor end 230 to proximal compressor end 232 progressively decreases. As the cross sectional area of interior space 228 decreases, compressor 226 exerts a radial force against ED 212 positioned therein to compress the ED.

Compressor 226 is sized to be received, in collapsed form, within delivery sheath 222 through delivery sheath opening 224. ED 212, being compressed within interior space 228 as compressor 226 collapses, is thereby compressed for reception within delivery sheath 222.

The system further comprises means for urging compressor 226 and ED 212 proximally toward distal delivery sheath end 223 and into delivery sheath 222 through delivery sheath opening 224. The means for urging the compressor and the ED 212 proximally (or distally as the case may be) may further comprise independent means for urging the ED independently of the compressor.

Referring still to FIG. 6A, the means for urging compressor 226 and ED 212 according to this particular embodiment include a compressor wire 235 that is attached to proximal compressor end 232, which may be drawn proximally toward proximal delivery sheath end 225 to urge compressor 226 toward distal delivery sheath end 223. In this embodiment, compressor wire 235 is a hollow, tubular wire having distal and proximal compressor wire openings 280 and 282. Distal compressor wire opening 280 is in communication with a proximal compressor opening 233 at proximal compressor end 232.

In the embodiment illustrated in FIG. 6A, the means for urging compressor 226 and ED 212 further comprises a push wire 236 that is attached to the ED, but is not attached to the compressor. Push wire 236 is positioned within compressor wire 235 and extends through distal compressor wire opening 280 and proximal compressor opening 233, and is detachably attached to ED 212. Push wire 236 is attached to ED 212 by at least one (i.e. one or more) threads 238. In FIG. 6A, threads 238 are shown radiating from push wire 236 and attached to ED 212 at proximal ED opening 220. However, the skilled person understands that threads 238 may be attached to ED 212 at a different position, for example, to inner surface 214 or outer surface 216. In some embodiments, threads 238 could be attached at distal ED opening 218. In some embodiments, the at least one thread is a single thread comprising a lasso, wherein the lasso is looped and tightened around the tubular body of the ED proximal to proximal ED opening to form a cincture about the proximal end of the ED.

As discussed above in respect of the first and second embodiments, threads 238 may be electrolytically or mechanically detachable from ED 212 once the ED is positioned at the target site within the lumen of the vessel, as is known in the field. In embodiments involving a lasso-style attachment, the loop of the lasso may be broken to release ED. Threads 238 may be made of any suitable materials as are known in the field, including wires.

Thus, the skilled person will understand that compressor wire 235 and push wire 236 allow for the compressor 226 and the ED 212 to be moved independently of each other. For example, as described below, in situations where it is not desirable to deploy the compressor 226 into the lumen of vessel at the target site, push wire 236 may be advanced distally while compressor wire 235 is maintained in position or advanced proximally.

Referring again to FIG. 6A, the means for urging ED 212 further comprise a bump member 284 disposed on push wire 236 between threads 238 and proximal compressor opening 233. When compressor wire 235 is held in a static position, or retracted proximally through delivery sheath 222, while push wire 236 is advanced distally, bump member 284 abuts the proximal end of ED 212 at ED opening 220 to apply a force uniformly across the circumference of the ED 212 at the proximal end opening to urge the ED distally while the compressor 226 remains in position or is retracted proximally. In this way, ED 212 may be disengaged from the compressor 226.

In the illustrated embodiment, the bump member abuts the proximal end of ED 212 to urge the ED distally as push wire 236 is advance distally. However, the skilled person will understand that the bump member could be positioned at least partially within the ED through the proximal ED opening, such that a radially outer surface of the bump member can engage, e.g. frictionally engage, the inner surface of the ED, e.g. inner surface 214 of ED 212 to urge the ED distally as push wire 236 is advance distally. A skilled person will appreciate that a number of bumper structures could be used in the context of the presently disclosed invention in combination with a push wire to urge an ED distally independently of a compressor. For example, the skilled person will be aware of bumps, including a dual function bump, as disclosed in U.S. Pat. No. 10,292,851. Alternatively, a stent bed as described in U.S. Pat. No. 10,555,824 could be used as a bumper in the context of the presently disclosed invention.

Figure 6B:
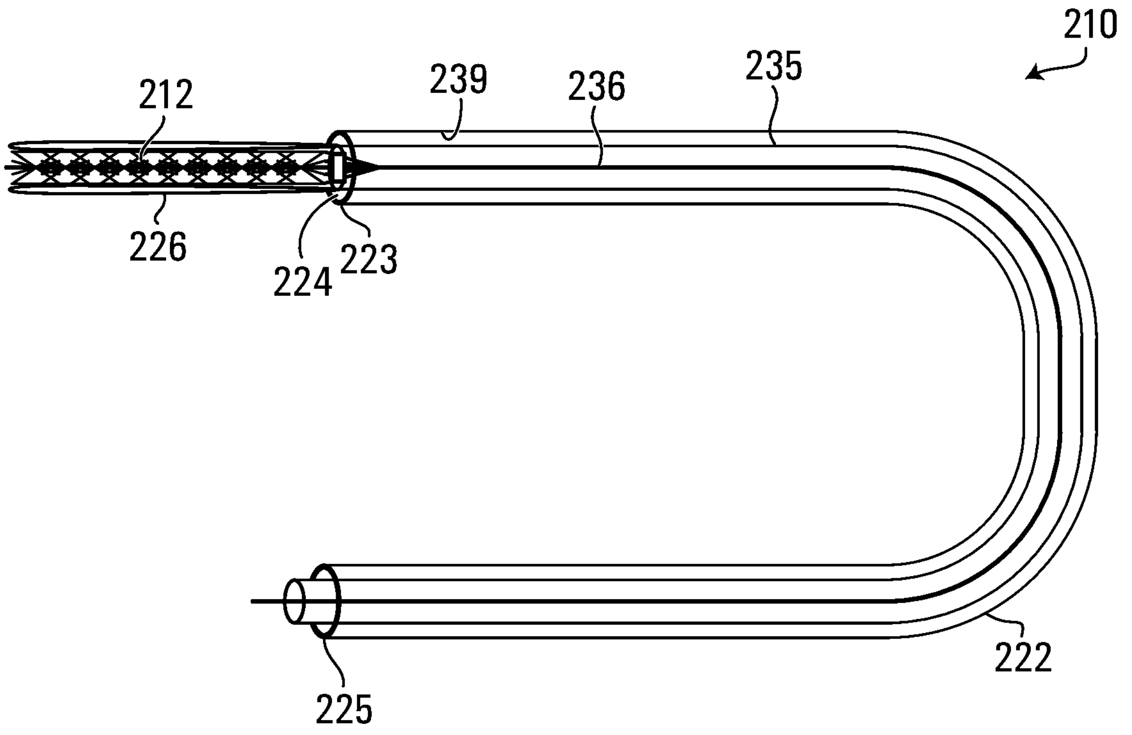
FIG. 6B is a drawing of the system depicted in FIG. 6A with the compressor and endovascular device partially received within the delivery sheath.

Referring to FIG. 6B, compressor wire 235 and push wire 236 are operable to be retracted proximally in conjunction through delivery sheath 222 toward proximal delivery sheath end 225 to urge compressor 226 into delivery sheath 222 through delivery sheath opening 224. In various embodiments, an inner wall 239 of delivery sheath 222 is operable to exert a force against the outer surface of compressor 226, as compressor 226 is received within the delivery sheath 222, that is sufficient to collapse the tapered structure.

As depicted in FIG. 6A, compressor 226 may take the general form of a funnel. In some embodiments, as depicted in FIG. 6A, compressor 226 comprises a plurality of overlapping tongues 242 coupled at proximal compressor end 232, wherein each tongue 242 tapers toward the proximal compressor end. Each tongue 242 is slidable over an adjacent tongue to change the cross sectional area of interior space 228 as the compressor 226 is collapsed or expanded.

However, the skilled person will again understand that collapsible compressors according to the present disclosure could include a variety of radially compressible structures that, when at least partially received within the delivery sheath, form a tapered structure that can accommodate an ED in noncompressed form and, as urged into the delivery sheath along with the ED, collapse to compress the ED to a compressed form. Such compressors could be formed of a braided structure, for example, a polypropylene braided or a metal braided structure as is known in the art and used in some cases for the fabrication of EDs themselves.

In various embodiments, compressor 226 is reversibly collapsible. For example, compressor 226 may be resiliently deformable such that, after reception in delivery sheath 222, it may be urged distally using compressor wire 235 from the delivery sheath into a delivery catheter, and then out of the delivery catheter through a distal delivery catheter opening (e.g. into the lumen of a vessel), at which time it will expand to a non-collapsed formation to permit release of ED 212 at the target site. Alternatively, the tapered structure may be actively expanded upon emergence from a delivery catheter opening by any means known in the art, e.g. using a balloon.

Alternatively, push wire 236 may be used to urge ED 212 distally independently of compressor 226, such that compressor 236 may remain in delivery sheath 222 (or delivery catheter, as the case may be) while ED 212 is advanced through a delivery catheter for deployment at a target site In operation, starting with ED 212 in an expanded position, retracting compressor wire 235 and push wire 236 into delivery sheath 222 toward proximal delivery sheath end 225 urges compressor 226 into delivery sheath 222 through delivery sheath opening 224. As tapered structure is urged into delivery sheath, the cross sectional area of interior space 228 at any position along the longitudinal axis of the compressor from distal compressor end 230 to proximal compressor end 232 is progressively reduced, wherein compressor 226 exerts a radial force against ED 212 positioned therein to radially compress the ED for reception within delivery sheath 222 through delivery sheath opening 224.

Deployment

Once ED 212 has been received within delivery sheath 222 in a compressed position, the delivery sheath 222 can be used in conjunction with a delivery catheter for delivery of the ED to the target site.

Referring to FIGS. 7A, 7B, 7C, and 7D, a system for deploying a reversibly compressible endovascular device within a lumen of a vessel is shown generally at 211. The system comprises a system for the radial compression of a reversibly compressible endovascular device (ED) prior to deployment as described above with reference to FIGS. 6A and 6B. The system further comprises a delivery catheter 240 having distal and proximal delivery catheter ends 243 and 244 having distal and proximal delivery catheter openings 246 and 248, respectively. Proximal delivery catheter opening 248 is for receiving ED 212 (and optionally compressor 226, as the case may be) from delivery sheath 222 in a compressed position, whereas distal delivery catheter opening 246 is for deploying ED 212 (and optionally compressor 226, as the case may be) into the lumen of the vessel. Accordingly, proximal delivery catheter opening 248 is of a width equal to or greater than the width of delivery sheath opening 224.

The system further comprises a hub 250 connected to proximal delivery catheter end 244 and in communication with proximal delivery catheter opening 248. Hub 250 has hub opening 252 for receiving delivery sheath 222 in hub 250 when compressor 226 and ED 212 are positioned in the delivery sheath. Hub 250 is for positioning delivery sheath opening 224 in abutment with proximal delivery catheter opening 248.

Figure 7A:
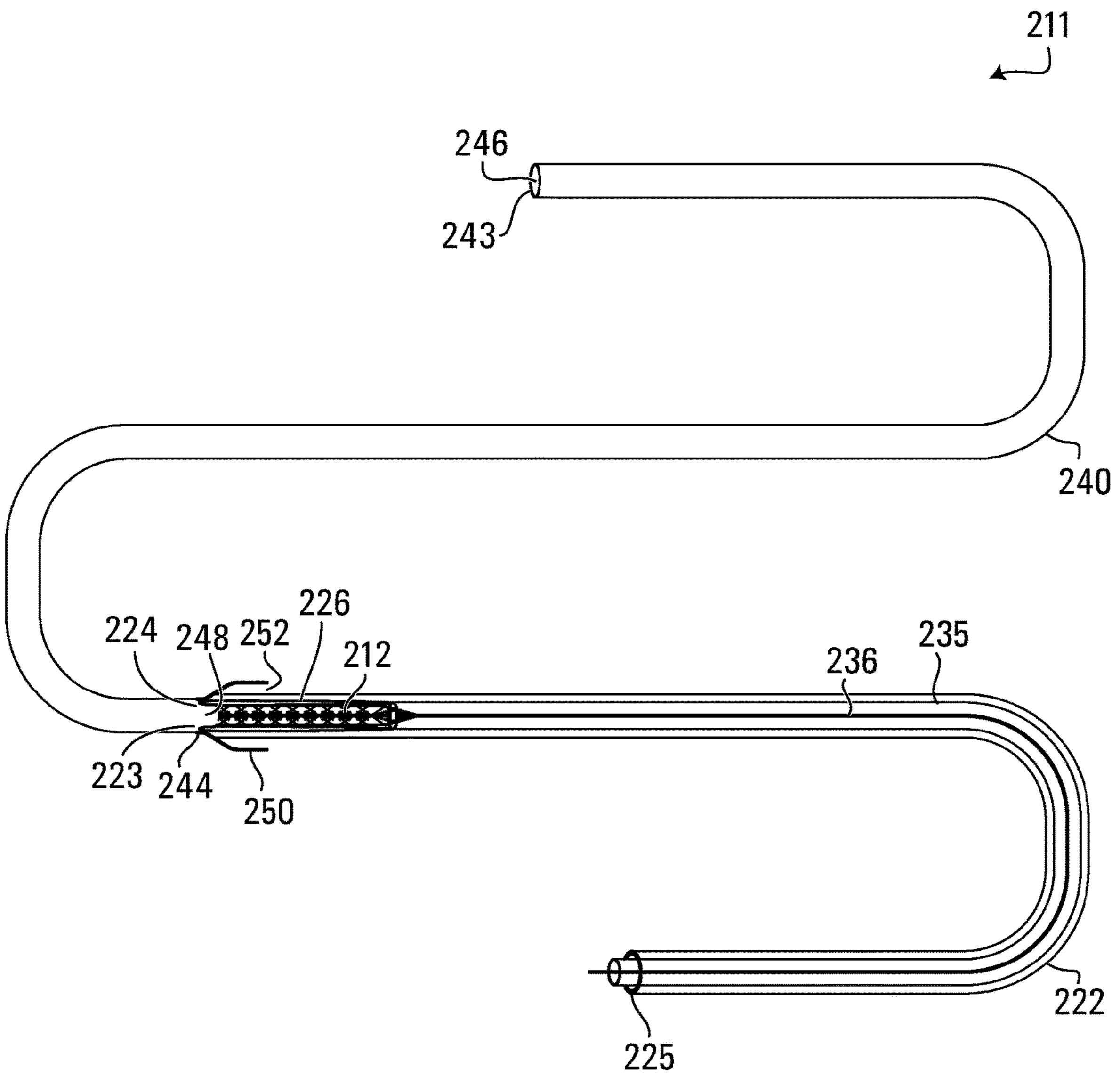
FIG. 7A is a drawing of a system for the deployment of a reversibly compressible endovascular device according to an embodiment of the invention involving a collapsible compressor as depicted in FIGS. 6A and 6B.
Figure 7B:
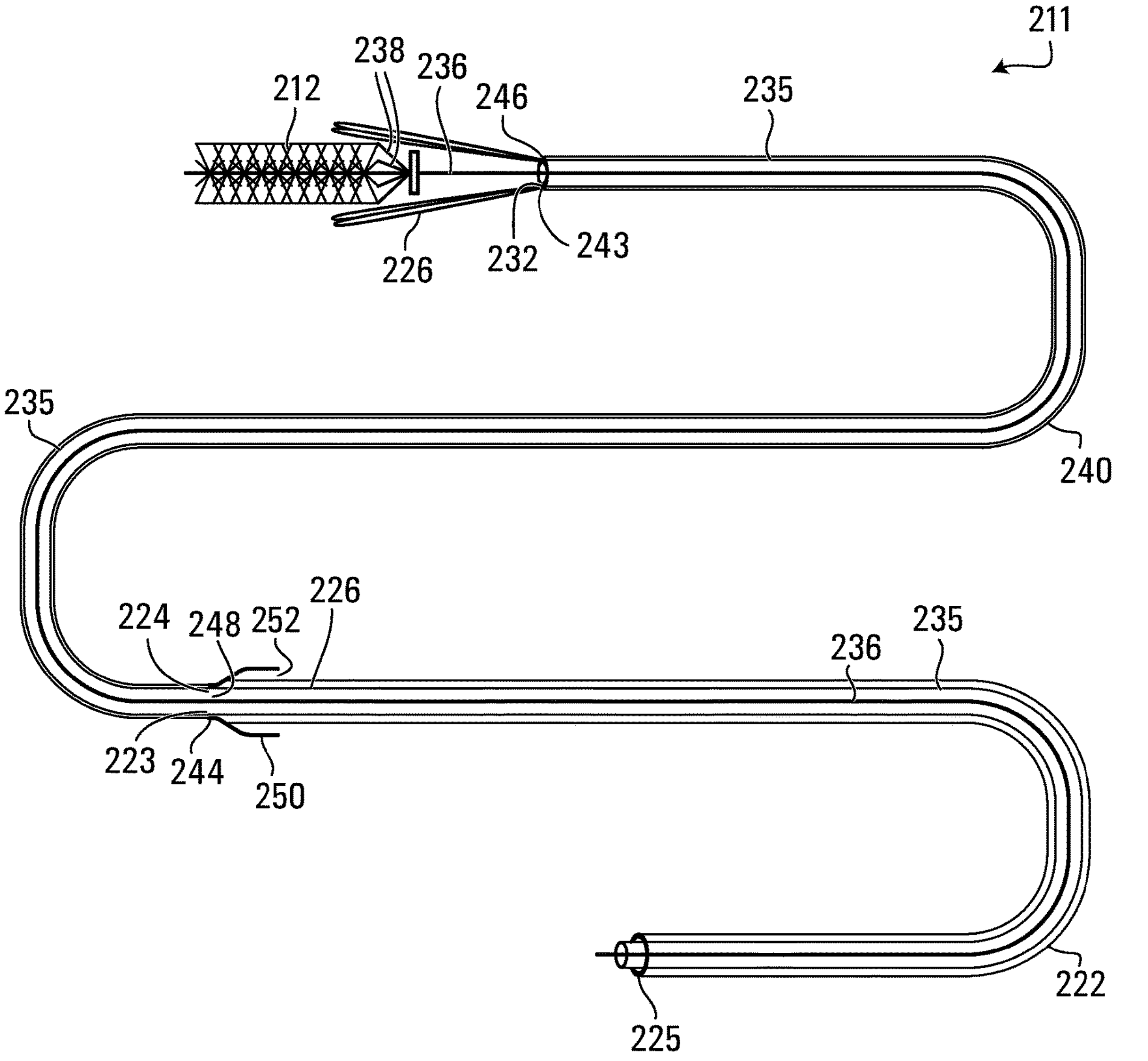
FIG. 7B is a drawing of a system for the deployment of a reversibly compressible endovascular device to the embodiment illustrated in FIG. 7A wherein the endovascular device and compressor are advanced out of the delivery catheter and into the lumen of a vessel.

Referring to FIG. 7B, compressor wire 235 and push wire 236 are operable to be advanced distally through delivery sheath 222 and delivery catheter 240 to urge compressor 226 and ED 212 from the delivery sheath and into the delivery catheter through proximal delivery catheter opening 248, and through the delivery catheter distally toward and distal catheter opening 246. Compressor 226 and ED 212 can then be advanced out distal catheter opening 246 into the lumen of a vessel of a patient. Once in the lumen at the target site and unconstrained by delivery catheter 240, compressor 226 may be expanded from its collapsed position. This, in turn, permits ED 212 to be expanded to its non-compressed position at the target site.

In embodiments where the compressor is a self-expanding compressor, expanding compressor 226 in the lumen involves allowing the compressor to self-expand. In embodiments where the ED is a self-expanding ED, expanding ED 212 in the lumen similarly involves allowing the ED to self-expand to a non-compressed position. It will be within the purview of a skilled person to select and employ an appropriate means of expanding a compressor or an ED. For example, alternatives for expanding the ED may include inflating a balloon disposed within the tubular body of the ED to expand the ED.

Figure 7C:
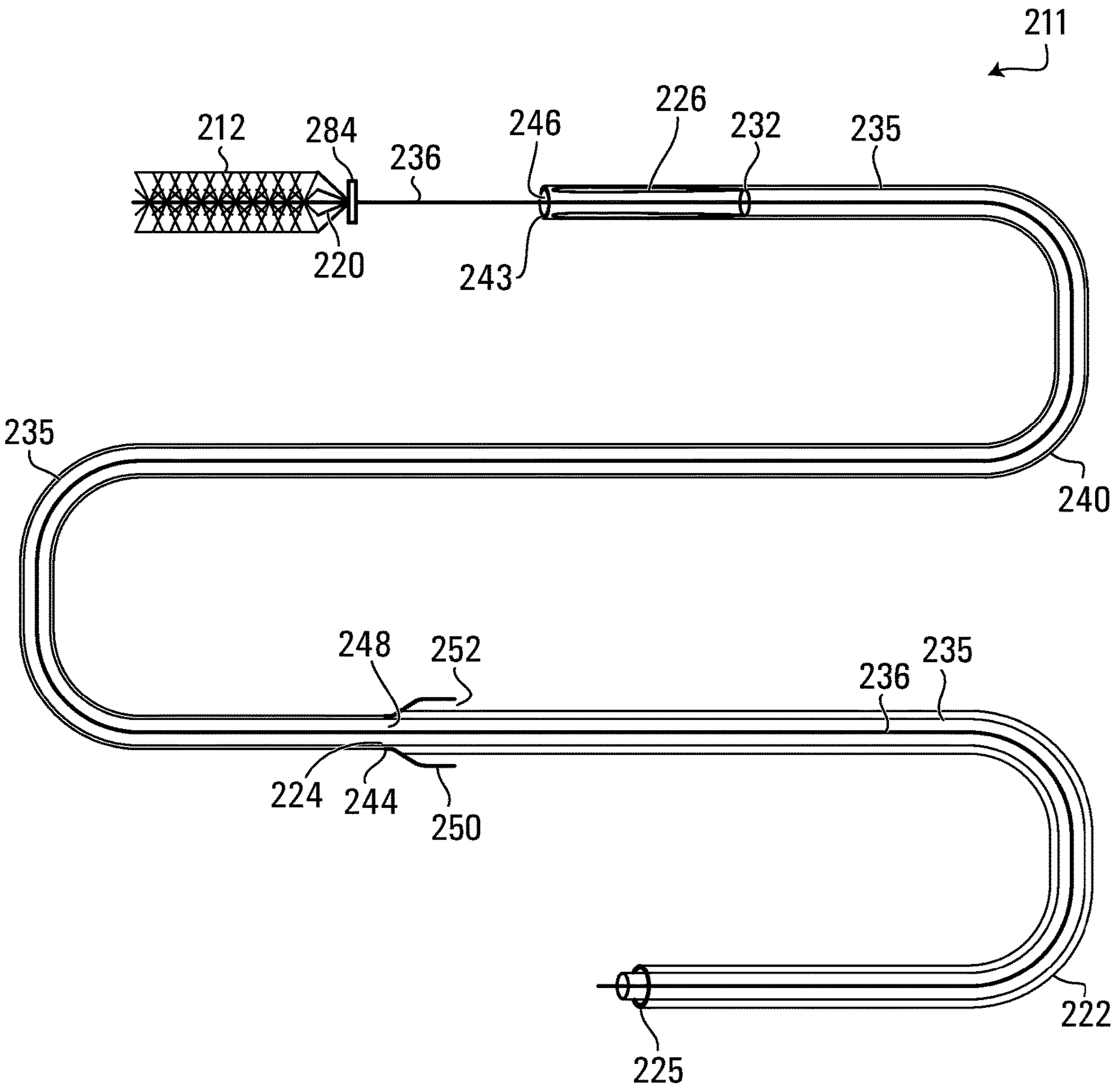
FIG. 7C is a drawing of a system for the deployment of a reversibly compressible endovascular device to the embodiment illustrated in FIG. 7A wherein the endovascular device is advanced out of the delivery catheter and into the lumen of a vessel while the compressor is retained within the delivery catheter.

Alternatively, referring to FIG. 7C, once ED 212 and compressor 226 have been advanced distally to distal delivery catheter end 242, push wire 236 can be used to urge ED 212 independently of compressor 226 out distal delivery catheter opening 246 into the lumen, where ED 212 may expand to its non-compressed position at the target site, while the compressor is retained within delivery catheter 240.

Figure 7D:
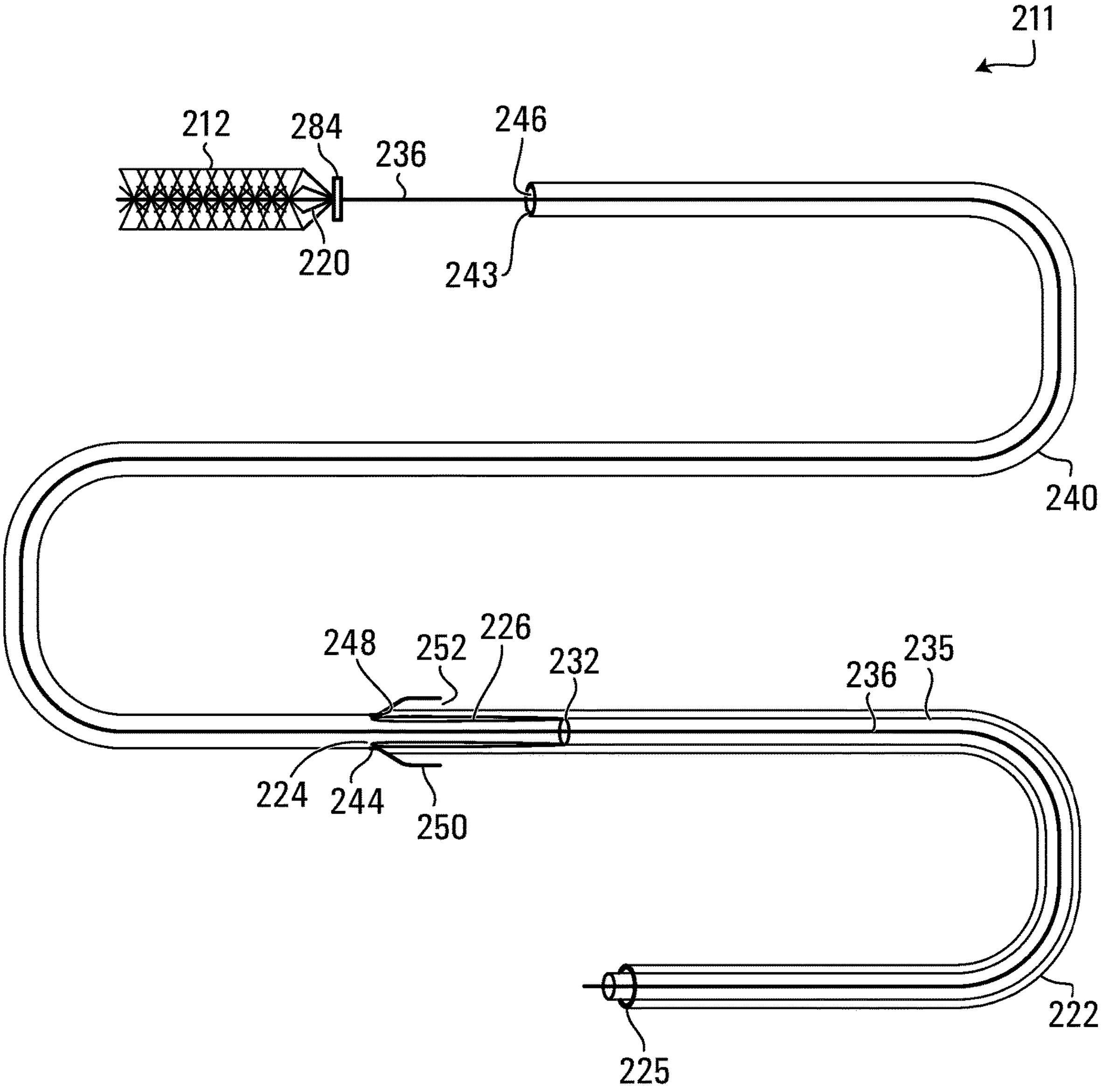
FIG. 7D is a drawing of a system for the deployment of a reversibly compressible endovascular device to the embodiment illustrated in FIG. 7A wherein the endovascular device is advanced out of the delivery catheter and into the lumen of a vessel while the compressor is retained within the delivery sheath.

Yet alternatively, and referring to FIG. 7D, push wire 236 is operable to be advanced distally through delivery sheath 222 and delivery catheter 240 independently of compressor wire 235 to advance ED 212 from the delivery sheath and into the delivery catheter through proximal delivery catheter opening 248, and through the delivery catheter distally toward distal delivery catheter opening 246, while compressor 226 is retained in delivery sheath 222. When push wire 236 is advanced distally, bump member 284 abuts the proximal end of ED 212 at proximal ED opening 220 to apply a force uniformly across the circumference of the ED at the proximal end to urge ED 212 distally while compressor 226 remains in position or is retracted proximally. Once in delivery catheter 240, ED 212 can then be advanced distally out distal catheter opening 246 into the lumen where ED 212 may expand to its non-compressed position at the target site.

Once in its non-compressed position at the target site, threads 238 may be detached from ED 212, and delivery catheter 240 may then be repositioned for the deployment of a further ED, or removed from the patient.

Alternatively, in embodiments employing threads and a compressor that is deployed within the lumen, it may be desirable to reposition an ED before the threads are detached. In such embodiments, compressor wire 235 and push wire 236 are operable to be retracted proximally toward hub 250 to urge deployed ED 212 and expanded compressor 226 back toward the distal delivery catheter opening 246, wherein collapse of compressor 226 upon reception within delivery catheter 240, as with previous reception within delivery sheath 222, exerts a radial force upon ED 212 sufficient to compress the ED for reception in the delivery catheter.

In operation, delivery catheter 240 will typically be deployed in a vessel of a subject, such that distal delivery catheter end 242 is positioned at a target site, with hub 250 remaining outside of the body of the subject. ED 212 is loaded in delivery sheath 222 as described above with reference to FIGS. 6A and 6B. Referring to FIG. 7A, distal end 223 of delivery sheath 222, with ED 212 compressed within it, is then inserted in hub 250. Delivery sheath opening 224 is then registered with proximal delivery catheter opening 248.

Referring to FIG. 7B, compressor wire 235 and push wire 236 are then used to advance compressor 226 and ED 212 through the delivery sheath opening 224 into delivery catheter 240 through proximal delivery catheter opening 248, and then distally through the delivery catheter toward distal delivery catheter end 242. Compressor 226 and ED 212 are then advanced through distal delivery catheter opening 246 into the lumen of the vessel where the compressor is expanded to its non-collapsed position. With the expansion of compressor 226, ED 212 may be expanded in the lumen at the target site.

Alternatively, referring to FIG. 7C, once ED 212 and compressor 226 are advanced to distal delivery catheter end 243, push wire 236 may be used to urge ED 212 through distal delivery catheter opening 246 independently of compressor 236 (which is held in position or retracted proximally using compressor wire 235) and into the lumen of the vessel where ED 212 may be expanded in the lumen at the target site while compressor 236 remains in the delivery catheter.

Alternatively, and referring to FIG. 7D, once delivery sheath opening 224 is registered with proximal delivery catheter opening 248, push wire 236 is used to advance ED 212, independently of compressor 236, through the delivery sheath opening 224 into delivery catheter 240 through proximal delivery catheter opening 248, and then distally through the delivery catheter toward distal delivery catheter end 243. ED 212 is then advanced through distal delivery catheter opening 246 into the lumen of the vessel where ED 212 may be expanded in the lumen at the target site while compressor 236 remains in delivery sheath 222.

In embodiments where the ED is a self-expanding ED, expanding ED 212 in the lumen involves allowing the ED to self-expand. It will be within the purview of a skilled person to select and employ an appropriate means of expanding an ED. For example, alternatives for expanding the ED may include inflating a balloon disposed within the tubular body of the ED to expand the ED.

In embodiments where compressor 236 is deployed into the lumen, if repositioning of the ED is desired, compressor wire 235 and push wire 236 are retracted proximally through delivery catheter 240 to urge reversibly collapsible compressor 226 and ED 212 back through distal delivery catheter opening 246 to collapse compressor 226. As with previous loading within delivery sheath 222, as compressor 226 collapses, it exerts a radial force upon ED 212 to compress the ED into a compressed position for reception in delivery catheter 240. Delivery catheter 240 is then repositioned to a second position. Compressor wire 235 and push wire 236 are again advanced distally to urge compressor 226 and ED 212 out of delivery catheter 240 and into the lumen through distal delivery catheter opening 246. Once compressor 226 is outside of delivery catheter 240, it may again be expanded, thereby allowing ED 212 to be expanded at the second position. Once the ED 212 has been satisfactorily positioned within the lumen, threads 238 may be detached.

The delivery catheter may then be repositioned for the deployment of a further ED, or removed.

Direct Loading of Endovascular Device within Delivery Catheter

The skilled person will understand that, in some embodiments, it may not be necessary to initially load an ED within a delivery sheath prior to loading the compressed ED within a delivery catheter. Rather, an ED could be directly loaded into the distal end of a delivery catheter.

For example, in a conventional method of introducing an ED into the lumen of a vessel, a multi-catheter system, e.g. a triaxial system, is employed. Typically, a guide catheter having proximal and distal guide catheter openings is introduced into a vessel of a patient through the skin. The guide catheter is advanced within the vessel until the distal guide catheter opening is proximal to the target site in the vessel. An intermediate catheter having proximal and distal intermediate catheter openings is then advanced through the guide catheter until the distal intermediate catheter opening is at the target site. Finally, a delivery catheter having proximal and distal delivery catheter openings is advanced through the intermediate catheter until the distal delivery catheter opening is at the target site. In such embodiments, delivery catheters could be supplied pre-packaged with a reversibly compressible ED in a non-compressed position for direct loading into the distal end of a delivery catheter, similar to the systems for loading into the distal ends of a delivery sheath as described above with reference to FIGS. 1, 3, 4A, 4B, 6A, and 6B.

Figure 8:
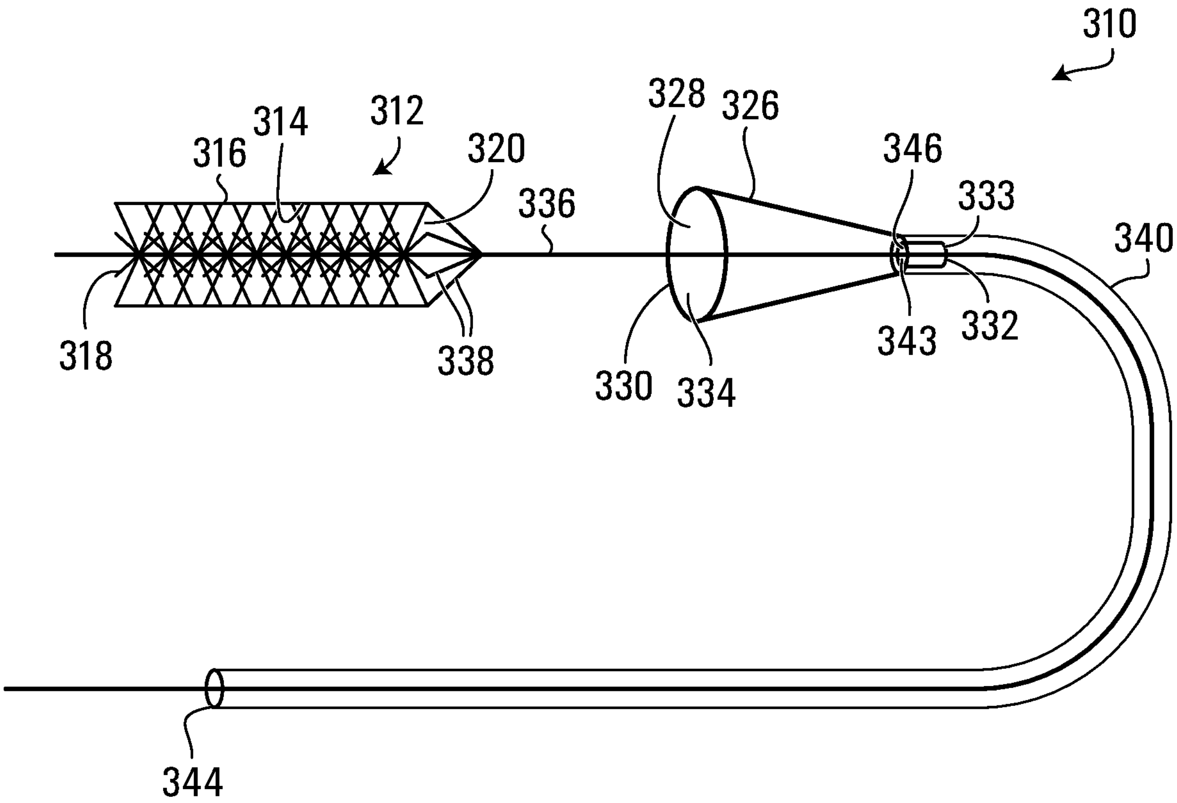
FIG. 8 is a drawing of a system for the radial compression of a reversibly compressible endovascular device directly into a delivery catheter prior to deployment according to a fifth embodiment of the invention.

Accordingly, referring to FIG. 8, a system for the radial compression of a reversibly compressible endovascular device (ED) prior to deployment according to a fifth embodiment of the invention is shown generally at 310. The system includes a reversibly compressible ED 312 as are generally known in the art. In general, the ED comprises a tubular body that is resiliently deformable from a non-compressed position, as depicted in FIG. 8, to a compressed position for loading within a delivery catheter for delivery to a target site in the lumen of a vessel within the body of a subject. The tubular body has an inner surface 314, an outer surface 316, and opposed distal and proximal ED openings 318 and 320.

The system further includes a delivery catheter 340 sized to receive and maintain the ED 312 in the compressed position upon reception in the delivery catheter in the compressed position. Delivery catheter 340 has a distal delivery catheter end 343 having a distal delivery catheter opening 346. Distal delivery catheter opening 346 has a width sized to receive the ED 312 into delivery catheter 340 in a compressed form.

The system further includes a compressor 326 for radially compressing ED 312 for reception by delivery catheter 340 through the distal delivery catheter opening 346. The compressor 326 has a generally tapered structure defining an interior space 328. The tapered structure comprises distal and proximal compressor ends 330 and 332, wherein proximal compressor end 332 is proximal to distal delivery catheter opening 346.

Distal compressor end 330 comprises a distal compressor opening 334 sized to receive the ED 312 in the non-compressed position. As illustrated in FIG. 8, compressor 326 tapers from distal compressor opening 334 toward proximal compressor end 332 such that the radial cross section of the interior space 328 diminishes from distal compressor end 330 toward proximal compressor end 332. Proximal compressor end 332 comprises a proximal compressor opening 333 in communication with distal delivery catheter opening 346. The width of proximal compressor opening 333 is smaller than the radial diameter of the ED 312 when the ED is in the non-compressed position. The radial cross sectional area of interior space 328 proximal at proximal compressor end 332, e.g. at proximal compressor opening 333, is equal to or less than the radial cross sectional area of distal delivery catheter opening 346. In this way, as ED 312 moves through compressor 326, it will be compressed to have a radial cross section less than the radial cross section of the distal delivery catheter opening 346, such that ED 312 can be received within delivery catheter 340 in the compressed position. As such, ED 312, in a compressed form, can be urged through proximal compressor opening 333 and received within delivery catheter 340 through distal delivery catheter opening 346.

The system further comprises a push wire 336 that is detachably attached to ED 312. Push wire 336 is attached to ED 312 by at least one (i.e. one or more) threads 338. In FIG. 8, threads 338 are shown radiating from push wire 336 and attached to ED 312 at proximal ED opening 320. However, the skilled person understands that threads 338 may be attached to ED 312 at a different position, for example, to inner surface 314 or outer surface 316. In some embodiments, threads 338 could be attached at distal ED opening 318.

In some embodiments, the at least one thread is a single thread comprising a lasso, wherein the lasso is looped and tightened around the tubular body of the ED near proximal ED opening to form a cincture about the proximal end of the ED.

Threads 338 may be electrolytically detachable from ED 312 once the ED is positioned at the target site within the lumen of the vessel, as is known in the field. Alternatively, threads 338 may be mechanically detachable from ED 312. It is within the purview of the skilled person to select an appropriate means of detaching threads 338 from the ED. In embodiments involving a lasso-style attachment, the loop of the lasso may be broken to release ED.

Threads 338 may be made of any suitable materials as are known in the field. For example, threads 338 may be made of metal wire.

As shown in FIG. 8, and push wire 336 is disposed within delivery catheter 340, and operable to be advanced proximally through delivery catheter 340 to urge ED 212 through compressor 326, whereby ED 312 is deformed into a compressed position as it is urged through the compressor from distal compressor end 330 to proximal compressor end 332, and further urged through proximal compressor opening 333 into delivery catheter 340 in a compressed position.

As shown in FIG. 8, push wire 336 may also be disposed within ED 312 through proximal ED opening 320.

A depicted in FIG. 8, compressor 326 may take the form of a funnel. In some embodiments, the width of proximal compressor end 332 is smaller than the width of distal delivery catheter opening 346 such that proximal compressor end 332 is sized to be received within delivery catheter 340 through distal delivery catheter opening 346. However, in alternative embodiments, the second compressor end may abut the distal delivery catheter end 343. The skilled person understands that the proximal compressor end and the distal delivery catheter end can be designed to cooperate in numerous different ways, and that it is only important that proximal compressor opening have a width equal to or less than the distal delivery catheter opening so that the ED will be in a sufficiently compressed position to be received within the delivery catheter as the ED approaches the proximal compressor end.

As depicted in FIG. 8, the tapered structure (i.e. compressor 326) may have a unitary (i.e. one-piece) body. In the illustrated embodiment, compressor 326 is removable once ED 312 has been received in a compressed position within delivery catheter 340.

In operation, starting with ED 312 in an expanded position, retracting push wire 336 proximally into delivery catheter 340 urges ED 312 into interior space 328 of compressor 326 via distal compressor opening 334, and toward proximal compressor end 332 to radially compress ED 312 to a compressed (i.e. unexpanded) position as the cross sectional area of interior space 328 diminishes along the longitudinal axis from distal compressor end 330 toward proximal compressor end 332. Further retraction of push wire 336 proximally toward proximal delivery catheter opening 344 urges ED 312 in the compressed position through proximal compressor opening 333 and into delivery catheter 340 through distal delivery catheter opening 346.

Deployment

Once ED 312 has been received within delivery catheter 340 in a compressed position, the delivery catheter can be used in conjunction with a multi-catheter system as described above for delivery of the ED to the target site.

Figure 9A:
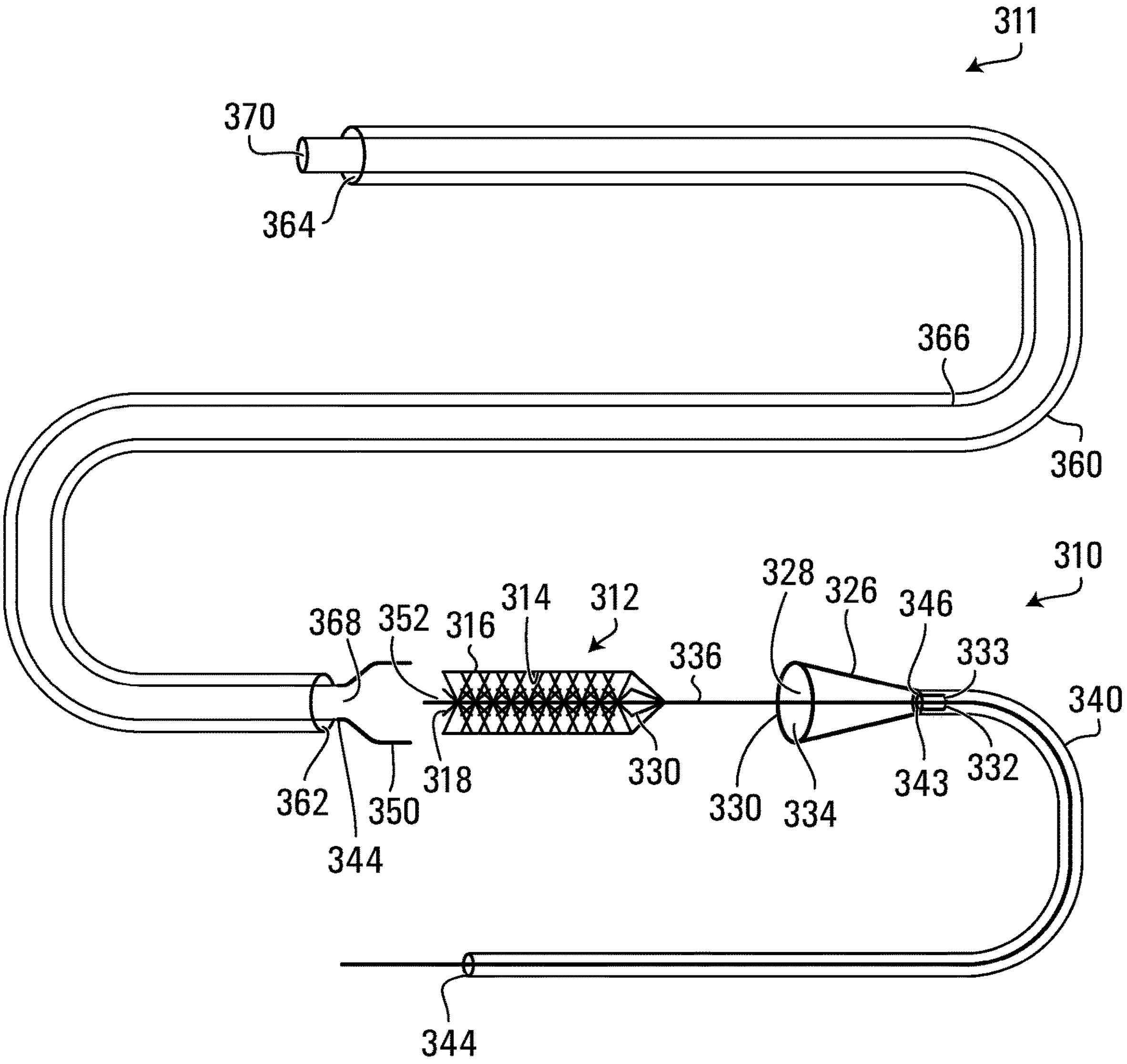
FIG. 9A is a drawing of a system for the deployment of a reversibly compressible endovascular device according to a fifth embodiment of the invention.
Figure 9B:
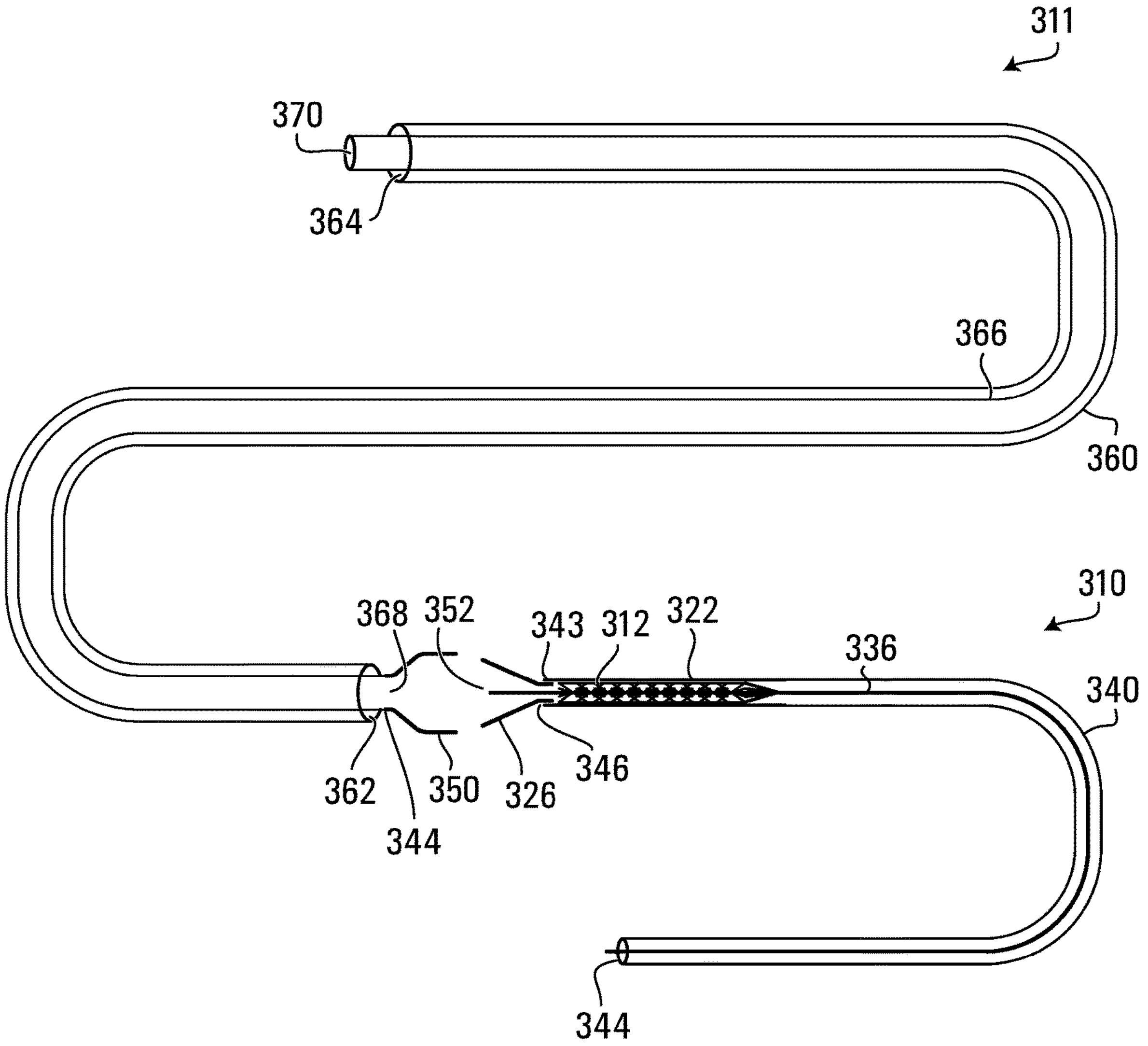
FIG. 9B is a drawing of a system for the deployment of a reversibly compressible endovascular device according to the embodiment illustrated in FIG. 9A, but with the endovascular device compressed within the delivery catheter.

Referring to FIGS. 9A and 9B, a system for deploying a reversibly compressible endovascular device within a lumen of a vessel is shown generally at 311. The system comprises a system for the radial compression of a reversibly compressible endovascular device (ED) prior to deployment as described above with reference to FIG. 8. The system further comprises a guide catheter 360 having proximal and distal guide catheter openings 362 and 364. Guide catheter 360 is for advancement in a vessel of a subject to a position wherein distal guide catheter opening 364 is proximal to a target site. The system further comprises an intermediate catheter 366 comprising proximal and distal intermediate catheter openings 368 and 370. Intermediate catheter 366 is for advancement within guide catheter 360 to a position where distal intermediate catheter opening 370 is at the target site.

Delivery catheter 340 is for advancement within intermediate catheter 366 to a position where distal delivery catheter opening 346 is at the target site.

Push wire 336 is operable to be advanced through delivery catheter 340 to urge ED 312 distally from the delivery catheter and out distal delivery catheter opening 346.

Figure 9C:
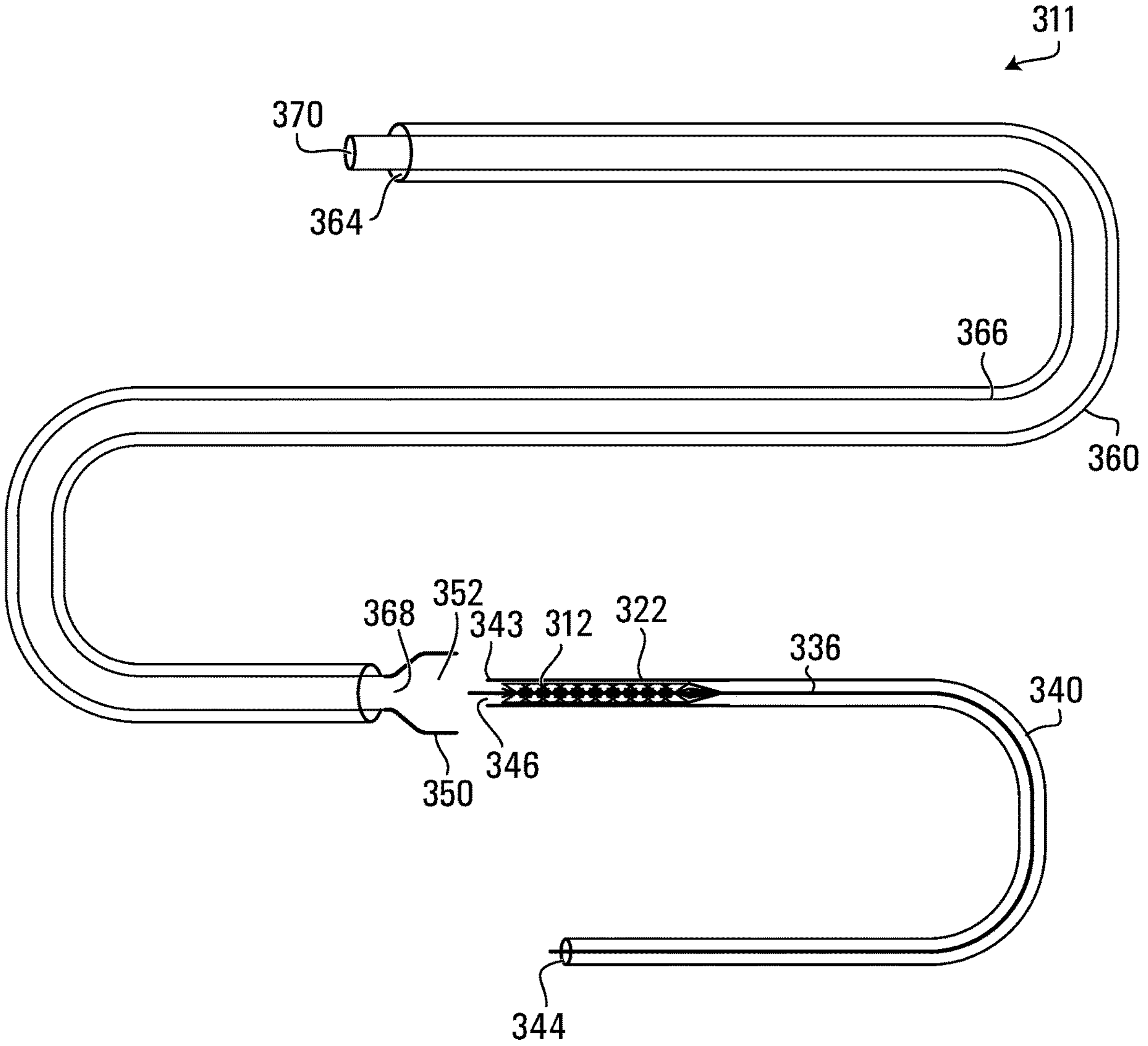
FIG. 9C is a drawing of a system for the deployment of a reversibly compressible endovascular device according to the embodiment illustrated in FIGS. 9A and 9B, but after the compressor has been removed.

In operation, guide catheter 360 and intermediate catheter 366 will typically be deployed in a vessel of a subject, such that distal guide catheter opening 364 and distal intermediate catheter opening 370 are positioned at the target site. Referring FIGS. 9A and 9B, ED 312 is loaded in delivery catheter 340 as described above. Referring to FIGS. 9B and 9C, compressor 326 may then be removed from system 310 prior to engaging loaded delivery catheter 340 with intermediate catheter 366.

Figure 9D:
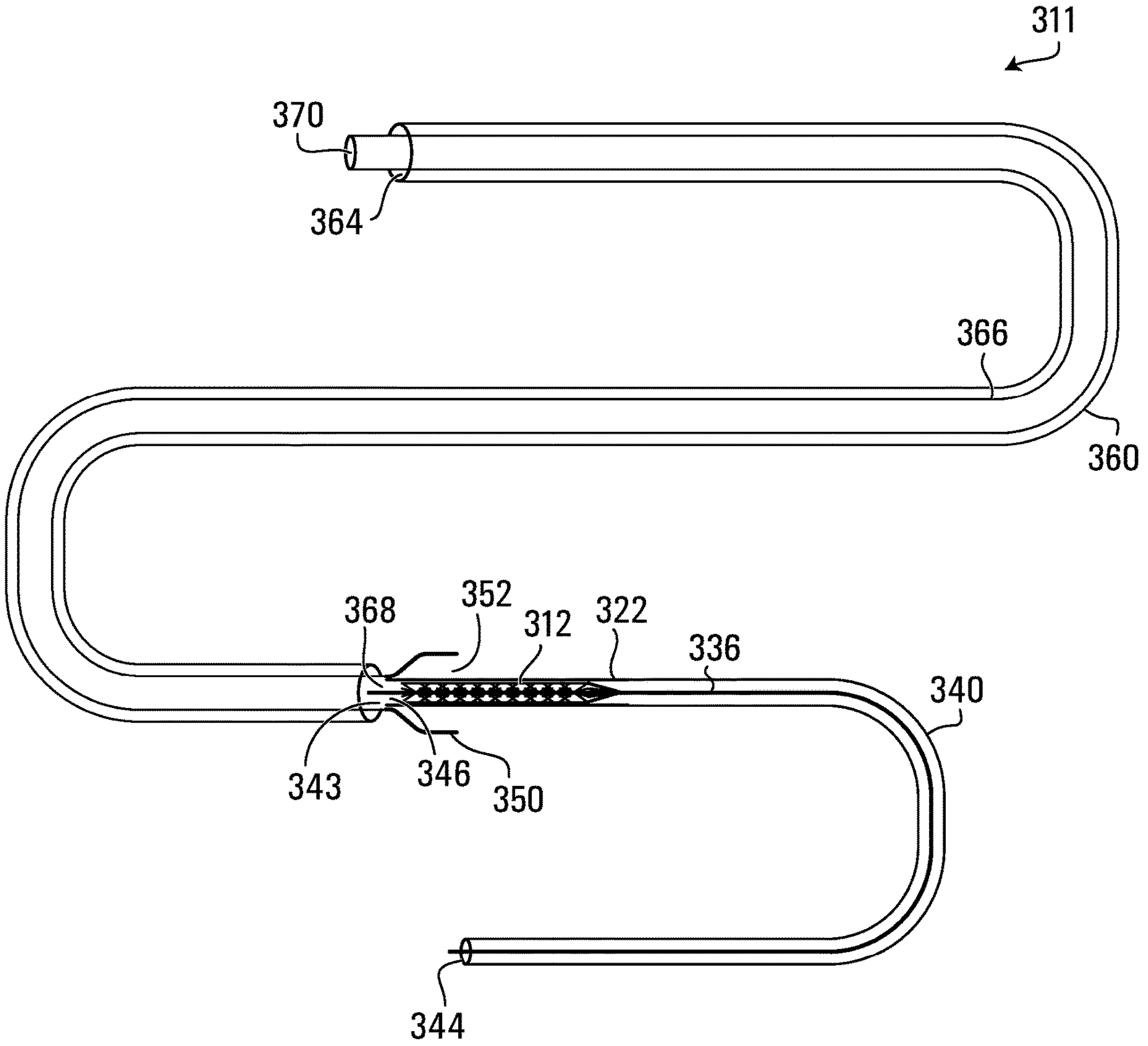
FIG. 9D is a drawing of a system for the deployment of a reversibly compressible endovascular device according to the embodiment illustrated in FIGS. 9A, 9B, and 9C, but with the delivery catheter inserted within the intermediate catheter through the hub opening.
Figure 9E:
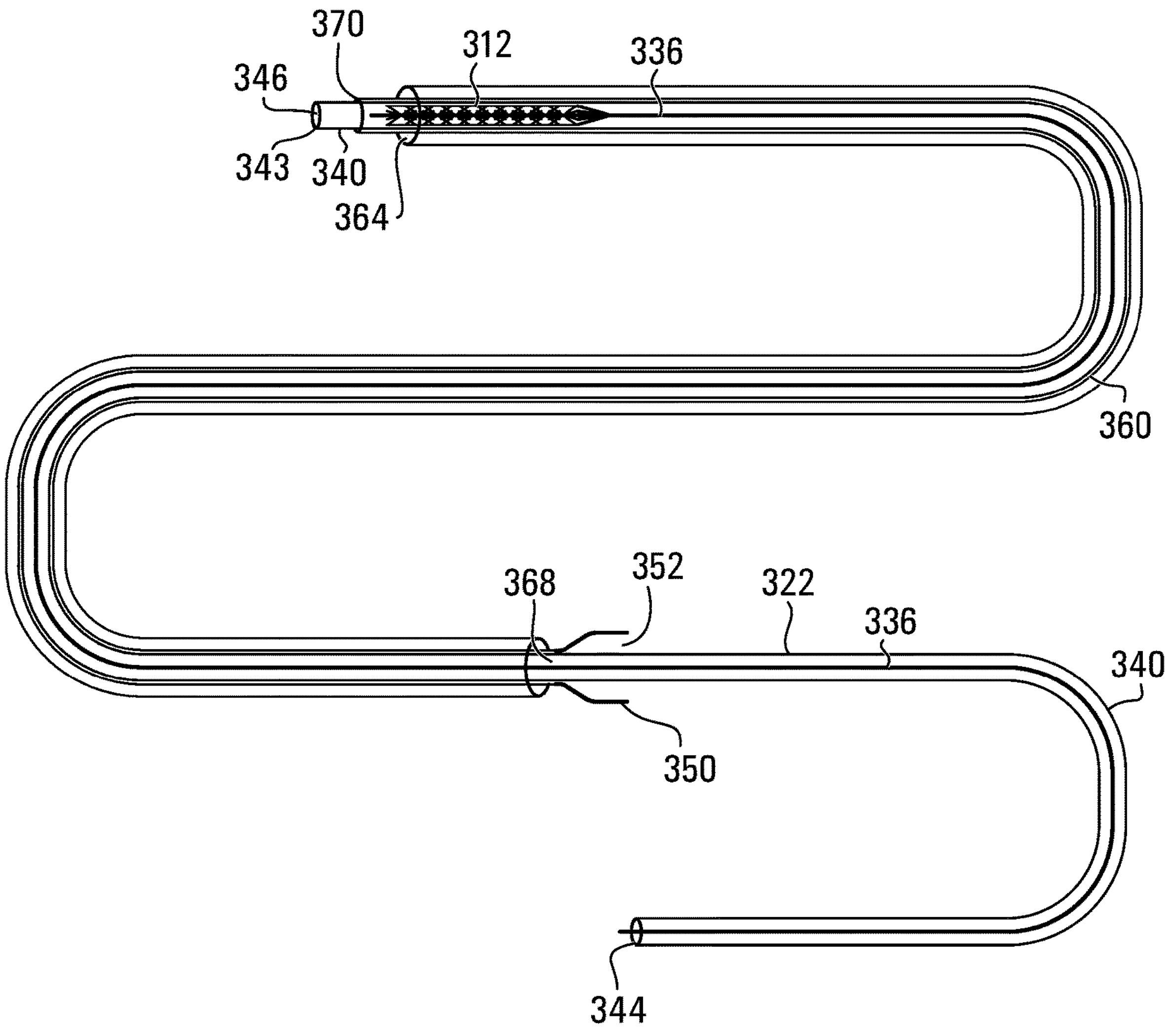
FIG. 9E is a drawing of a system for the deployment of a reversibly compressible endovascular device according to the embodiment illustrated in FIGS. 9A, 9B, 9C, and 9D, showing the delivery catheter with the compressed endovascular device at the distal delivery catheter end advanced to the distal intermediate catheter opening prior to deployment of the endovascular device at a target site within a lumen of a subject.
Figure 9F:
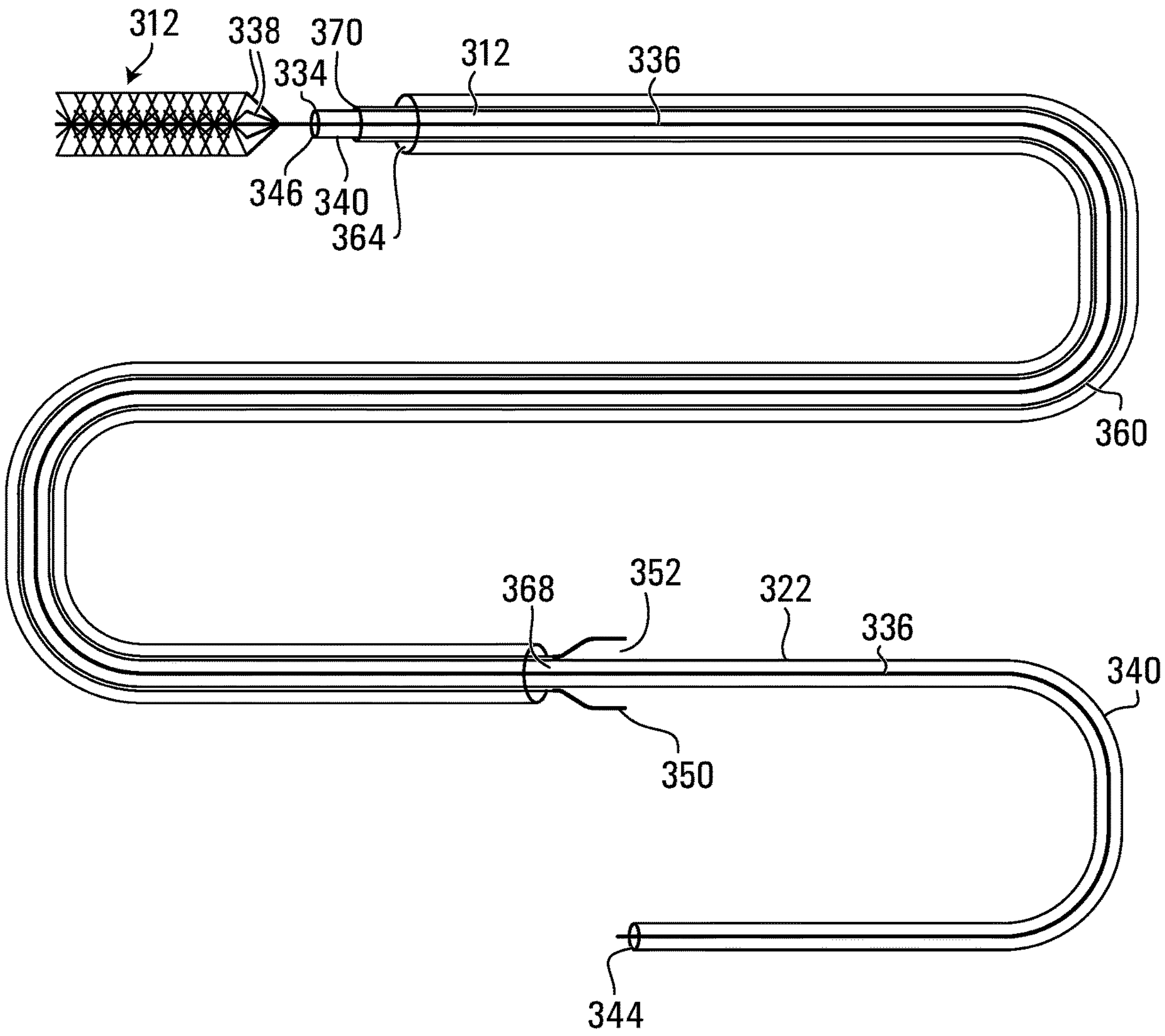
FIG. 9F is a drawing of a system for the deployment of a reversibly compressible endovascular device according to the embodiment illustrated in FIGS. 9A, 9B, 9C, 9D, and 9E showing the endovascular device advanced out of the distal opening of the delivery catheter and expanded at the target site within the lumen.

Referring to FIG. 9D, distal delivery catheter end 343, with ED 312 compressed within it, is then inserted in intermediate catheter 366 through proximal intermediate catheter opening 368. Referring to FIG. 9E, delivery catheter 340 is then advanced distally through intermediate catheter 366 until distal delivery catheter opening 346 is at the target site. Referring to FIG. 9F, push wire 336 is then used to advance ED 312 distally through distal delivery catheter opening 346 into the lumen of the vessel where it is expanded to its non-compressed position at the target site. Once in its non-compressed position at the target site, threads 338 are detached from ED 312. Delivery catheter 340 may then be removed, at which time a new delivery catheter, loaded with an ED, can be introduced.

In embodiments where the ED is a self-expanding ED, expanding ED 312 in the lumen involves allowing the ED to self-expand. It will be within the purview of a skilled person to select and employ an appropriate means of expanding an ED. For example, alternatives for expanding the ED may include inflating a balloon disposed within the tubular body of the ED to expand the ED.

While direct loading of a delivery catheter has been described above with regards to embodiments involving a non-collapsible compressor, the skilled person will readily understand that the embodiments involving a collapsible compressor as described with reference to FIGS. 3, 4A, 4B, and 5A to 5G, or a collapsible compressor and an ED that are moveable independent of each as described in FIGS. 6A, 6B, and 7A to 7D in connection with a delivery sheath could also be adapted for direct loading of an ED into the distal end of a delivery catheter.

The skilled person will also understand that, in some embodiments, an ED could be directly loaded into a delivery catheter through the proximal delivery catheter opening. That is, the compressor could be positioned in reversed orientation, i.e. such that it tapered from the proximal compressor end to the distal compressor end, to radially compress ED 312 for reception by the delivery catheter through proximal delivery catheter opening 344. In such embodiments, the distal compressor opening is in communication with the proximal delivery catheter opening 344. The width of the distal compressor opening would be smaller than the radial diameter of the ED 312 when the ED is in the non-compressed position. The radial cross sectional area of interior space at the distal compressor end, e.g. at the distal compressor opening, would equal to or less than the radial cross sectional area of proximal delivery catheter opening 344. In this way, as the ED is urged through the compressor, it would be compressed to have a radial cross section less than the radial cross section of the proximal delivery catheter opening 344, such that ED 312 could be received within delivery catheter in the compressed position. As such, the ED, in a compressed form, can be urged through distal compressor opening and received within the delivery catheter. The threads by which the push wire was attached to the ED may preferably be attached at the distal ED opening, such that advancing the push wire into the delivery catheter through the compressor would effectively pull the ED through the compressor. Alternatively, a pull wire extending through the distal delivery catheter opening, the delivery catheter, and the proximal delivery catheter, and attached to the ED at the distal ED opening, could be used to pull the ED through the compressor (thereby compressing the ED) and into the delivery catheter through the proximal delivery catheter opening. The pull wire could then be used to pull the ED through the delivery catheter to the distal catheter end. The pull wire is detachably attached to the ED such that, when the ED is at the distal delivery catheter end, the pull wire could be detached from the ED. The delivery catheter, with the ED loaded inside, could then be introduced to patient using, for example, a triaxial system as described above.

Figure 10:
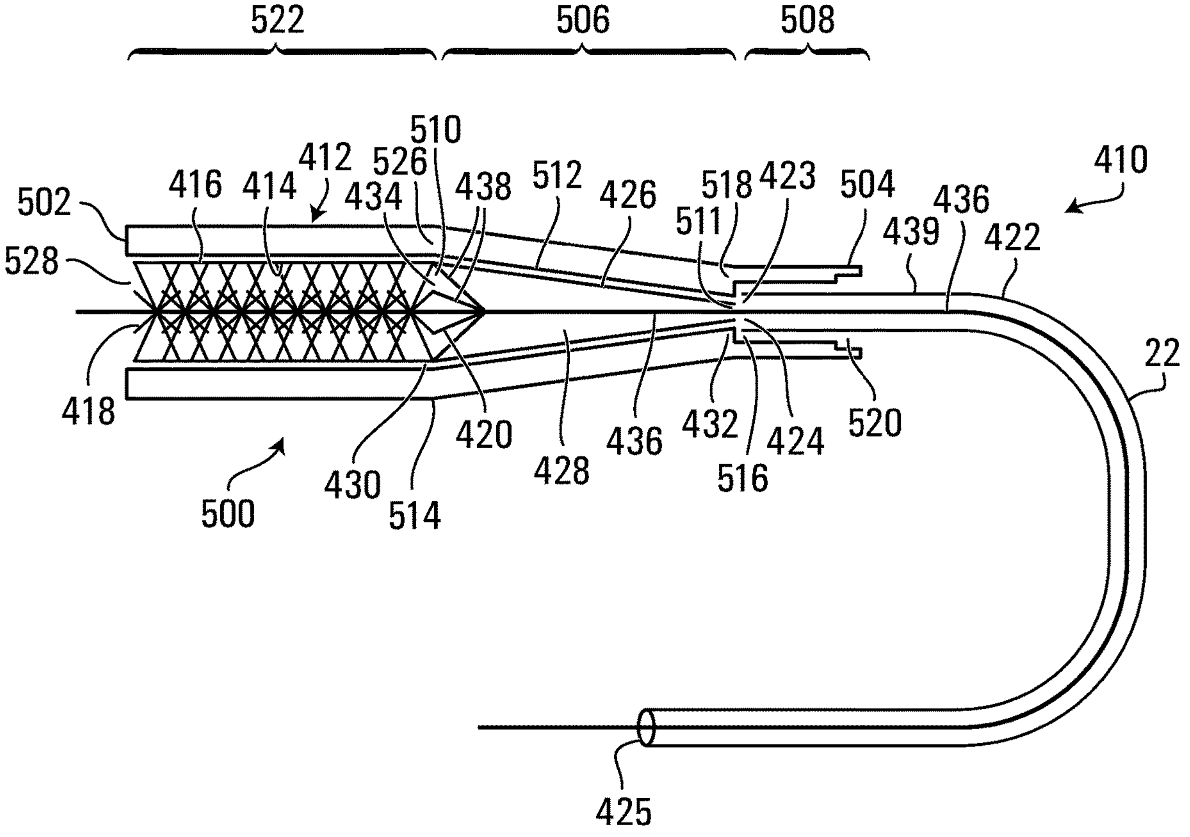
FIG. 10 is a drawing of a system for the radial compression of a reversibly compressible endovascular device directly into a delivery catheter prior to deployment according to a sixth embodiment of the invention.

Referring to FIG. 10, a system for the radial compression of a reversibly compressible endovascular device (ED) prior to deployment according to a sixth embodiment of the invention is shown generally at 410. The system includes a reversibly compressible ED 412 as are generally known in the art. In general, the ED comprises a tubular body that is expandable between a non-compressed position, as depicted in FIG. 10, and a compressed position for loading within a delivery catheter for delivery to a target site in the lumen of a vessel within the body of a subject. The tubular body has an inner surface 414, an outer surface 416, and distal and proximal opposed ED openings 418 and 420.

The system further includes a delivery sheath 422 sized to receive and maintain the ED 412 in the compressed position upon reception in the delivery sheath in a compressed position. Delivery sheath 422 has a distal delivery sheath end 423 having a delivery sheath opening 424. Delivery sheath opening 424 has a width sized to receive the ED 412 into delivery sheath 422 in a compressed form. Delivery sheath 422 further has a proximal delivery sheath end 425.

The system further includes a compressor 426 (shown schematically in FIG. 10) for radially compressing the ED 412 for reception in the delivery sheath 422 through delivery sheath opening 424. Compressor 426 may be configured similar in a similar manner to compressors 126, 226 described above and includes a generally tapered structure defining an interior space 428 in which ED 412 initially may be at least partially positioned in a non-compressed position. Compressor 426 comprises distal and proximal compressor ends 430 and 432.

Distal compressor end 430 comprises a distal compressor opening 434 sized to receive the ED 412 in the non-compressed position. As illustrated in FIG. 10, compressor 426 tapers from distal compressor opening 434 toward proximal compressor end 432 such that the radial cross section of the interior space 428 diminishes from distal compressor end 430 toward proximal compressor end 432. The width of compressor 426 at proximal compressor end 432 is less than the width of delivery sheath opening 424 such that proximal compressor end 432 is sized to be received within delivery sheath 422 through delivery sheath opening 424 as will be described below.

Compressor 426 is collapsible such that, as it collapses, the cross sectional area of interior space 428 at any position along the longitudinal axis of the compressor from distal compressor end 430 to proximal compressor end 432 progressively decreases. As the cross sectional area of interior space 428 decreases, compressor 426 exerts a radial force against ED 412 positioned therein to compress ED 412.

Compressor 426 is sized such that, in a collapsed form, it is sized to be received within delivery sheath 422 through delivery sheath opening 424. ED 412, being compressed within interior space 428 as compressor 126 collapses, is thereby compressed for reception within delivery sheath 422.

The system further comprises a push wire 436 that is attached to proximal compressor end 432. Push wire 436 is also detachably attached to ED 412. Push wire 436 is attached to ED 412 by at least one (i.e. one or more) threads 438. In FIG. 10, threads 438 are shown radiating from push wire 436 and attached to ED 412 at proximal ED opening 420. However, the skilled person understands that threads 438 may be attached to ED 412 at a different position, for example, to inner surface 414 or outer surface 416. In some embodiments, threads 438 could be attached at distal ED opening 418.

The skilled person further understands that one or more threads 438 may attach ED 412 to compressor 426 rather than push wire 436. In some embodiments, the at least one thread is a single thread comprising a lasso, wherein the lasso is looped and tightened around the tubular body of the ED proximal to proximal ED opening to form a cincture about the proximal end of the ED.

As discussed above in respect of the first embodiment, threads 438 may be electrolytically or mechanically detachable from ED 412 once the ED 412 is positioned at the target site within the lumen of the vessel, as is known in the field. In embodiments involving a lasso-style attachment, the loop of the lasso may be broken to release ED. Similarly, threads 438 may be made of any suitable materials as are known in the field.

ED 412 may not be connected to compressor 426 and/or push wire 436 by threads. Rather, compressor 426 may be sized and configured such that ED 412 is initially frictionally engaged with an interior surface of compressor 426. Accordingly, as compressor 426 is drawn into delivery sheath 422 through delivery sheath opening 424, the frictionally engaged ED 412 is drawn with it and is compressed as compressor 426 collapses.

As shown in FIG. 10, push wire 436 is disposed within delivery sheath 422, and is operable to be retracted proximally through delivery sheath 422 toward proximal delivery sheath end 425 to urge compressor 426 into delivery sheath 422 through delivery sheath opening 424. In various embodiments, an inner wall 439 of delivery sheath 422 is operable to exert a force against the outer surface of compressor 426 as compressor 426 is received within the delivery sheath, that is sufficient to collapse the tapered structure.

As shown in FIG. 10, push wire 436 may also be disposed within ED 412 through proximal ED opening 420.

As depicted in FIG. 10, compressor 426 may take the general form of a funnel. In some embodiments, the compressor 426 comprises a plurality of overlapping tongues, similar to as described above for compressor 126. However, the skilled person will understand that collapsible compressors according to the present disclosure could include a variety of radially compressible structures that, when at least partially received within the delivery sheath, form a tapered structure that can accommodate an ED in non compressed form and, as urged into the delivery sheath along with the ED, collapse to compress the ED to a compressed form. Such compressors could be formed of a braided structure, for example, a polypropylene braided structure or a metal braided structure as is known in the art and used in some cases for the fabrication of EDs themselves.

In various embodiments, compressor 426 is reversibly collapsible. For example, the tapered structure may be resiliently deformable such that, after reception in delivery sheath 422, it may be pushed out of delivery sheath 422 through delivery sheath opening 424 using push wire 436, into and through a delivery catheter, and out a distal delivery catheter opening (e.g. into the lumen of a vessel), at which time it will expand to a non-collapsed formation to permit release of ED 412 at the target site. Alternatively, the tapered structure may be actively expanded upon emergence from the delivery sheath, or deliver catheter as the case may be, by any means known in the art, e.g. using a balloon.

In some circumstances, the friction forces arising from the fictional engagement between the ED 412 and an interior surface of compressor 426 may not be sufficient to prevent the ED 412 from shifting/slipping (relative to compressor 426) as compressor 426 is drawn into delivery sheath 422 through delivery sheath opening 424. This may result in ED 412 not being fully drawn into sheath 422 with compressor 426. This magnitude of these frictional forces may be dependent on the configuration of compressor 426, ED 412 and/or sheath 422. For example, factors such as the extent as to which compressor 426 tapers towards proximal compressor end 432, the materials of compressor 426 and ED 412, the profile of the inner surface of compressor 426 and the size and configuration of ED 412, may affect the magnitude of the frictional forces between the interior surface of compressor 426 and ED 412.

Figure 11:
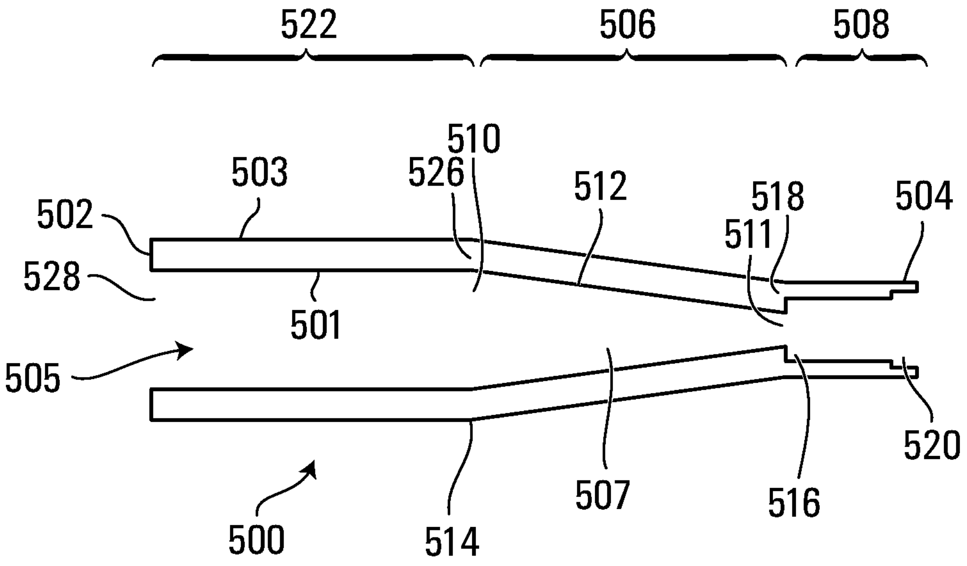
FIG. 11 is a cross sectional side view of a compressor support of the system of FIG. 10.

System 410 further includes a compressor support 500, shown in isolation in FIG. 11. Compressor support 500 comprises a generally tubular body having an inner surface 501 and outer surface 503 and distal and proximal ends 502 and 504 respectively. Outer surface 503 may have any suitable shape. Inner surface 501 defines a cavity 505 extending from distal end 502 to proximal end 504, and includes a body portion 506.

With reference to FIG. 11, body portion 506 is configured to engage and support a portion of the exterior surface 427 of compressor 426 and has distal and proximal ends 514 and 518 respectively and an interior wall 512 defining an insertion bore 507. The distal end 514 of body portion 506 comprises a distal body opening 510 sized to receive compressor 426 (with or without ED 412 in the non-compressed position). The proximal end 518 of body portion 506 comprises a proximal body opening 511 that is narrower than the distal body opening 510 and is sized to receive compressor 426 (with or without ED 412 in the compressed position) and configured for communication with the delivery sheath opening. The diameter of proximal body opening 511 may be slightly smaller than the external diameter of delivery sheath 422.

As shown in FIGS. 10 and 11, the insertion bore 507 (as defined by interior wall 512) has a generally a generally frustoconical shape that tapers between distal body opening 510 and proximal body opening 511 such that the radial cross section of the insertion bore 507 diminishes from the distal end 514 towards the proximal end 518.

The taper of the insertion bore 507 as described above may be complementary to the taper of compressor 426, i.e., the rate (or taper angle) of the taper from the distal body opening 510 towards proximal body opening 511 may be similar to the rate (or taper angle) from distal compressor opening 434 toward proximal compressor end 432. As such, when compressor 426 is situated within body portion 506, at least a portion the exterior surface 427 of compressor 426 abuts the interior wall 512 if body portion 506.

Compressor support 500 may further comprise a first tubular portion 508 having a distal end 516 adjacent to the proximal end 518 of body portion 506 and extending towards the proximal end 504 of compressor 500. First tubular portion 508 is sized to receive a portion of distal delivery sheath end 423 therewithin. First tubular portion 508 may be generally tubular with an inner diameter slightly larger than the outer diameter of delivery sheath 422. When delivery sheath 422 is received within first tubular portion 508, delivery sheath opening 424 may be positioned adjacent to proximal body opening 511 for receiving the compressor 426 and frictionally engaged ED 412 a compressed position as push wire 436 is retracted proximally.

The proximal end 504 of compressor 500 may include a region 520 having an increased internal diameter in comparison to the rest of first tubular portion 508. Region 520 may assist a user in guiding the sheath into first tubular portion 508.

Compressor support 500 may further comprises a second tubular portion 522 extending from distal end 502 of compressor 500 to a proximal end 526 that is adjacent to the distal end 514 of body portion 506. At the distal end 502 there is a distal second tubular portion opening 528 sized to receive compressor 426 and ED 412. Second tubular portion 522 may be generally tubular and may have a length and internal diameter that is at least greater than the external diameter of ED 412 in the non-compressed position. As will be explained in greater detail below, the second tubular portion 522 may house the ED 412 during storage and/or shipping to protect the stent from contamination and/or damage.

As shown in FIG. 10, push wire 436 is disposed within delivery sheath 422, and is operable to be retracted proximally through delivery sheath 422 toward proximal delivery sheath end 425 to urge compressor 426 through compressor support 500 and into delivery sheath 422 through delivery sheath opening 424.

In operation, starting with ED 412 in an expanded position, retracting push wire 436 into delivery sheath 422 toward proximal delivery sheath end 425 urges compressor 426 into body portion 506 though distal body opening 510. Continued retraction of push wire 436 into delivery sheath 422 urges compressor 426 into delivery sheath 422 through delivery sheath opening 424.

As compressor 426 is urged into delivery sheath 422, the cross sectional area of interior space 428 at any position along the longitudinal axis of the compressor 426 from distal compressor end 430 to proximal compressor end 432 is progressively reduced, wherein compressor 426 exerts a radial force against ED 412 positioned therein to radially compress the ED for reception within delivery sheath 422 through delivery sheath opening 424.

The interior wall 512 of body portion 506 provides lateral support to the exterior surface of the compressor 426 as the compressor 426 is drawn proximally through the proximal opening of body portion 506 and into delivery sheath 422 through delivery sheath opening 424. The lateral support provided by interior wall 512 may ensure that the strength of frictional engagement between the compressor 426 and ED 412 is maintained as compressor 426 is drawn proximally, such that shifting/slipping of the ED 412 relative to the compressor 426 is reduced or substantially eliminated. Further, the gradual and consistent taper of interior wall 512 (as described above) ensures that the compressor 426 maintains a complementary gradual and consistent tapered shape as compressor 426 is drawn proximally. This will allow compressor 426 (and the frictionally engaged ED 412) to gradually decrease in diameter as the compressor 426 is drawn through body portion 506. which may also ensure that frictional engagement of compressor 426 and ED 412 is maintained, thereby reducing or substantially eliminating shifting/slipping of the ED 412 relative to the compressor 426.

In some embodiments, the inner surface 501 of compressor support 50 (and in particular the interior wall 512 of body portion 506) may be coated with a suitable material in order to reduce the friction between inner surface 501 of compressor support 500 and the exterior surface 427 compressor 426. A reduction in friction may be beneficial in ensuring that the compressor 426 is easily compressor 426 is slidably moveable within compressor support 500 and in particular, may be drawn smoothly and evenly through body portion 506.

For the example, the coating on the interior surface of compressor support 500 may include any substance with friction reducing properties, such polytetrafluoroethylene (PTFE) or microceramic. In some embodiments the coating is sprayed on to inner surface 501.

Compressor support 500 may be sized based on the specific dimensions of compressor 426 and ED 412. For example, the internal diameter of the second tubular portion 522 may be selected to be slightly larger than the diameter of ED 412 in the non-compressed position. The internal diameter of body 506 portion may be selected such that the interior wall 512 is complementary to the exterior surface 427 of compressor 426. The internal diameter of proximal body opening 511 may be selected to receive compressor 426 (with or without ED 412 in the compressed position). The internal diameter of first tubular portion 508 may be configured to receive portion of distal delivery sheath end 423 therewithin.

In the embodiments shown in FIGS. 10 and 11 and described above, the interior wall 512 of body portion 506 defines the generally frustoconical shape of insertion bore 507. However, in other embodiments, interior wall 512 may be profiled to define any other suitably shaped internal space that is complimentary to the external surface of the compressor.

In some embodiments, compressor support 500 may be provided prepackaged as depicted in FIG. 10 with ED 412, delivery sheath 422 compressor 426 and push wire 436. In some embodiments, compressor 426 and EB 412 may be urged into delivery sheath 422 (as described above) without removing some or all of the components from the packaging.

Once ED 412 has been received within delivery sheath 422 in a compressed position, the delivery sheath 422 can be used in conjunction with a delivery catheter for delivery of the ED to the target site.

Deployment

Figure 12A:
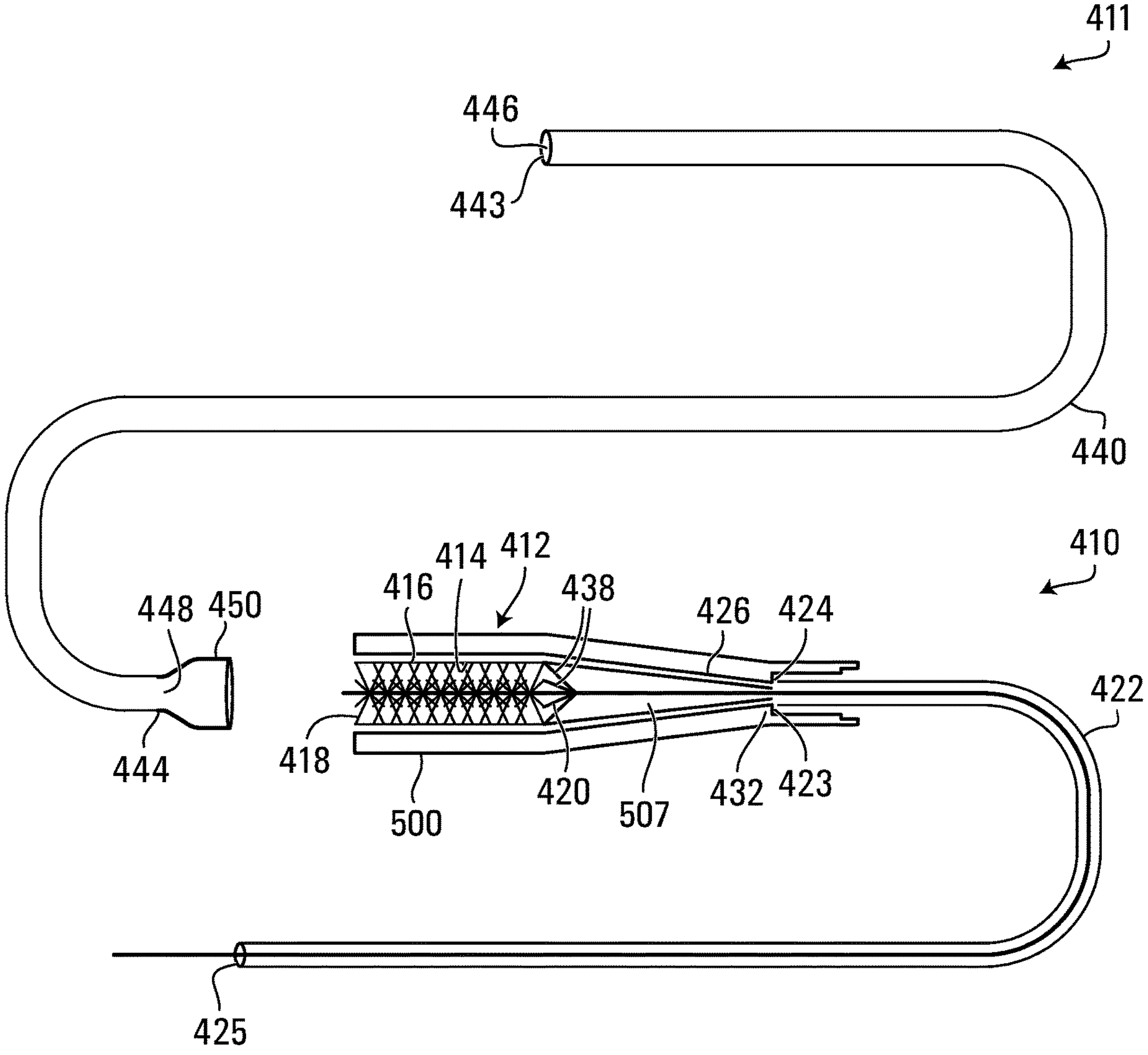
FIG. 12A is a drawing of a system for the deployment of a reversibly compressible endovascular device according to a sixth embodiment of the invention.
Figure 12B:
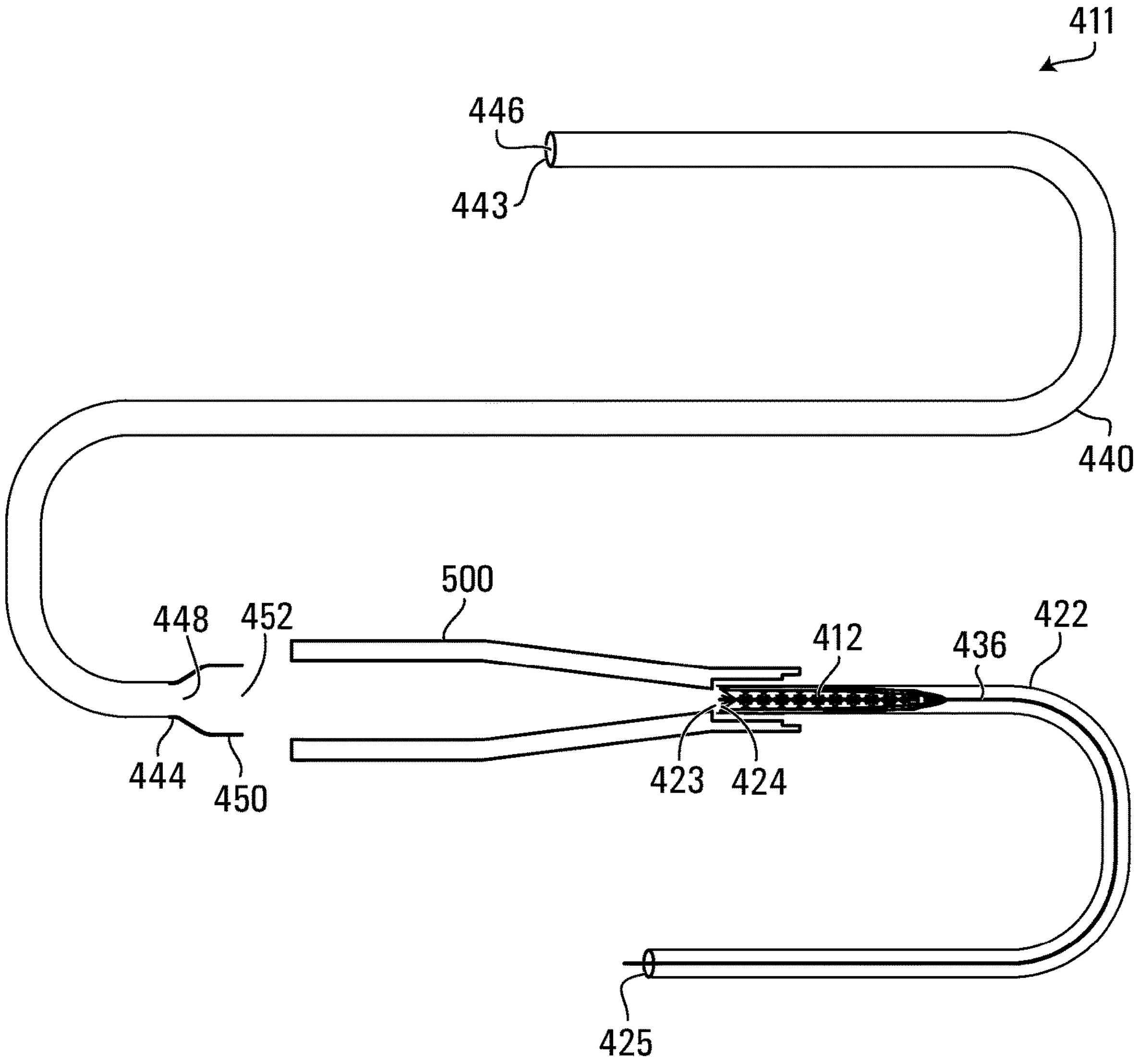
FIG. 12B is a drawing of a system for the deployment of a reversibly compressible endovascular device according to the embodiment illustrated in FIG. 12A, but with the endovascular device compressed within the delivery sheath.

Referring to FIGS. 12A and 12B, a system for deploying a reversibly compressible endovascular device within a lumen of a vessel is shown generally at 411. The system comprises a system for the radial compression of a reversibly compressible endovascular device (ED) prior to deployment as described above with reference to FIG. 10. The system further comprises a delivery catheter 440 having distal and proximal delivery catheter ends 443 and 444 having distal and proximal delivery catheter openings 446 and 448 respectively. Proximal delivery catheter opening 648 is for receiving ED 412 from delivery sheath 422 in a compressed position, whereas distal delivery catheter opening 446 is for deploying ED 412 into the lumen of the vessel. Accordingly, proximal delivery catheter opening 448 is of a width equal to or greater than the width of delivery sheath opening 424.

Figure 12C:
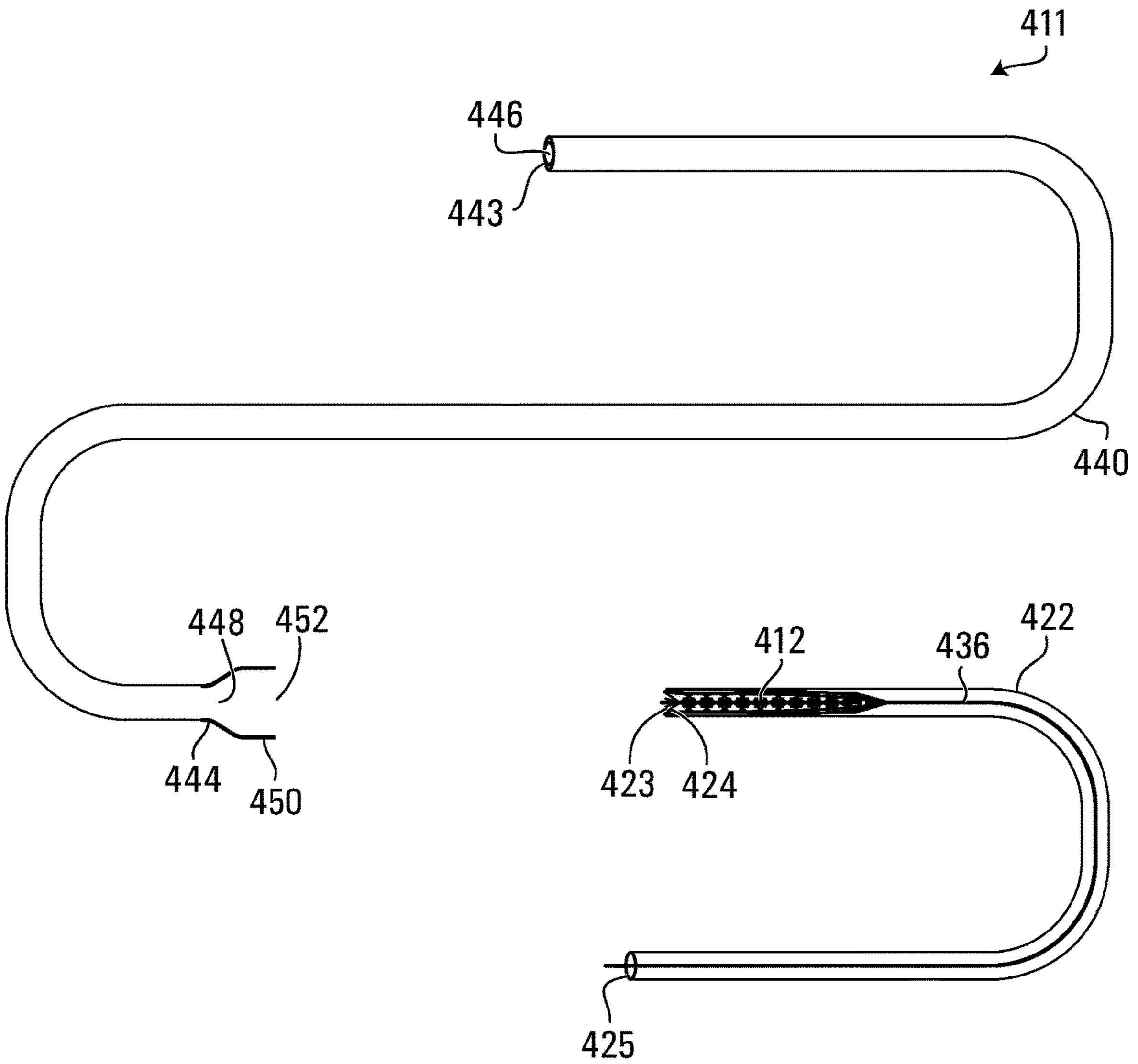
FIG. 12C is a drawing of a system for the deployment of a reversibly compressible endovascular device according to the embodiment illustrated in FIGS. 12A and 12B, but after the compressor support has been removed.
Figure 12D:
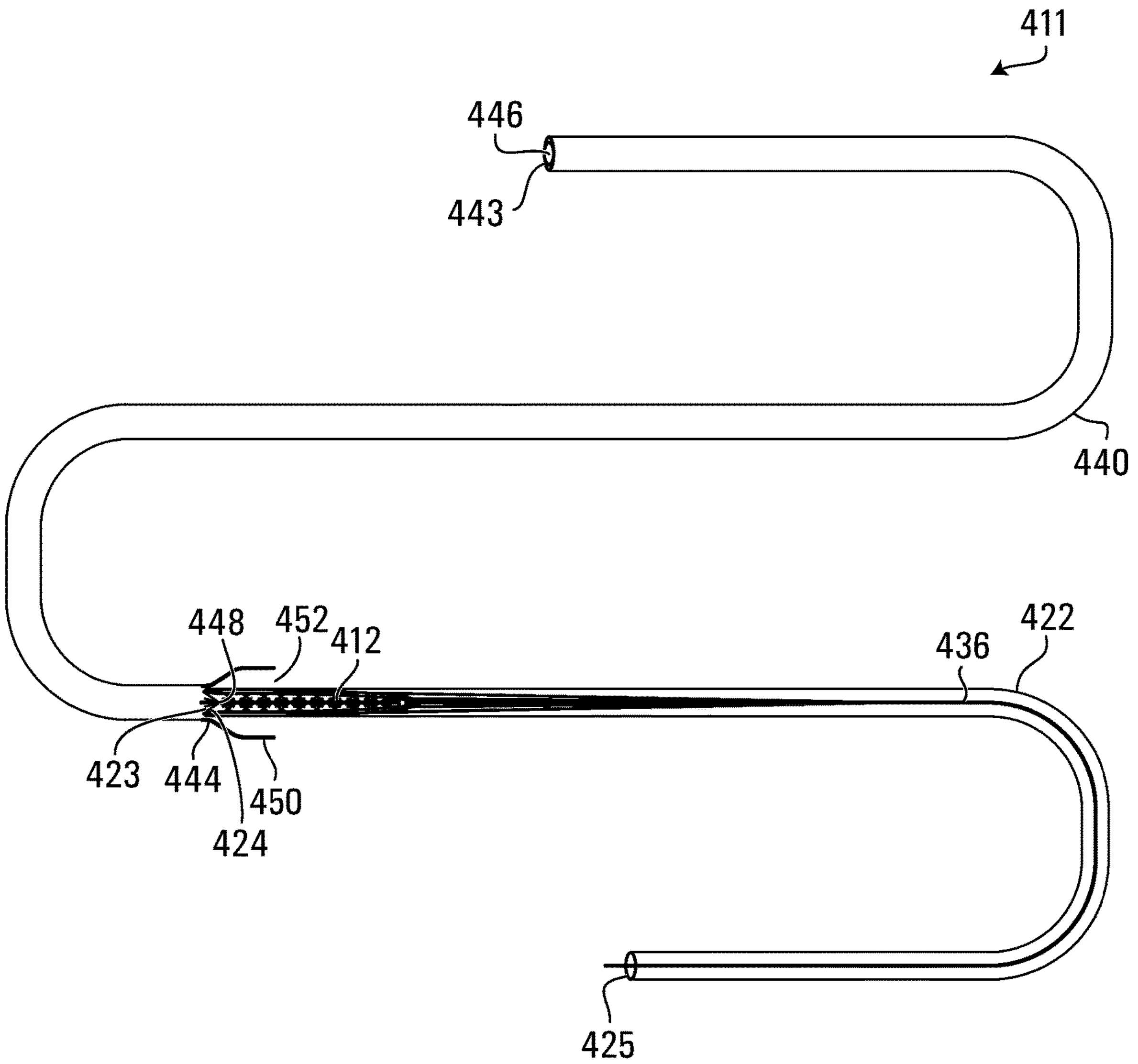
FIG. 12D is a drawing of a system for the deployment of a reversibly compressible endovascular device according to the embodiment illustrated in FIGS. 12A, 12B, and 12C, but with the delivery sheath registered with the delivery catheter prior to transfer of the compressed endovascular device from the delivery sheath to the delivery catheter.

The system further comprises a hub 450 connected to proximal delivery catheter end 444 and in communication with proximal delivery catheter opening 448. Referring to FIG. 12D, hub 450 has hub opening 452 for receiving delivery sheath 422 in hub 450 when compressor 426 and ED 412 are positioned in the delivery sheath. Hub 450 is for positioning delivery sheath opening 424 in abutment with proximal delivery catheter opening 448.

Figure 12E:
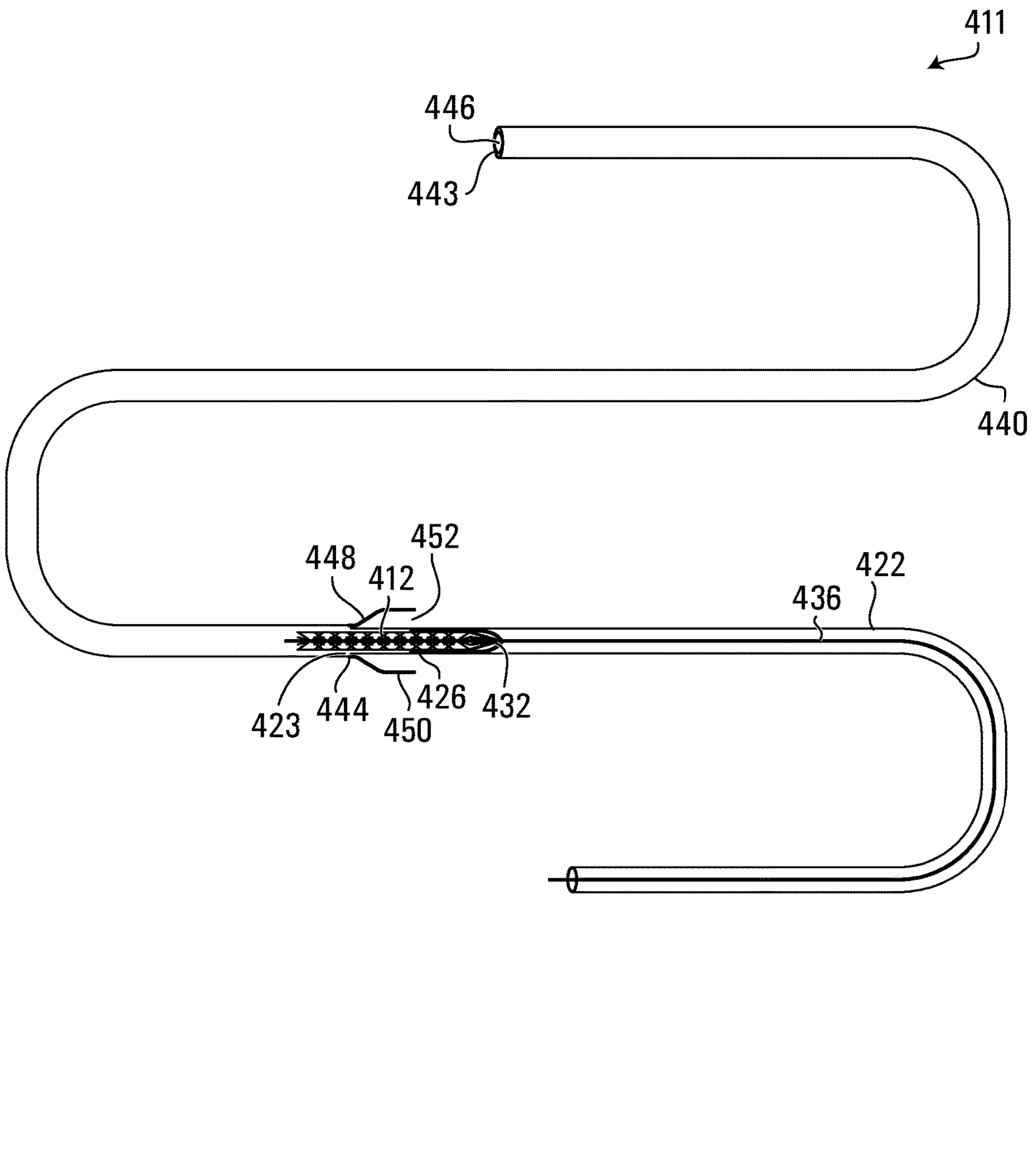
FIG. 12E is a drawing of a system for the deployment of a reversibly compressible endovascular device according to the embodiment illustrated in FIGS. 12A, 12B, 12C and 12D, showing the compressed endovascular device and compressor advanced partially into the delivery catheter through the proximal delivery catheter opening.
Figure 12F:
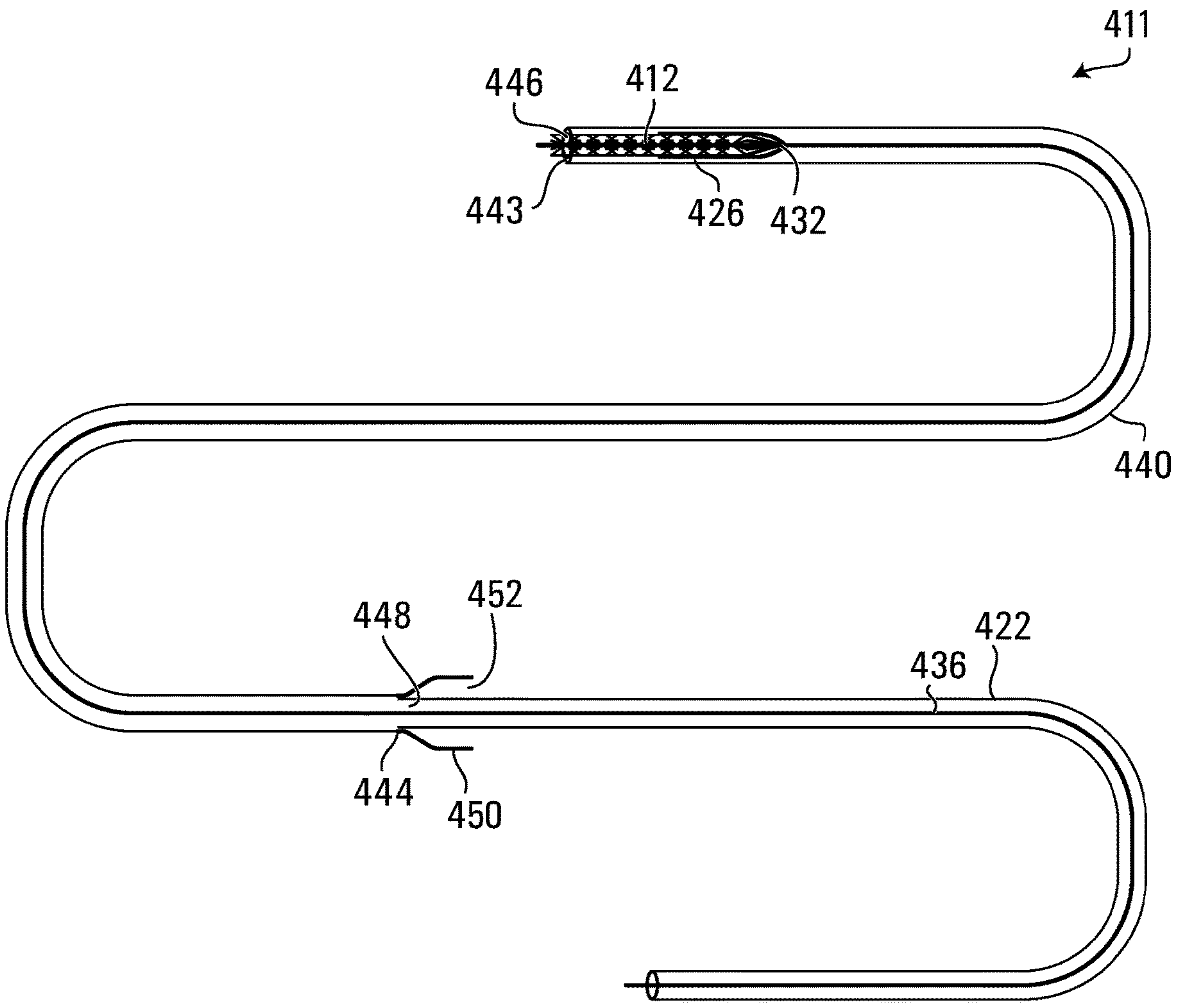
FIG. 12F is a drawing of a system for the deployment of a reversibly compressible endovascular device according to the embodiment illustrated in FIGS. 12A, 12B, 12C, and 12D, showing the compressed endovascular device and compressor advanced to the distal end of the delivery catheter prior to deployment at a target site within a lumen of a subject.
Figure 12G:
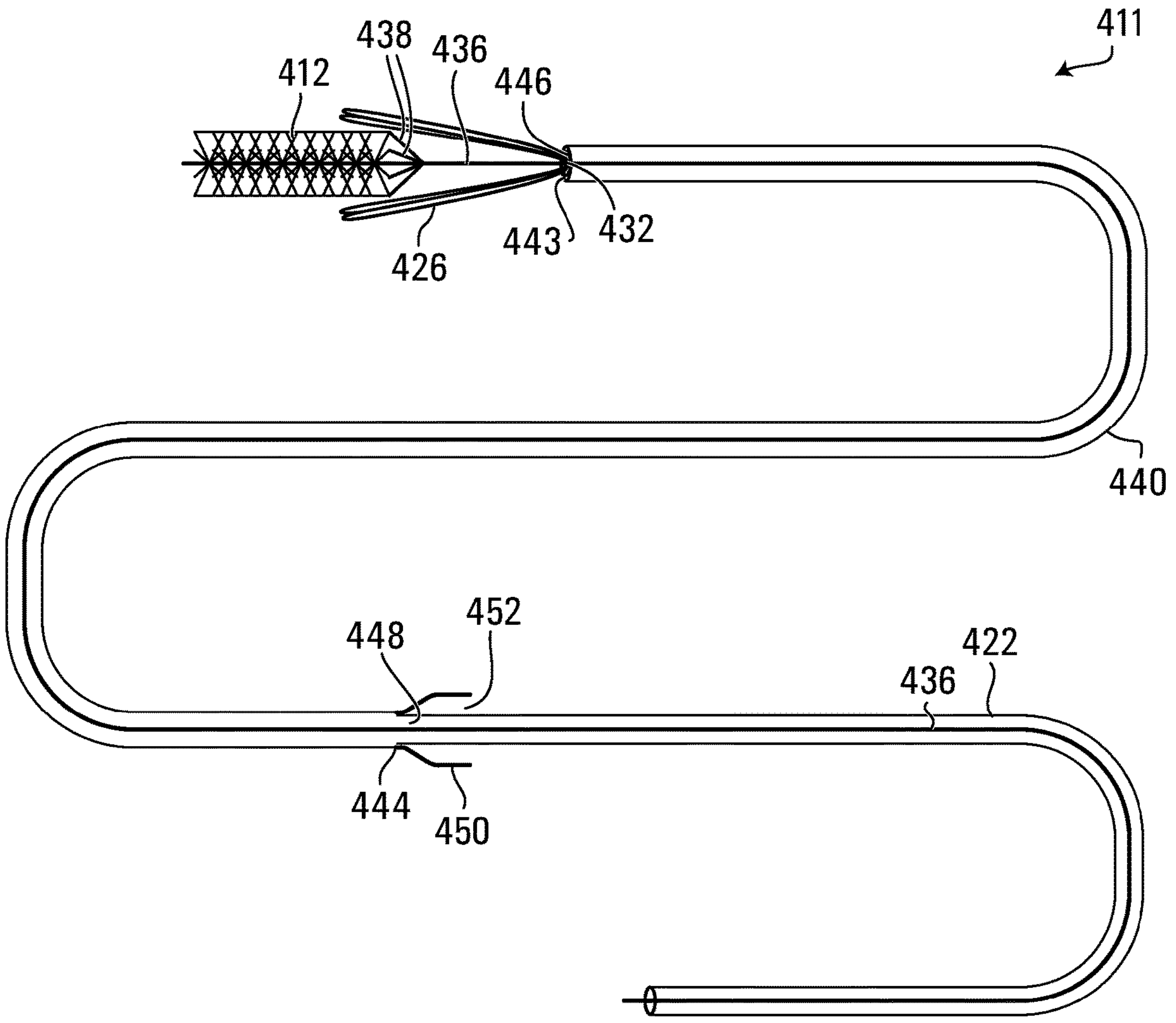
FIG. 12G is a drawing of a system for the deployment of a reversibly compressible endovascular device according to the embodiment illustrated in FIGS. 12A, 12B, 12C, 12D, 12E and 12F, showing the endovascular device and compressor advanced out of the distal delivery catheter opening of the delivery catheter and expanded at the target site within the lumen of a subject.

In operation, delivery catheter 440 will typically be deployed in a vessel of a subject, such that distal delivery catheter end 443 is positioned at a target site, with hub 450 remaining outside of the body of the subject. Referring to FIG. 12B, ED 412 is compressed and loaded in delivery sheath 422 as described above with reference to FIG. 10. Referring to FIG. 12C, compressor support 500 may then be removed, which retracts the distal delivery sheath end 423 from first tubular portion 508, prior to engaging system 410 with delivery catheter 440. Referring to FIG. 12D, distal end 423 of delivery sheath 422, with ED 412 compressed within it, is then inserted in hub 450. Delivery sheath opening 424 is then registered with proximal delivery catheter opening 448. Referring to FIGS. 12E and 12F, push wire 436 is then used to advance compressor 426 and ED 412 distally through the delivery sheath opening 424 into delivery catheter 440 through proximal delivery catheter opening 448, and then distally through the delivery catheter toward distal delivery catheter opening 446. Referring to FIG. 12G, compressor 426 and ED 412 are then advanced through distal delivery catheter opening 446 into the lumen of the vessel where the compressor is expanded to its non-collapsed position. With the expansion of the compressor 426, ED 412 may be expanded in the lumen at the target site.

Figure 12H:
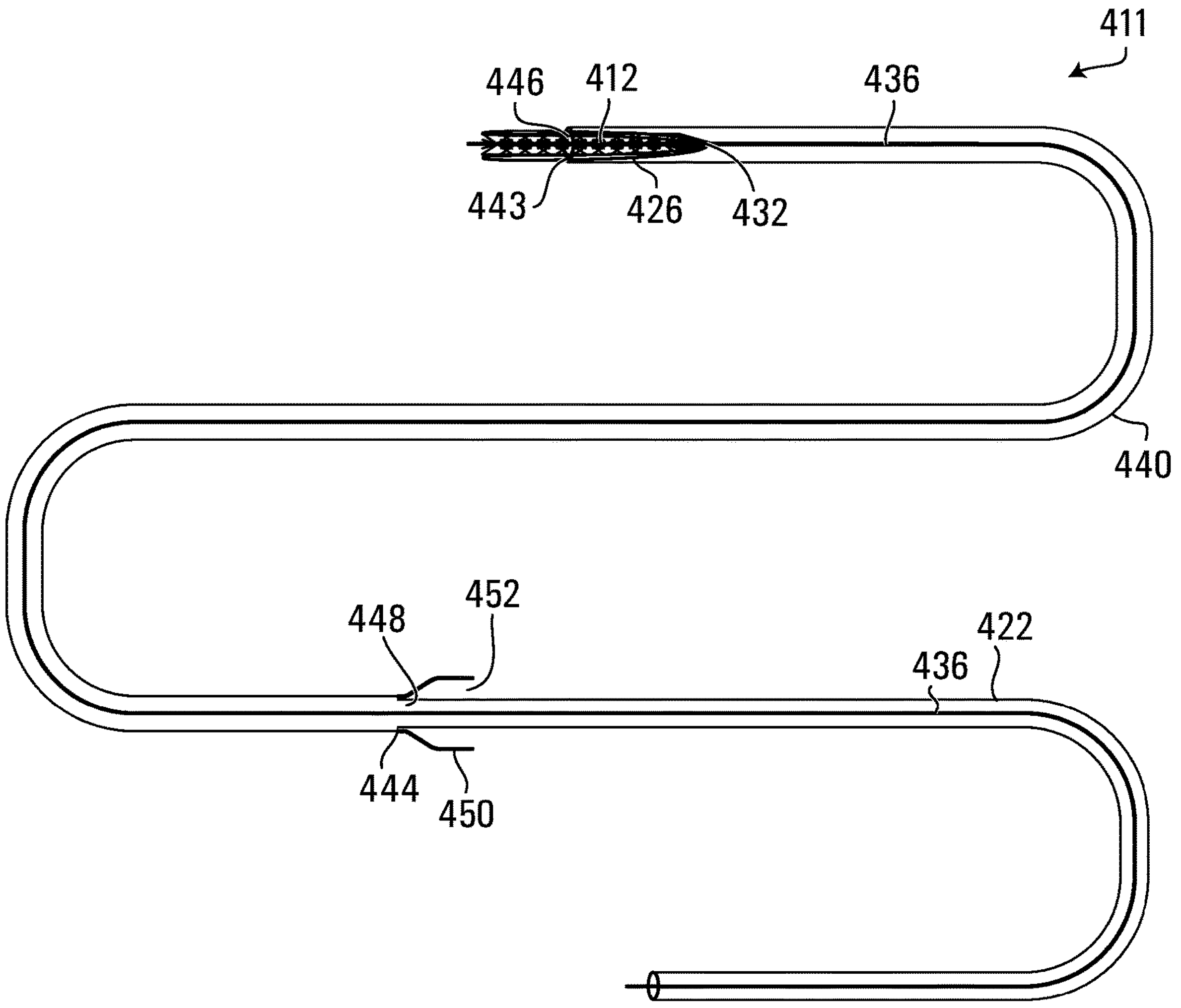
FIG. 12H is a drawing of a system for the deployment of a reversibly compressible endovascular device according to the embodiment illustrated in FIGS. 12A, 12B, 12C, 12D, 12E, 12F and 12G, showing the retraction of an initially deployed endovascular device and compressor into the delivery catheter through the distal delivery catheter opening.

Referring to FIGS. 12G and 12H, push wire 436 is operable to be advanced distally through delivery sheath 422 and delivery catheter 440 to urge compressor 426 and ED 412 out from the delivery sheath through delivery sheath opening and into delivery catheter through proximal delivery catheter opening 448, and through the delivery catheter distally toward and out distal delivery catheter opening 446 into the lumen. Referring to FIG. 12G, once in the lumen at the target site and unconstrained by delivery catheter 440, compressor 426 may be expanded from its collapsed position. This, in turn, permits ED 412 to be expanded to its non-compressed position at the target site.

In embodiments where the compressor is a self-expanding compressor, expanding compressor 426 in the lumen involves allowing the compressor to self-expand. In embodiments where the ED is a self-expanding ED, expanding ED 412 in the lumen similarly involves allowing the ED to self-expand to a non-compressed position. It will be within the purview of a skilled person to select and employ an appropriate means of expanding a compressor or an ED. For example, alternatives for expanding the ED, and/or the compressor, may include inflating a balloon disposed within the tubular body of the ED to expand the ED.

Once in its non-compressed position at the target site, threads 438 may be detached from ED 412, and the delivery catheter may then be repositioned for the deployment of a further ED, or removed. Alternatively, if the embodiment relies on frictional engagement of the compressor with the ED as depicted in FIG. 10, then there is no need to detach any threads.

Alternatively, in embodiments employing threads, it may be desirable to reposition an ED before the threads are detached. In such embodiments, and referring to FIG. 12H push wire 436 is operable to be retracted proximally toward hub 450 to urge deployed ED 412 and expanded compressor 426 back toward the distal delivery catheter opening 446, wherein collapse of compressor 426 upon reception within delivery catheter 440, as with previous reception within delivery sheath 422, exerts a radial force upon ED 412 sufficient to compress the ED for reception in the delivery catheter.

Referring to FIGS. 12G and 12H, if repositioning of ED 412 is desired, push wire 436 is retracted proximally through delivery catheter 440 to urge reversibly collapsible compressor 426 back through distal delivery catheter opening 446 to collapse compressor 426. As with previous loading within delivery sheath 422, as compressor 426 collapses, it exerts a radial force upon ED 112 to compress the ED into a compressed position for reception in delivery catheter 440. Delivery catheter 440 is then repositioned to a second position at target site, or to a second target site. Push wire 436 is again advanced distally to urge compressor 426 and ED 412 out of delivery catheter 440 and into the lumen through distal delivery catheter opening 446. Once compressor 426 is outside of delivery catheter 440, it may again be expanded, thereby allowing ED 412 to be expanded at the second position. Once ED 412 has been satisfactorily positioned within the lumen, threads 438 (as depicted in FIG. 12G) may be detached.

The delivery catheter may then be repositioned for the deployment of a further ED, or removed.

While FIGS. 12D to 12H illustrate the use of compressor supports in connection with embodiments pertaining to repositioning of a deployed or partially deployed ED, where the compressor is advanced distally through the delivery catheter with the ED disposed therein as previously in illustrated in FIGS. 5D to 5G, the skilled person understands that the compressor supports as described herein could be used in connection with embodiments as illustrated in FIGS. 7A to 7D, and particularly where the compressor is retained in the delivery sheath (or removed entirely from the delivery sheath through a proximal opening of the delivery sheath) while the ED is advanced distally into and through the delivery catheter as previously illustrated in FIG. 7D.

Figure 13:
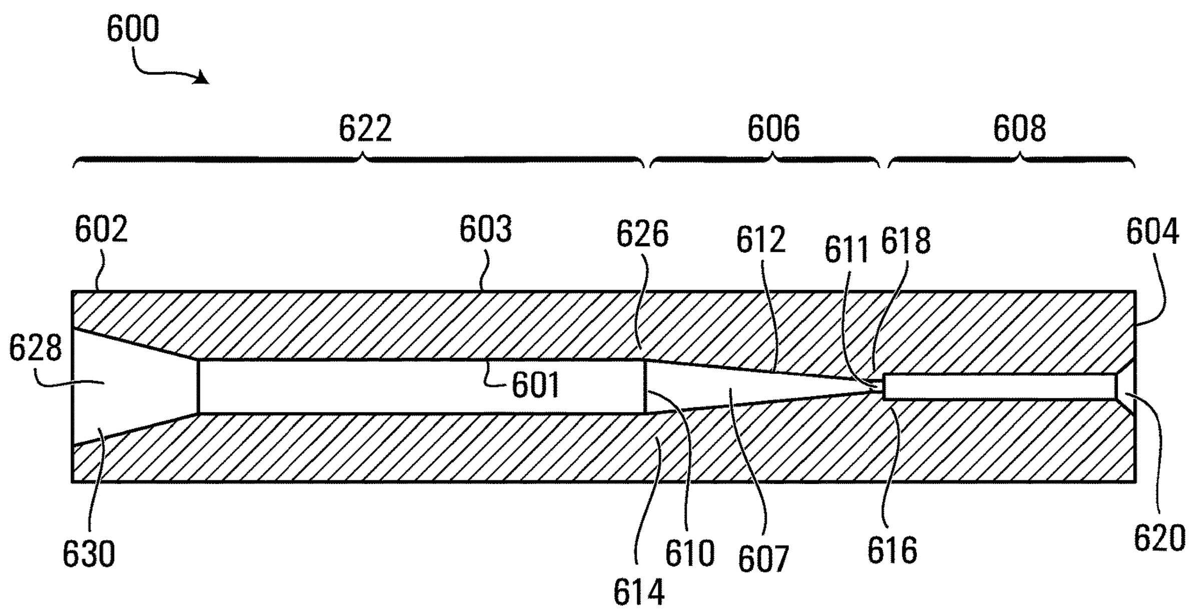
FIG. 13 is a cross sectional side view of a compressor support according to another embodiment of the invention.

With reference to FIG. 13, a compressor support 600 is depicted according to another embodiment. Compressor support 600 may be generally similar to compressor support 500 described above and includes an inner surface 601 and outer surface 603 and distal and proximal ends 602 and 604 respectively. Compressor support 600 also includes a body portion 606, first tubular portion 608 and a second tubular portion 622, which may be configured and operate in similar manner to body portion 506, first tubular portion 508 and second tubular portion 522 described above.

Body portion 606 has distal and proximal ends 614 and 618 respectively and defines a tapered structure with an interior insertion bore 607 comprising a distal compressor support opening 610 and a proximal compressor support opening 611. The interior wall 612 of body portion 606 defines an insertion bore 607 which tapers from the distal end 614 of body portion 606 towards the proximal end 618 of body portion 606 such that the radial cross section of the insertion bore 607 diminishes from distal compressor support end 614 toward the proximal end 618.

First tubular portion 608 extends from a distal end 616 to the proximal end 604 of compressor support 600 and is sized to receive a portion of a delivery sheath (such as delivery sheath 424 therewithin). The proximal end 604 includes a chamfered end 620, which in this embodiment has an increasing internal diameter towards proximal end 618. Similar to region 520 of compressor support 500 described above, chamfered end 620 may assist a user in guiding a sheath into first tubular portion 608.

Compressor support 600 further comprises a second tubular portion 622 extending from distal end 602 of compressor 600 to a proximal end 626 of second tubular portion 622. The Distal end 602 of compressor support 600 comprises a distal tubular portion opening 628 sized to receive a compressor and a ED. Second tubular portion 622 may be generally tubular and may have a length and internal diameter greater than the chosen ED 412 in the non-compressed position.

The distal end 602 of compressor support 600 may include a chamfered end 630, having an increasing internal diameter towards distal second tubular portion opening 628. The enlarged internal diameter at distal second tubular portion opening 628 may assist a user in guiding a compressor (such as compressor 426) and an ED (such as ED 412) in the non-compressed position into second tubular portion 622.

As shown in FIG. 13, compressor support 600 may be configured with a generally cuboidal outer surface 603. This may ensure that compressor support 600 may sit level on a surface and/or may be received in a suitable clamp or holder during use, shipping or storage.

Figure 14:
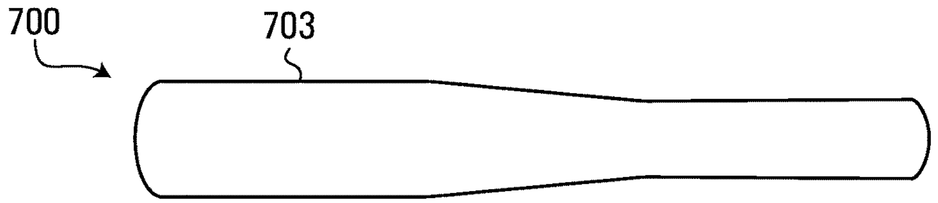
FIG. 14 is a side view of a compressor support according to another embodiment of the invention.

Referring now to FIG. 14, a compressor support 700 is shown according to another embodiment. Compressor support 700 may be configured with an inner surface that is generally similar to compressor support 600 described above and in this embodiment, has an outer surface 702 that generally follows the profile of the inner surface.

In various embodiments, compressor supports may be configured with outer surfaces that are generally similar that of the outer surface 703 of compressor support 700 but may also include a series of protrusions extending from the respective outer surfaces. For example, the compressor support may include an external surface with a series of longitudinally and radially extending protrusions and terminal radially extending protrusions.

Similarly, the compressor support may include an external surface with a radially extending protrusion at a distal end of a second tubular portion and a radial extending protrusion at proximal end of a first tubular portion.

The protrusions of compressors may add additional support and rigidity to the respective compressor, and in embodiments where compressors are made from a transparent material, allow the user to view the insertion bore more clearly. Further, the protrusions may enable or assist the respective compressor to be easier for a user to handle, to sit level on a surface, to be more stable withing any packaging and/or be received in a suitable clamp or holder during use, shipping or storage.

Figure 15:
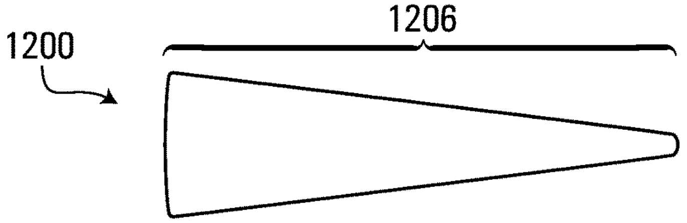
FIG. 15 is a side view of a compressor support according to another embodiment of the invention.

In some embodiments, the compressor support may not include a first tubular portion (such as for example first tubular portion 508 described above) and/or a second tubular portion (such as, for example tubular second portion 522 described above). With reference to FIG. 15, a compressor 1200 is shown according to another embodiment. Compressor 1200 may include a body portion 1206, having a generally conical outer profile and a generally corresponding conical inner profile which functions in a similar manner to body 506 of compressor 500 as described above.

The compressor supports of the present disclosure may be manufactured from any suitable material such as suitable material such as plastic, metal, glass or any combinations thereof. The material of the compressor supports of the present disclosure may be selected from any material that is suitably strong rigid to provide an interior wall (as described above) that will not deform as the compressor is drawn through the body portion of the compressor support.

In addition, the compressor supports of the present disclosure may be formed as a unitary structure by means of manual fabrication, extrusion, mold injection, casting, 3D printing, CNC fabrication or templating.

In some embodiments, the compressor supports of the present disclosure may be made from a plastic sheet or film, including, but not limited to, a polyester (in particular polyethylene terephthalate, PET, polybutylene terephthalate, PBT, polyethylene naphthalate, PEN, polylactic Acid, PLA, polyhydroxybutyrate and their copolymers), polyamide (in particular PA 6, PA 6.6, PA 6.10, PA 6.12, PA 11, PA 12 and their copolymers), polyethylene (PE) in all its variations, based on density, molecular weight or branching (for example: low, medium or high density, linear or branched, high, ultra-high, low, ultra-low molecular weight and all their combinations), polypropylene, polycarbonate (PC), polystyrene (PS), polymethylmethacrylate (PMMA, including its modifications with comonomers such as methacrylic acid, acrylate, butyl acrylate), acrylonitrile butadiene styrene (ABS), polyvinylchloride, polyether sulfone, polyetherether ketone, polyetherimide, polyphenyleneoxide and other less common grades of plastic sheets or film.

In some embodiments, the compressor support in manufactured from a transparent or partially transparent material. This may beneficially allow a user to view the compressor, ED, push wire and/or delivery sheath within the collapsible compressor during use. For example, a user may be able to visually verify the that compressor and ED has been successfully compressed and drawn into the delivery sheath.

Figure 16:
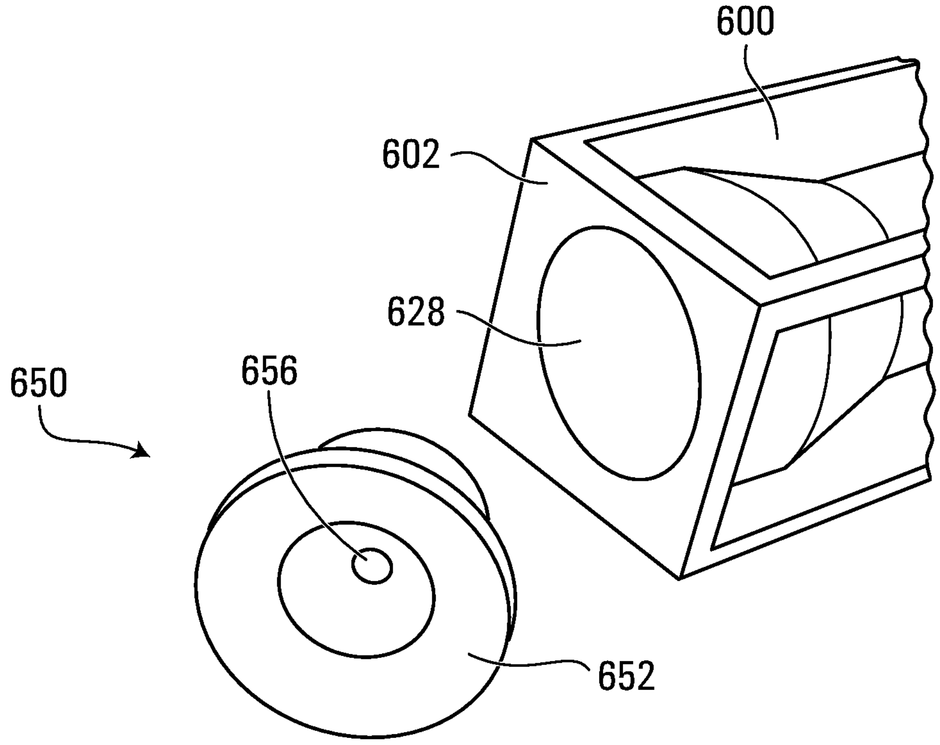
FIG. 16 is a perspective view of part of the compressor support of FIG. 13, with an uninstalled end cap according to an embodiment.
Figure 17:
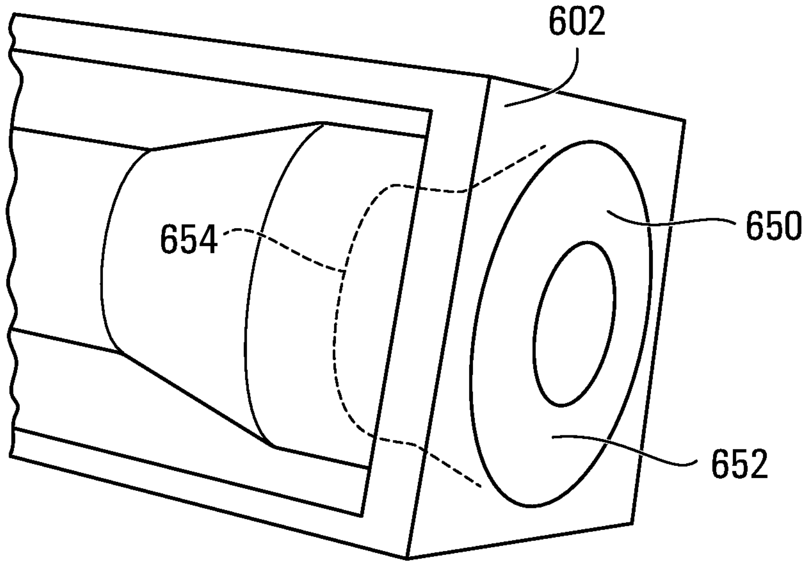
FIG. 17 is a perspective view of the compressor support and end cap of FIG. 16, with the end cap installed.

As described above, the compressor supports of the present disclosure may be used to house an ED and a collapsible compressor during shipping and storage. With reference to FIGS. 16 and 17, in some embodiments, compressor support 600 may include an end cap 650. End cap 650, having distal and proximal ends 652, 654 respectively and is configured and sized to be received within a distal second tubular portion opening 628 of compressor 600 and functions to prevent any dirt, debris or contaminants for entering the interior of compressor support 600.

End cap 650 also includes an opening 656 located generally centrally on end cap 650 and extending from distal end 652 to proximal end 654. Opening 656 is sized to receive a push wire (such as push wire 436 described above) therethrough. Similar to as described above, the push wire may be attached to an ED, the ED being located within second tubular portion 622 of compressor support 600. As a result of passing the push wire though opening 656 in end cap 650, the push wire is supported by end cap 650, thus undesirable movement of push wire and the attached ED may be prevented or substantially reduced until end cap 650 is removed. This may prevent shifting and or damage to the ED during shipping, for example.

In another embodiment, the end cap may be configured to slidingly engage the radially extending protrusion at the distal end of a second tubular portion of compressor support. The end cap may include an inner cavity with an opening at the lower end sized to receive protrusion. A vertically extending slot in the end cap 950 may be configured to accommodate a push wire (or any other components extending through the distal second tubular portion opening of the compressor support 900. The slot may provide support to a push wire (similar to the opening 656 of end cap 650 described above), whilst may also easily installed and removed from the compressor support without disturbing the push wire.

It will be apparent to a skilled person that an end cap, similar to end cap 650 described above, may be used with any of the compressor supports of the present disclosure. The end caps may be manufactured from the same material as the compressor support, or from different materials, such as plastic or rubber.

Figure 18A:
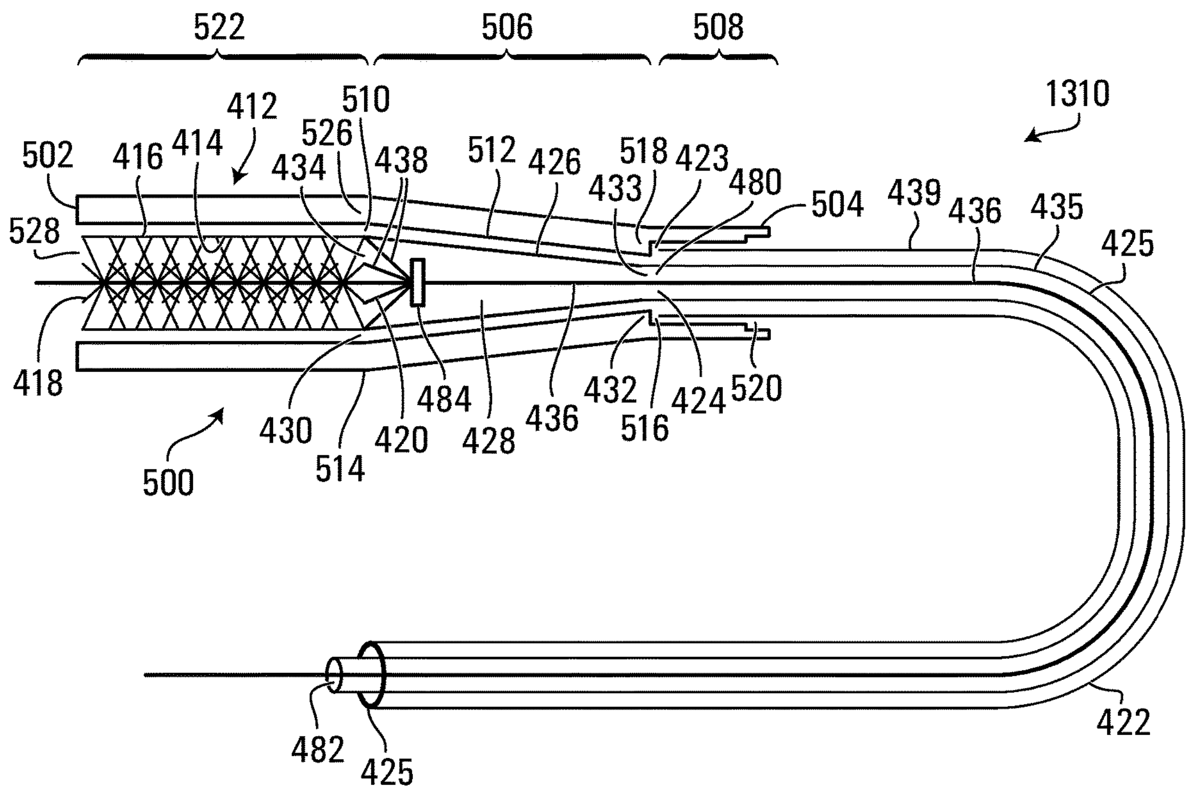
FIG. 18A is a drawing of a system for the radial compression of a reversibly compressible endovascular device prior to deployment according to a seventh embodiment of the invention.

Referring to FIG. 18A, a system for the radial compression of a reversibly compressible endovascular device (ED) prior to deployment according to a fourth embodiment of the invention is shown generally at 1310. The system includes a reversibly compressible ED 412 as are generally known in the art. In general, the ED comprises a tubular body that is expandable between a non-compressed position, as depicted in FIG. 18A, and compressed position for loading within a catheter for delivery to a target site in the lumen of a vessel within the body of a subject. The tubular body has an inner surface 414, an outer surface 416, and opposed distal and proximal ED openings 418 and 420.

The system further includes a delivery sheath 422 sized to receive and maintain the ED 412 in the compressed position upon reception in the delivery sheath 422 in the compressed position. Delivery sheath 422 has a distal delivery sheath end 423 having a delivery sheath opening 424. Delivery sheath opening 424 has a width sized to receive the ED 412 into delivery sheath 422 in a compressed form. Delivery sheath 422 further has a proximal delivery sheath end 425.

The system further includes a compressor 426 for radially compressing the ED 412 for reception by the delivery sheath 422 through the delivery sheath opening 224. The compressor may be configured similar in a similar manner to compressors 126, 226 described above and includes a generally tapered structure defining an interior space 428 in which ED 412 initially is at least partially positioned in a non-compressed position. The tapered structure comprises distal and proximal compressor ends 430 and 432.

Distal compressor end 430 comprises a distal compressor opening 434 sized to receive ED 412 in the non-compressed position. As illustrated in FIG. 18A, compressor 426 tapers from distal compressor opening 434 toward proximal compressor end 432 such that the radial cross section of the interior space 428 diminishes from distal compressor end 430 toward proximal compressor end 432. The width of proximal compressor end 432 is less than the width of delivery sheath opening 424 such that proximal compressor end 432 is sized to be received within delivery sheath 422 as discussed below.

Compressor 426 is collapsible, such that as it collapses, the cross sectional area of interior space 428 at any position along the longitudinal axis of the compressor from distal compressor end 430 to proximal compressor end 432 progressively decreases. As the cross sectional area of interior space 428 decreases, compressor 426 exerts a radial force against ED 412 positioned therein to compress the ED 412.

Compressor 426 is sized to be received, in collapsed form, within delivery sheath 422 through delivery sheath opening 424. ED 412, being compressed within interior space 428 as compressor 426 collapses, is thereby compressed for reception within delivery sheath 422.

The system further comprises means for urging compressor 426 and ED 412 proximally toward distal delivery sheath end 423 and into delivery sheath 422 through delivery sheath opening 424. The means for urging the compressor and the ED 412 proximally (or distally as the case may be) may further comprise independent means for urging the ED independently of the compressor.

Referring still to FIG. 18A, the means for urging compressor 426 and ED 412 according to this particular embodiment include a compressor wire 435 that is attached to proximal compressor end 432, which may be drawn proximally toward proximal delivery sheath end 425 to urge compressor 426 toward distal delivery sheath end 423. In this embodiment, compressor wire 435 is a hollow, tubular wire having distal and proximal compressor wire openings 480 and 482. Distal compressor wire opening 480 is in communication with a proximal compressor opening 433 at proximal compressor end 432.

In the embodiment illustrated in FIG. 18A, the means for urging compressor 426 and ED 412 further comprises a push wire 436 that is attached to the ED, but is not attached to the compressor. Push wire 436 is positioned within compressor wire 435 and extends through distal compressor wire opening 480 and proximal compressor opening 433, and is detachably attached to ED 412. Push wire 436 is attached to ED 412 by at least one (i.e. one or more) threads 438. In FIG. 18A, threads 438 are shown radiating from push wire 436 and attached to ED 412 at proximal ED opening 420. However, the skilled person understands that threads 438 may be attached to ED 412 at a different position, for example, to inner surface 414 or outer surface 416. In some embodiments, threads 438 could be attached at distal ED opening 418. In some embodiments, the at least one thread is a single thread comprising a lasso, wherein the lasso is looped and tightened around the tubular body of the ED proximal to proximal ED opening to form a cincture about the proximal end of the ED.

As discussed above, threads 438 may be electrolytically or mechanically detachable from ED 412 once the ED is positioned at the target site within the lumen of the vessel, as is known in the field. In embodiments involving a lasso-style attachment, the loop of the lasso may be broken to release ED. Threads 438 may be made of any suitable materials as are known in the field, including wires.

Thus, the skilled person will understand that compressor wire 435 and push wire 436 allow for the compressor 426 and the ED 412 to be moved independently of each other. For example, as described below, in situations where it is not desirable to deploy the compressor 426 into the lumen of vessel at the target site, push wire 436 may be advanced distally while compressor wire 435 is maintained in position or advanced proximally.

Referring again to FIG. 18A, the means for urging ED 412 further comprise a bump member 484 (which may be similar to bump member 284 described above) disposed on push wire 436 between threads 438 and proximal compressor opening 433. When compressor wire 435 is held in a static position, or retracted proximally through delivery sheath 422, while push wire 436 is advanced distally, bump member 484 abuts the proximal end of ED 412 at ED opening 420 to apply a force uniformly across the circumference of the ED 412 at the proximal end opening to urge the ED distally while the compressor 426 remains in position or is retracted proximally. In this way, ED 412 may be disengaged from the compressor 426.

In the illustrated embodiment, the bump member abuts the proximal end of ED 412 to urge the ED distally as push wire 436 is advance distally. However, the skilled person will understand that the bump member could be positioned at least partially within the ED through the proximal ED opening, such that a radially outer surface of the bump member can engage, e.g. frictionally engage, the inner surface of the ED, e.g. inner surface 414 of ED 412 to urge the ED distally as push wire 436 is advance distally. A skilled person will appreciate that a number of bumper structures could be used in the context of the presently disclosed invention in combination with a push wire to urge an ED distally independently of a compressor. For example, the skilled person will be aware of bumps, including a dual function bump, as disclosed in U.S. Pat. No. 10,292,851. Alternatively, a stent bed as described in U.S. Pat. No. 10,555,824 could be used as a bumper in the context of the presently disclosed invention.

Similar to system 410, system 1310 further includes a compressor support 500 (shown in isolation and as described above in relation to FIGS. 10 and 11).

Figure 18B:
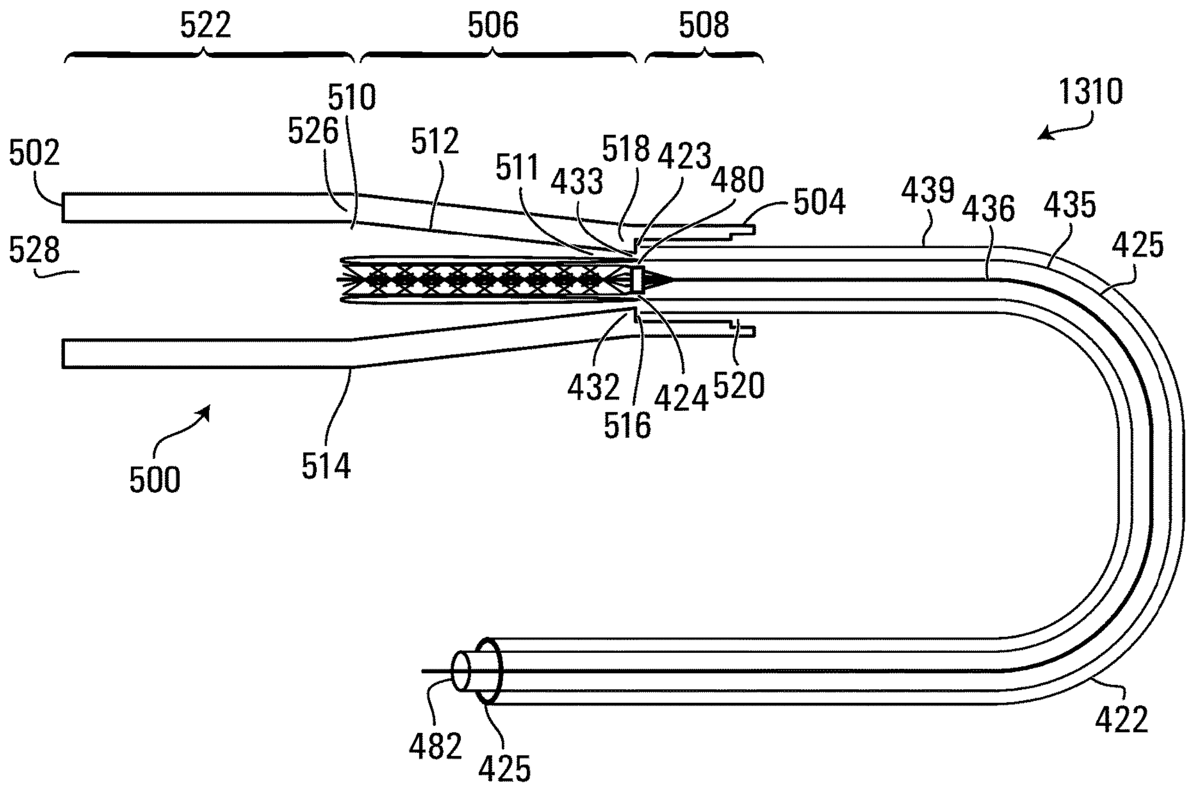
FIG. 18B is a drawing of the system depicted in FIG. 18A with the compressor and endovascular device partially received within the delivery sheath.

Referring to FIG. 18B, compressor wire 435 and push wire 436 are operable to be retracted proximally in conjunction through delivery sheath 422 toward proximal delivery sheath end 425 to urge compressor 426 through compressor support 500 into delivery sheath 222 through delivery sheath opening 424. In various embodiments, an inner wall 239 of delivery sheath 422 is operable to exert a force against the outer surface of compressor 426, as compressor 426 is received within the delivery sheath 422, that is sufficient to collapse the tapered structure.

As depicted in FIG. 18A, compressor 426 may take the general form of a funnel. In some embodiments, compressor 226 may comprises a plurality of overlapping tongues (similar to tongues 242 if of compressor 226 described above) coupled at proximal compressor end 432.

However, the skilled person will again understand that collapsible compressors according to the present disclosure could include a variety of radially compressible structures that, when at least partially received within the delivery sheath, form a tapered structure that can accommodate an ED in noncompressed form and, as urged into the delivery sheath along with the ED, collapse to compress the ED to a compressed form. Such compressors could be formed of a braided structure, for example, a polypropylene braided or a metal braided structure as is known in the art and used in some cases for the fabrication of EDs themselves.

In various embodiments, compressor 426 is reversibly collapsible. For example, compressor 426 may be resiliently deformable such that, after reception in delivery sheath 422, it may be urged distally using compressor wire 435 from the delivery sheath into a delivery catheter, and then out of the delivery catheter through a distal delivery catheter opening (e.g. into the lumen of a vessel), at which time it will expand to a non-collapsed formation to permit release of ED 412 at the target site. Alternatively, the tapered structure may be actively expanded upon emergence from a delivery catheter opening by any means known in the art, e.g. using a balloon.

Alternatively, push wire 436 may be used to urge ED 412 distally independently of compressor 426, such that compressor 436 may remain in delivery sheath 422 (or delivery catheter, as the case may be) while ED 412 is advanced through a delivery catheter for deployment at a target site In operation, starting with ED 412 in an expanded position, retracting compressor wire 435 and push wire 436 into delivery sheath 222 toward proximal delivery sheath end 425 urges compressor 426 into body portion 506 though distal body opening 510. Continued retraction of compressor wire 435 and push wire 436 into delivery sheath 422 urges compressor 426 into delivery sheath 422 through delivery sheath opening 424.

As compressor 426 is urged into delivery sheath 422, the cross sectional area of interior space 428 at any position along the longitudinal axis of the compressor from distal compressor end 430 to proximal compressor end 432 is progressively reduced, wherein compressor 426 exerts a radial force against ED 412 positioned therein to radially compress the ED for reception within delivery sheath 422 through delivery sheath opening 424.

The interior wall 512 of body portion 506 provides lateral support to the exterior surface of the compressor 426 as the compressor 426 is drawn proximally through the proximal opening of body portion 506 and into delivery sheath 422 through delivery sheath opening 424. The lateral support provided by interior wall 512 may ensure that the strength of frictional engagement between the compressor 426 and ED 412 is maintained as compressor 426 is drawn proximally, such that shifting/slipping of the ED 412 relative to the compressor 426 is reduced or substantially eliminated. Further, the gradual and consistent taper of interior wall 512 (as described above) ensures that the compressor 426 maintains a complementary gradual and consistent tapered shape as compressor 426 is drawn proximally. This will allow compressor 426 (and the frictionally engaged ED 412) to gradually decrease in diameter as the compressor 426 is drawn through body portion 506. which may also ensure that frictional engagement of compressor 426 and ED 412 is maintained, thereby reducing or substantially eliminating shifting/slipping of the ED 412 relative to the compressor 426.

Once ED 412 has been received within delivery sheath 422 in a compressed position, compressor support 500 is then removed from engagement with delivery sheath 422. More particularly, the bump member comprises a circular contact surface having a diameter sized to contact the ED at the proximal ED end about a circumference of the proximal ED end of the ED in the compressed position. The bump member may be configured so that a distal face of the bump member contacts the ED at the proximal ED end, wherein the bump member is not required to be engaged with the ED during compression by the collapsible compressor. The bump member may be configured to be advanced distally relative to the compressor in order for the contact surface to contact the proximal ED end and apply a distal force at the proximal ED end about the circumference of the proximal ED end only in a distal direction in order for the ED to be disengaged from the compressor.

The sheath 422 can be used in conjunction with a delivery catheter (such as delivery catheter 240 described above) for delivery of the ED to the target site in a similar manner to as described above in relation to FIGS. 7A, 7B, 7C and 7D.

In some embodiments, compressor support 500 may be provided prepackaged as depicted in FIG. 18A with ED 412, compressor wire 435 delivery sheath 422 compressor 426 and push wire 436. In some embodiments, compressor 426 and EB 412 may be urged into delivery sheath 422 (as described above) without removing some or all of the components from the packaging.

Operation

While specific embodiments of the invention have been described and illustrated, such embodiments should be considered illustrative of the invention only and not as limiting the invention as construed in accordance with the accompanying claims.

All documents referred to herein, including patent application publications, patents, and other publications are incorporated by reference in their entirety.

Embodiments

1. A system for the radial compression of a reversibly compressible endovascular device (ED) prior to deployment, the system comprising:

the ED, wherein the ED comprises a tubular body, wherein the body is expandable between a compressed position and an non-compressed position, the tubular body having an inner surface, an outer surface, and opposed distal and proximal ED openings;

a delivery sheath sized to receive and maintain the ED in the compressed position, the delivery sheath having a delivery sheath opening having a width sized to receive the ED into the delivery sheath in a compressed form;

a compressor for compressing the ED for reception by the delivery sheath through the delivery sheath opening, wherein the compressor comprises:

a generally tapered structure defining an interior space, the tapered structure comprising distal and proximal compressor ends, wherein the proximal compressor end is proximal to the delivery sheath opening, wherein the distal compressor end comprises a distal compressor opening sized to receive the ED in the non-compressed position, wherein the tapered structure tapers from the distal compressor opening toward the proximal compressor end such that the cross section of the interior space diminishes toward the proximal compressor end, wherein the cross sectional area of the interior space at the second end is equal to or less than the cross sectional area of the delivery sheath opening; and a push wire detachably attached to the ED and disposed within the delivery sheath, wherein the push wire is operable to be advanced proximally through the delivery sheath to urge the ED through the compressor, whereby the ED is deformed into the compressed position as it is urged proximally through the compressor.

2. The system of embodiment 1, wherein the compressor comprises a second compressor opening at the second compressor end.

3. The system of embodiment 2, wherein the second compressor opening is in communication with the delivery sheath opening 4. The system of embodiment 2 or 3, wherein the width of the second compressor opening is smaller than the radial diameter of the ED when the ED is in the non-compressed position.

5. The system of embodiment 2, 3, or 4, wherein the push wire is disposed within the ED through the second compressor opening.

6. The system of any one of embodiments 2 to 5, wherein the push wire is operable to be advanced proximally through the delivery sheath to urge the ED through the second compressor opening and into the delivery sheath.

7. The system of any one of embodiments 1 to 6, wherein the compressor is a funnel.

8. The system of any one of embodiments 1 to 7, wherein the tapered structure comprises a unitary body.

9. The system of any one of embodiments 1 to 8, wherein the push wire is detachably attached to the ED by one or more threads.

10. The system of embodiment 9, wherein the one or more threads are attached to the inner surface of the ED.

11. The system of 9 or 10, wherein the one or more threads are electrolytically detachable from the ED.

12. The system of embodiment 9 or 10, wherein the one or more threads is a single wire comprising a lasso looped around the tubular body at a proximal end of the ED.

13. The system of embodiment 9, 10, or 12, wherein the one or more threads are mechanically detachable from the ED.

14. The system of any one of embodiments 1 to 13, wherein the compressor is detachable.

15. The system of any one of embodiments 1 to 3, wherein the compressor is collapsible.

16. The system of any one of embodiments 1 to 3, wherein the compressor is reversibly collapsible.

17. The system of embodiment 15 or 16, wherein the compressor comprises a braided structure.

18. The system of embodiment 17, wherein the braided structure is a polypropylene braided structure.

19. The system of embodiment 17, wherein the braid structure is a metal braided structure.

20. The system of embodiment 15 or 16, wherein the tapered structure comprises a plurality of overlapping tongues coupled at the second compressor end, wherein each tongue tapers toward the second compressor end.

21. The system of embodiment 15, 16, or 20, wherein the second compressor end is sized to be received within the delivery sheath through the delivery sheath opening.

22. The system of embodiment 21, wherein the compressor is sized to be received within the delivery sheath when the compressor is in a collapsed position.

23. The system of embodiment 22, wherein an inner wall of the delivery sheath is operable to exert a force against the side of the tapered structure, as the compressor is received within the delivery sheath that is sufficient to collapse the compressor.

24. The system of any one of embodiments 14 to 23, wherein the push wire is attached to the compressor, wherein the compressor is attached to the ED by one or more threads.

25. The system of embodiment 24, wherein the one or more threads are attached to the inner surface of the ED.

26. The system of 24 or 25, wherein the one or more threads are electrolytically detachable from the ED.

27. The system of embodiment 24 or 25, wherein the one or more threads are mechanically detachable from the ED.

28. The system of embodiment 24 or 25, wherein the one or more threads is a single wire comprising a lasso looped around the tubular body at a proximal end of the ED.

29. The system of any one of embodiments 14 to 23, wherein the push wire is attached to the compressor, wherein an interior surface of the tapered structure is operable to frictionally engage the outer surface of the ED.

30. The system of any one of embodiments 14 to 29, wherein the push wire is operable to be advanced proximally through the delivery sheath to urge the ED and the compressor toward the delivery sheath, whereby collapse of the compressor upon reception within the delivery sheath exerts a radial force upon the ED sufficient to compress the ED for reception in the delivery sheath.

31. The system of any one of embodiments 14 to 23, wherein the push wire is detachably attached to the ED by one or more threads.

32. The system of embodiment 31, wherein the one or more threads are attached to the inner surface of the ED.

33. The system of embodiment 31 or 32, wherein the one or more threads are electrolytically detachable from the ED.

34. The system of embodiment 31 or 32, wherein the one or more threads is a single wire comprising a lasso looped around the tubular body at a proximal end of the ED.

35. The system of embodiment 31, 32, or 33, wherein the one or more wires are mechanically detachable from the ED.

36. The system of any one of embodiments 31 to 35, wherein an interior surface of the tapered structure is operable to frictionally engage the outer surface of the ED.

37. The system of any one of embodiments 31 to 36, further comprising a hollow compressor wire attached to the compressor and disposed within the delivery sheath, wherein the compressor wire is operable to be advanced through the delivery sheath to urge the compressor through the delivery sheath opening to collapse the compressor, whereby the ED is deformed into the compressed position as the compressor collapses as the ED and the compressor are urged through the delivery sheath opening.

38. The system of embodiment 37, wherein the push wire is disposed within the compressor wire, wherein the push wire is operable to be advanced through the delivery sheath independently of the compressor wire to urge the ED independently of the compressor.

39. The system of embodiment 37 or 38, further comprising a bump member disposed on the push wire between the ED and the compressor, wherein the bump member is for abutting the ED along the circumference of the proximal ED opening to urge the ED distally through the delivery sheath when the push wire is advanced distally through the delivery sheath.

40. The system of embodiment 37, 38, or 39, wherein the push wire and compressor wire are operable to be advanced proximally through the delivery sheath to urge the ED and the compressor toward the delivery sheath, whereby collapse of the compressor upon reception within the delivery sheath exerts a radial force upon the ED sufficient to compress the ED for reception in the delivery sheath.

41. The system of any one of embodiments 1 to 40, wherein the ED is a self-expanding ED.

42. A system for deploying a reversibly compressible endovascular device within a lumen of a vessel, the system comprising:

- a system for the radial compression of a reversibly compressible endovascular device (ED) prior to deployment as defined in any one of embodiments 1 to 41;
- a delivery catheter comprising proximal and distal delivery catheter openings, wherein the distal delivery catheter opening is for deploying the ED in to the lumen, and wherein the proximal delivery catheter opening is for receiving the ED from the delivery sheath, wherein the proximal delivery catheter opening is of a width equal to or greater than the width of the delivery sheath opening; and
- a hub connected to the proximal delivery catheter opening, the hub having a hub opening for receiving the delivery sheath in the hub when the ED is positioned in the delivery sheath, and positioning the delivery sheath in abutment with the proximal delivery catheter opening, wherein the push wire is operable to be advanced through the delivery catheter to urge the ED through the delivery catheter and out distal delivery catheter opening.

43. The system of embodiment 42, wherein the push wire is operable to be advanced through the delivery catheter to urge the compressor through the delivery catheter and out the distal delivery catheter opening, wherein the compressor is operable to expand.

44. The system of embodiment 42 or 43, wherein the push wire is operable to be retracted toward the hub to urge a deployed ED and expanded compressor toward the distal delivery catheter opening, whereby collapse of the compressor upon reception within the delivery catheter exerts a radial force upon the ED sufficient to compress the ED for reception in the delivery catheter.

45. A system for deploying a reversibly compressible endovascular device within a lumen of a vessel, the system comprising:

- a system for the radial compression of a reversibly compressible endovascular device (ED) prior to deployment as defined in any one of embodiments 37 to 41;
- a delivery catheter comprising proximal and distal delivery catheter openings, wherein the distal delivery catheter opening is for deploying the ED in to the lumen, and wherein the proximal delivery catheter opening is for receiving the ED from the delivery sheath, wherein the proximal delivery catheter opening is of a width equal to or greater than the width of the delivery sheath opening; and
- a hub connected to the proximal delivery catheter opening, the hub having a hub opening for receiving the delivery sheath in the hub when the ED is positioned in the delivery sheath, and positioning the delivery sheath in abutment with the proximal delivery catheter opening, wherein the push wire and compressor wire are operable to be advanced through the delivery catheter to urge the ED and the compressor through the delivery catheter and out distal delivery catheter opening, wherein the compressor is operable to expand.

46. The system of embodiment 45, wherein the push wire is operable to be retracted toward the hub to urge a deployed ED and expanded compressor toward the distal delivery catheter opening, whereby collapse of the compressor upon reception within the delivery catheter exerts a radial force upon the ED sufficient to compress the ED for reception in the delivery catheter.

47. A method of loading a reversibly compressible endovascular device (ED) into a delivery sheath having an interior width less than the radial width of the ED in an unexpanded position, the method comprising:

- compressing the ED from an expanded position to an unexpanded position for reception in the delivery sheath, wherein compressing comprises urging the ED in the expanded position through an interior space of a compressor, wherein the compressor comprises a tapered structure tapered from a distal compressor end toward a proximal compressor end of the tapered structure, wherein the width of the interior space at the distal compressor end is greater than the diameter of the ED in the expanded position and the width of the interior space at the proximal compressor end is less than the diameter of the ED in the expanded position, to radially compress the ED to an unexpanded position;

urging the ED in the unexpanded position through a proximal compressor opening at the proximal compressor end and into the delivery sheath through a delivery sheath opening.

48. The method of embodiment 47, wherein the tapered structure is resiliently collapsible.

49. The method of embodiment 48, wherein the tapered structure comprises a plurality of overlapping tongues coupled at the proximal compressor end, wherein each tongue tapers toward the proximal compressor end.

50. The method of embodiment 49, wherein each tongue is slidable over an adjacent tongue to change the cross sectional area of the interior space.

51. A method of loading a reversibly compressible endovascular device (ED) into a delivery sheath having a width less than the ED in an unexpanded position, the method comprising:

compressing the ED from an expanded position to an unexpanded position for reception in the delivery sheath, wherein compressing comprises collapsing a compressor, the compressor comprising a tapered structure having a wall defining an interior space in which the ED is positioned in the expanded position, wherein the wall exerts a radial force upon the ED to compress the ED, wherein the tapered structure is sized to be received in the delivery sheath when collapsed; and urging the compressor, with the ED positioned in the interior space in the unexpanded position, into the delivery sheath through a delivery sheath opening sized to receive the compressor in a collapsed position.

52. The method of embodiment 51, wherein collapsing the compressor comprises progressively reducing the radial cross sectional area of the interior space across the length of the tapered structure.

53. The method of embodiment 51 or 52, wherein the wall comprises a plurality of overlapping tongues coupled at a proximal end of the compressor, wherein each tongue tapers toward the proximal end of the compressor.

54. The method of embodiment 53, wherein the collapsing the compressor comprises sliding the overlapping tongues over each other to progressively reducing the radial cross sectional area of the interior space across the length of the tapered structure.

55. The method of any one of embodiments 51 to 54, further comprising frictionally engaging the ED with an interior surface of the wall to retain the ED in the interior space.

56. A method of deploying a reversibly compressible endovascular device in a vessel, the method comprising:

loading the ED in a delivery sheath according to a method as defined in any one of embodiments 47 to 55;

registering the delivery sheath opening with a proximal delivery catheter opening of a delivery catheter, wherein the delivery catheter is disposed within the vessel, and wherein a distal delivery catheter opening of the delivery catheter is at a target site in the vessel;

advancing the ED through the delivery sheath opening into the delivery catheter through the proximal delivery catheter opening, and through the delivery catheter toward a distal delivery catheter opening of the delivery catheter;

advancing the ED through the distal delivery catheter opening and into the lumen of the vessel at the target site; and expanding the ED in the lumen at the target site.

57. The method of embodiment 56, wherein the ED is a self-expanding ED and expanding the ED in the lumen involves allowing the ED to self-expand in the lumen.

58. The method of embodiment 57, wherein expanding the ED within the lumen comprises inflating a balloon disposed within the tubular body to expand the ED.

59. The method of embodiment 56, 57, or 58, wherein the compressor is a reversibly collapsible compressor, the method further comprising advancing the reversibly collapsible compressor through the distal delivery catheter opening into the lumen, and expanding the compressor to an expanded position.

60. The method of embodiment 59, wherein the compressor is a self-expanding compressor.

61. The method of embodiment 59 or 60, further comprising:

positioning the expanded ED within the interior space of the expanded compressor; and compressing the ED from the expanded position to an compressed position for reception in the delivery catheter, wherein compressing comprises collapsing the compressor, wherein the wall exerts a radial force upon the ED to compress the ED, wherein the tapered structure is sized to be received in the delivery catheter when collapsed; and urging the compressor, with the ED positioned in the interior space in the compressed position, into the delivery catheter through the distal delivery catheter opening to receive the compressor in a collapsed position.

62. The method of embodiment 61, further comprising repositioning the delivery catheter in the lumen at a second position and advancing the ED through the distal delivery catheter opening into the lumen of the vessel, and expanding the ED in the lumen.

63. The method of embodiment 62, wherein the ED is a self-expanding ED, and wherein expanding the ED in the lumen involves allowing the ED to self-expand in the lumen.

64. The method of any one of embodiments 56 to 63, wherein the delivery catheter comprises a hub connected to the proximal delivery catheter opening and sized to receive the distal delivery sheath end, wherein registering the delivery sheath opening with the proximal deliver catheter opening comprises inserting the delivery sheath within the hub and abutting the delivery sheath opening to the proximal delivery catheter opening.

65. A system for the radial compression of a reversibly compressible endovascular device (ED) prior to deployment, the system comprising:

the ED, wherein the ED comprises a tubular body, wherein the body is self-expandable between a compressed position and an non-compressed position, the tubular body having an inner surface, an outer surface, and opposed distal and proximal ED openings;

a delivery catheter sized to receive and maintain the ED in the compressed position, the delivery catheter having proximal and distal delivery catheter ends, and a distal delivery catheter opening at the distal delivery catheter end, wherein the distal delivery catheter opening has a width sized to receive the ED into the delivery catheter in a compressed form;

a compressor for compressing the ED for reception by the delivery catheter through the distal delivery catheter opening, wherein the compressor comprises:

a generally tapered structure defining an interior space, the tapered structure comprising distal and proximal compressor ends, wherein the proximal compressor end is proximal to the distal delivery catheter opening, wherein the distal compressor end comprises a distal compressor opening sized to receive the ED in the non-compressed position, wherein the tapered structure tapers from the distal compressor end toward the proximal compressor end such that the cross section of the interior space diminishes toward the proximal end, wherein the cross sectional area of the interior space at the proximal compressor end is equal to or less than the cross sectional area of the distal delivery catheter opening; and a push wire detachably attached to the ED and disposed within the delivery catheter, wherein the push wire is operable to be advanced proximally through the delivery catheter toward the proximal delivery catheter end to urge the ED through the compressor, whereby the ED is deformed into the compressed position as it is urged through the compressor.

66. The system of embodiment 65, wherein the compressor comprises a proximal compressor opening at the proximal compressor end.

67. The system of embodiment 66, wherein the proximal compressor opening is in communication with the distal delivery catheter opening.

68. The system of embodiment 66 or 67, wherein the width of the proximal compressor opening is smaller than the radial diameter of the ED when the ED is in the non-compressed position.

69. The system of embodiment 66, 67, or 68, wherein the push wire is disposed within the ED through the proximal compressor opening.

70. The system of any one of embodiments 66 to 69, wherein the push wire is operable to be advanced proximally through the delivery catheter to urge the ED through the proximal compressor opening and into the delivery catheter.

71. The system of any one of embodiments 65 to 70, wherein the compressor is a funnel.

72. The system of any one of embodiments 65 to 71, wherein the tapered structure comprises a unitary body.

73. The system of any one of embodiments 65 to 72, wherein the push wire is detachably attached to the ED by one or more threads.

74. The system of embodiment 73, wherein the one or more threads are attached to the inner surface of the ED.

75. The system of 73 or 74, wherein the one or more threads are electrolytically detachable from the ED.

76. The system of embodiment 73 or 74, wherein the one or more threads is a single wire comprising a lasso looped around the tubular body at a proximal end of the ED.

77. The system of embodiment 73, 74, or 75, wherein the one or more threads are mechanically detachable from the ED.

78. The system of any one of embodiments 65 to 77, wherein the compressor is detachable.

79. The system of any one of embodiments 65 to 68, wherein the compressor is collapsible.

80. The system of any one of embodiments 65 to 67, wherein the compressor is reversibly collapsible.

81. The system of embodiment 79 or 80, wherein the compressor comprises a braided structure.

82. The system of embodiment 81, wherein the braided structure is a polypropylene braided structure.

83. The system of embodiment 81, wherein the braid structure is a metal braided structure.

84. The system of embodiment 76 or 77, wherein the tapered structure comprises a plurality of overlapping tongues coupled at the proximal compressor end, wherein each tongue tapers toward the proximal compressor end.

85. The system of embodiment 79, 80, or 84, wherein the proximal compressor end is sized to be received within the delivery catheter through the distal delivery catheter opening.

86. The system of embodiment 85, wherein the compressor is sized to be received within the delivery catheter when the compressor is in a collapsed position.

87. The system of embodiment 86, wherein an inner wall of the delivery catheter is operable to exert a force against the side of the tapered structure, as the compressor is received within the delivery catheter, that is sufficient to collapse the compressor.

88. The system of any one of embodiments 78 to 87, wherein the push wire is attached to the compressor, wherein the compressor is attached to the ED by one or more threads.

89. The system of embodiment 88, wherein the one or more threads are attached to the inner surface of the ED.

90. The system of 88 or 89, wherein the one or more wires are electrolytically detachable from the ED.

91. The system of embodiment 88 or 89, wherein the one or more wires are mechanically detachable from the ED.

92. The system of embodiment 88 or 89, wherein the one or more threads is a single wire comprising a lasso looped around the tubular body at a proximal end of the ED.

93. The system of any one of embodiments 78 to 87, wherein the push wire is attached to the compressor, wherein an interior surface of the tapered structure is operable to frictionally engage the outer surface of the ED.

94. The system of any one of embodiments 78 to 93, wherein the push wire is operable to be advanced through the delivery catheter to urge the ED and the compressor toward the distal delivery catheter opening, whereby collapse of the compressor upon reception within the delivery catheter exerts a radial force upon the ED sufficient to compress the ED for reception in the delivery catheter.

95. The system of any one of embodiments 78 to 87, wherein the push wire is detachably attached to the ED by one or more threads.

96. The system of embodiment 95, wherein the one or more threads are attached to the inner surface of the ED.

97. The system of 95 or 96, wherein the one or more threads are electrolytically detachable from the ED.

98. The system of embodiment 85 or 96, wherein the one or more threads is a single wire comprising a lasso looped around the tubular body at a proximal end of the ED.

99. The system of embodiment 95, 96, or 98, wherein the one or more threads are mechanically detachable from the ED.

100. The system of any one of embodiments 89 to 93, wherein an interior surface of the tapered structure is operable to frictionally engage the outer surface of the ED.

101. The system of any one of embodiments 96 to 100, further comprising a hollow compressor wire attached to the compressor and disposed within the delivery catheter, wherein the compressor wire is operable to be advanced through the delivery catheter to urge the compressor through the distal delivery catheter opening, whereby the ED is deformed into the compressed position as it is urged through the compressor.

102. The system of embodiment 101, wherein the push wire is disposed within the compressor wire, wherein the push wire is operable to be advanced through the delivery catheter independently of the compressor wire to urge the ED independently of the compressor.

103. The system of embodiment 100, 101, or 102, further comprising a bump member disposed on the push wire between the ED and the compressor, wherein the bump member is for abutting the ED along the circumference of the proximal ED opening to urge the ED distally through the delivery sheath when the push wire is advanced distally through the delivery sheath.

104. The system of embodiment 101, 102, or 103, wherein the push wire and compressor wire are operable to be advanced proximally through the delivery catheter to urge the ED and the compressor toward the delivery catheter, whereby collapse of the compressor upon reception within the delivery catheter exerts a radial force upon the ED sufficient to compress the ED for reception in the delivery sheath.

105. The system of any one of embodiments 62 to 104, wherein the ED is a self-expanding ED.

106. A system for deploying a reversibly compressible endovascular device within a lumen of a vessel of a patient, the system comprising:

a system for the radial compression of a reversibly compressible endovascular device (ED) prior to deployment as defined in any one of embodiments 65 to 105;

a guide catheter comprising proximal and distal guide catheter openings, wherein the distal guide catheter opening is for positioning at a target site in the lumen, and wherein the proximal guide catheter opening is for receiving the delivery catheter external to the patient, wherein the proximal guide catheter opening is of a width greater than the width of the delivery catheter;

wherein the delivery catheter is operable to be inserted in the guide catheter through the proximal guide catheter opening and advanced through the guide catheter and out the distal guide catheter opening at the target site, wherein the push wire is operable to be advanced through the delivery catheter to urge the ED through the delivery catheter and out distal delivery catheter, wherein the ED is operable to expand.

107. The system of embodiment 106, wherein push wire is operable to be advanced through the delivery catheter to urge the compressor through the delivery catheter and out distal delivery catheter opening, wherein the compressor is operable to expand.

108. The system of embodiment 107, wherein the push wire is operable to be retracted proximally to urge a deployed ED and expanded compressor toward the distal delivery catheter opening, whereby collapse of the compressor upon reception within the delivery catheter exerts a radial force upon the ED sufficient to compress the ED for reception in the delivery catheter.

109. A system for deploying a reversibly compressible endovascular device within a lumen of a vessel of a patient, the system comprising:

a system for the radial compression of a reversibly compressible endovascular device (ED) prior to deployment as defined in any one of embodiments 101 to 105;

a guide catheter comprising proximal and distal guide catheter openings, wherein the distal guide catheter opening is for positioning at a target site in the lumen, and wherein the proximal guide catheter opening is for receiving the delivery catheter external to the patient, wherein the proximal guide catheter opening is of a width greater than the width of the delivery catheter; and wherein the push wire and compressor wire are operable to be advanced through the delivery catheter to urge the ED and the compressor through the delivery catheter and out distal delivery catheter opening, wherein the compressor is operable to expand.

110. The system of embodiment 109, wherein the push wire and compressor wire are operable to be retracted proximally to urge a deployed ED and expanded compressor toward the distal delivery catheter opening, whereby collapse of the compressor upon reception within the delivery catheter exerts a radial force upon the ED sufficient to compress the ED for reception in the delivery catheter.

111. A method of loading a reversibly compressible endovascular device (ED) into a delivery catheter having an interior width less than the radial width of the ED in an unexpanded position, the method comprising:

compressing the ED from an expanded position to an unexpanded position for reception in the delivery catheter, wherein compressing comprises urging the ED in the expanded position through an interior space of a compressor, wherein the compressor comprises a tapered structure tapered from a distal compressor end toward a proximal compressor end, wherein the width of the interior space at the distal compressor end is greater than the diameter of the ED in the expanded position and the width of the interior space at the proximal compressor end is less than the diameter of the ED in the expanded position, to radially compress the ED to an unexpanded position;

urging the ED in the unexpanded position through a proximal compressor opening at the proximal compressor end and into the delivery catheter through a distal delivery catheter opening.

112. The method of embodiment 111, wherein the tapered structure is resiliently collapsible.

113. The method of embodiment 111 or 112, wherein the tapered structure comprises a plurality of overlapping tongues coupled at the proximal compressor end, wherein each tongue tapers toward the second compressor end.

114. The method of embodiment 113, wherein each tongue is slidable over an adjacent tongue to change the cross sectional area of the interior space.

115. A method of loading a reversibly compressible endovascular device (ED) into a delivery sheath having a width less than the ED in an unexpanded position, the method comprising:

compressing the ED from an expanded position to an unexpanded position for reception in the delivery catheter, wherein compressing comprises collapsing a compressor, the compressor comprising a tapered structure having a wall defining an interior space in which the ED is positioned in the expanded position, wherein the wall exerts a radial force upon the ED to compress the ED, wherein the tapered structure is sized to be received in the delivery catheter when collapsed; and urging the compressor, with the ED positioned in the interior space in the unexpanded position, into the delivery catheter through a distal delivery catheter opening sized to receive the compressor in a collapsed position.

116. The method of embodiment 115, wherein collapsing the compressor comprises progressively reducing the radial cross sectional area of the interior space across the length of the tapered structure.

117. The method of embodiment 115 or 116, wherein the wall comprises a plurality of overlapping tongues coupled at a proximal compressor end of the compressor proximal to the distal delivery catheter opening, wherein each tongue tapers toward the proximal compressor end.

118. The method of embodiment 117, wherein the collapsing the compressor comprises sliding the overlapping tongues over each other to progressively reducing the radial cross sectional area of the interior space across the length of the tapered structure.

119. The method of any one of embodiments 115 to 118, further comprising frictionally engaging the ED with an interior surface of the wall to retain the ED in the interior space.

120. A method of deploying a reversibly compressible endovascular device in a vessel, the method comprising:

loading the ED in a delivery catheter according to a method as defined in any one of embodiments 111 to 119;

advancing the delivery catheter through a guide catheter disposed within the vessel, wherein the guide catheter has a distal guide catheter opening positioned at a target site in the vessel, to position the distal delivery catheter opening at the target site;

advancing the ED through the distal delivery catheter opening into the lumen of the vessel at a first position; and expanding the ED in the lumen.

121. The method of embodiment 120, wherein the ED is a self-expanding ED and expanding the ED in the lumen involves allowing the ED to self-expand in the lumen.

122. The method of embodiment 121, wherein expanding the ED within the lumen comprises inflating a balloon disposed within the tubular body to expand the ED.

123. The method of embodiment 120, 121, or 122, wherein the compressor is a reversibly collapsible compressor, wherein the method further comprises advancing the reversibly collapsible compressor through the distal delivery catheter opening and into the lumen, and expanding the compressor to an expanded position.

124. The method of embodiment 123, wherein the compressor is a self-expanding compressor.

125. The method of embodiment 123 or 124, further comprising:

positioning the expanded ED within the interior space of the expanded compressor; and compressing the ED from the expanded position to a compressed position for reception in the delivery catheter, wherein compressing comprises collapsing the compressor, wherein the wall exerts a radial force upon the ED to compress the ED, wherein the tapered structure is sized to be received in the delivery catheter when in a collapsed form; and urging the compressor, with the ED positioned in the interior space in the compressed position, into the delivery catheter through the distal delivery catheter opening to receive the compressor in a collapsed position.

126. The method of embodiment 125, further comprising repositioning the delivery catheter in the lumen at a second position and advancing the ED through the distal delivery catheter opening into the lumen of the vessel, and expanding the ED in the lumen at the second position.

127. The method of embodiment 126, wherein the ED is a self-expanding ED, and wherein expanding the ED in the lumen involves allowing the ED to self-expand in the lumen.

The invention claimed is:

1. A system for radial compression of a reversibly compressible endovascular device (ED) prior to deployment, the system comprising:

the ED, wherein the ED comprises a tubular body, wherein the tubular body is expandable between a compressed position and a non-compressed position, the tubular body having an inner surface, an outer surface, opposed distal and proximal ED ends, and opposed distal and proximal ED openings;

a delivery sheath sized to receive and maintain the ED in the compressed position, the delivery sheath having a delivery sheath opening having a diameter sized to receive the ED into the delivery sheath in a compressed form;

a collapsible compressor for compressing the ED for reception by the delivery sheath through the delivery sheath opening, wherein the compressor comprises a generally tapered structure defining an interior space, the tapered structure comprising distal and proximal compressor ends, wherein the proximal compressor end is proximal to the delivery sheath opening, wherein the distal compressor end comprises a distal compressor opening sized to receive the ED in the non-compressed position, wherein the tapered structure tapers from the distal compressor opening toward the proximal compressor end such that the cross section of the interior space diminishes toward the proximal compressor end, wherein the cross sectional area of the interior space at the proximal compressor end is equal to or less than the cross sectional area of the delivery sheath opening, and wherein an interior surface of the tapered structure is frictionally engaged with the outer surface of the ED, wherein the compressor is operable to be urged proximally with the ED frictionally engaged therein through the delivery sheath opening to collapse the compressor, wherein collapse of the compressor upon reception within the delivery sheath exerts a radial force upon the ED sufficient to compress the ED into the compressed position for reception in the delivery sheath; and a compressor support for providing lateral support for an exterior surface of the compressor as it is urged proximally through the delivery sheath opening, the compressor support comprising a body comprising an interior wall defining an insertion bore for receiving the compressor and ED within the body of the compressor support, the insertion bore having a generally frustoconical shape that tapers between a broad distal opening of the body of the compressor support through which the compressor and ED are received within the insertion bore in the non-compressed position and a narrower proximal opening of the body of the compressor support configured for communication with the delivery sheath opening, wherein the interior wall of the body of the compressor support is configured to provide lateral support to the exterior surface of the compressor as the compressor is urged proximally through the narrower proximal opening of the body of the compressor support and into the delivery sheath through delivery sheath opening.

2. The system of claim 1, wherein a width of the narrower proximal opening of the body of the compressor support is smaller than the diameter of the delivery sheath.

3. The system of claim 1, wherein a taper angle of the generally frustoconical shape is complimentary to a taper angle of the tapered structure of the compressor.

4. The system of claim 1, wherein the compressor support further comprises a first tubular portion defining an interior space of the first tubular portion in communication with the insertion bore of the body of the compressor support, the first tubular portion comprising distal and proximal first tubular portion ends, wherein the distal first tubular portion end is proximal to the narrower proximal opening of the body of the compressor support, wherein the first tubular portion has a width larger than the diameter of the delivery sheath.

5. The system of claim 1, wherein the compressor support further comprises a second tubular portion defining an interior space of the second tubular portion in communication with the insertion bore of the body of the compressor support, the second tubular portion comprising distal and proximal second tubular portion ends, wherein the proximal second tubular portion end is proximal to the broad distal opening of the body of the compressor support, wherein the second tubular portion has a length and width sized to receive the ED in the non-compressed position.

6. The system of claim 5, wherein the proximal second tubular portion end is the same size as the broad distal opening of the body of the compressor support.

7. The system of claim 1, further comprising a push wire detachably attached to the ED and disposed within the delivery sheath, wherein the push wire is also disposed within the ED though the proximal compressor opening and through the narrower proximal opening of the body of the compressor support.

8. The system of claim 1, further comprising a hollow compressor tube attached to the compressor and disposed within the delivery sheath, wherein the hollow compressor tube is operable to be advanced proximally through the delivery sheath to urge the compressor and the ED frictionally engaged therein through the delivery sheath opening.

9. A kit for a system for radial compression of a reversibly compressible endovascular device (ED) prior to deployment, the kit comprising:

the ED, wherein the ED comprises a tubular body, wherein the tubular body is expandable between a compressed position and a non-compressed position, the tubular body having an inner surface, an outer surface, opposed distal and proximal ED ends, and opposed distal and proximal ED openings;

a delivery sheath sized to receive and maintain the ED in the compressed position, the delivery sheath having a delivery sheath opening having a diameter sized to receive the ED into the delivery sheath in a compressed form;

a collapsible compressor for compressing the ED for reception by the delivery sheath through the delivery sheath opening, wherein the compressor comprises a generally tapered structure defining an interior space, the tapered structure comprising distal and proximal compressor ends, wherein the proximal compressor end is proximal to the delivery sheath opening, wherein the distal compressor end comprises a distal compressor opening sized to receive the ED in the non-compressed position, wherein the tapered structure tapers from the distal compressor opening toward the proximal compressor end such that the cross section of the interior space diminishes toward the proximal compressor end, wherein the cross sectional area of the interior space at the proximal compressor end is equal to or less than the cross sectional area of the delivery sheath opening, and wherein an interior surface of the tapered structure is frictionally engaged with the outer surface of the ED, wherein the compressor is operable to be urged proximally with the ED frictionally engaged therein through the delivery sheath opening to collapse the compressor, wherein collapse of the compressor upon reception within the delivery sheath exerts a radial force upon the ED sufficient to compress the ED into the compressed position for reception in the delivery sheath; and a compressor support for providing lateral support for an exterior surface of the compressor as it is urged proximally through the delivery sheath opening, the compressor support comprising a body comprising an interior wall defining an insertion bore for receiving the compressor and ED within the body of the compressor support, the insertion bore having a generally frustoconical shape that tapers between a broad distal opening of the body of the compressor support through which the compressor and ED are received within the insertion bore in the non-compressed position and a narrower proximal opening of the body of the compressor support configured for communication with the delivery sheath opening, wherein the interior wall of the body of the compressor support is configured to provide lateral support to the exterior surface of the compressor as the compressor is urged proximally through the narrower proximal opening of the body of the compressor support and into the delivery sheath through delivery sheath opening.

10. The kit of claim 9, wherein the compressor support further comprises a first tubular portion defining an interior space of the first tubular portion in communication with the insertion bore of the body of the compressor support, the first tubular portion comprising distal and proximal first tubular portion ends, wherein the distal first tubular portion end is proximal to the narrower proximal opening of the body of the compressor support, wherein the first tubular portion has a width larger than the diameter of the delivery sheath.

11. The kit of claim 9, wherein the compressor support further comprises a second tubular portion defining an interior space of the second tubular portion in communication with the insertion bore of the body of the compressor support, the second tubular portion comprising distal and proximal second tubular portion ends, wherein the proximal second tubular portion end is proximal to the broad distal opening of the body of the compressor support, wherein the second tubular portion has a length and width sized to receive the ED in the non-compressed position.

12. The kit of claim 11, further comprising a push wire detachably attached to the ED and disposed within the delivery sheath, wherein the push wire is also disposed within the ED though the proximal compressor opening and through the narrower proximal opening of the body of the compressor support.

13. The kit of claim 12, further comprising an end cap sized to be received in the distal second tubular portion end, wherein the end cap comprises a push wire opening therethrough, wherein the push wire is also disposed through the push wire opening.

* * * * *